United States Patent
Grigorov

(10) Patent No.: US 8,435,212 B2
(45) Date of Patent: May 7, 2013

(54) METHODS AND DEVICES FOR PROGRAMMABLE DELIVERY OF MICRODOSES OF LIQUID DRUGS AND OTHER FLUIDS

(76) Inventor: Leonid Grigorov, Redwood City, CA (US)

( * ) Notice: Subject to any disclaimer, the term of this patent is extended or adjusted under 35 U.S.C. 154(b) by 486 days.

(21) Appl. No.: 12/559,022

(22) Filed: Sep. 14, 2009

(65) Prior Publication Data

US 2010/0069830 A1    Mar. 18, 2010

Related U.S. Application Data

(60) Provisional application No. 61/192,056, filed on Sep. 15, 2008.

(51) Int. Cl.
*A61M 37/00* (2006.01)
*A61M 31/00* (2006.01)
*A61M 1/00* (2006.01)

(52) U.S. Cl.
USPC .............................. 604/131; 604/65; 604/151

(58) Field of Classification Search ............. 604/65–67, 604/131, 132, 151, 890.1, 891.1
See application file for complete search history.

(56) References Cited

U.S. PATENT DOCUMENTS

| | | | | |
|---|---|---|---|---|
| 6,613,280 | B2 * | 9/2003 | Myrick et al. | 422/45 |
| 6,616,677 | B2 * | 9/2003 | Gordon | 606/167 |
| 2002/0169439 | A1 * | 11/2002 | Flaherty | 604/891.1 |
| 2006/0184093 | A1 * | 8/2006 | Phipps et al. | 604/20 |
| 2008/0164275 | A1 * | 7/2008 | Poutiatine et al. | 221/15 |

* cited by examiner

*Primary Examiner* — Victoria P Shumate
*Assistant Examiner* — Rebecca E Eisenberg
(74) *Attorney, Agent, or Firm* — D. Benjamin Borson; Borson Law Group, P.C.

(57) ABSTRACT

Methods and compact automatic devices are provided for delivery of micro doses of liquid drugs to a patient. Devices have a fluid supply reservoir comprising an expandable indicator supplied with a sensor, a mechanism forcing the fluid to squeeze predetermined dose out, and a processor treating sensor's signals accordingly to preprogrammed algorithm. The method comprises steps: (a) initiating the delivery cycle, (b) acquiring sensor's signals, (c) treating signals in order to integrate an intensity of output flow and to determine when the squeezing-out force must be terminated, (d) terminating the cycle accordingly to processor's command. Self-testing of devices occurs while each fluid delivery cycle. Their high dosing precision exceeds that of known analogs about two orders of magnitude. A possibility to use low cost disposable exit port assembly and/or easy replaceable factory pre-filled cartridges is an additional advantage eliminating risks of overdosing, air bubbles, and/or compromised sterility.

18 Claims, 22 Drawing Sheets

METHODS AND DEVICES FOR PROGRAMMABLE DELIVERY OF MICRODOSES OF LIQUID DRUGS AND OTHER FLUIDS

CLAIM OF PRIORITY

This application claims priority to U.S. Provisional Patent Application No. 61/192,088 filed on Sep. 15, 2008. This application is herein incorporated fully by reference.

This U.S. Utility Patent Application claims priority to U.S. Provisional Patent Application No.: 61/192,056, filed Sep. 15, 2008, entitled: "Methods and Devices for Programmable Delivery of Microdoses of Liquid Drugs and Other Fluids," Leonid Grigorov, Inventor. The above provisional application is herein incorporated fully by reference.

FIELD OF THE INVENTION

The present invention relates to methods and devices for fluid delivery to patients. More particularly it relates to methods and compact programmable devices for the high precision delivery of low doses of fluids, and even more particularly it relates to methods and compact autonomous systems capable of introducing small and super small quantities of liquid drugs into a human body in accordance with a programmatically prescribed regime, supported by the delivery system over a prolonged period of the time.

BACKGROUND OF THE INVENTION

Devices for delivering drugs to patients have become an important aspect of modern pharmaceutical therapy. Advances in pump technology, both mechanical and electrical, have provided patients with options for having doses of needed drugs administered over prolonged periods of time with concomitant increases in effectiveness of treatment.

SUMMARY

Inventor has discovered new problems in the art of devices for long-term delivery of drugs to patients. These problems are discussed in detail below, but generally relate to the requirements that prior art devices must be precision made, and that with long-term use, the devices function degrades and doses can be poorly controlled, with consequent health problems. Inventor has also discovered simple devices that fulfill requirements of accurate and reproducible drug delivery, with low costs of manufacturing, low maintenance requirements, and other features that make it easier for patients to maintain their therapy.

Certain aspects of invention provide such new methods and new highly reliable compact programmable devices of the intravenous and/or hypodermic delivery of small and super small medicinal doses to a patient which combine simple construction having low manufacturing cost with an ability of delivering of small and super small doses of liquid drugs or other fluids with exceptionally high volume resolution exceeding that of existing devices at least one order of magnitude, and more desirable at least two orders of magnitude.

Other aspects of the invention provide delivery devices capable of fast and simple exchanging of ready-to-use factory pre-filled replaceable sterile cartridges. Such pre-filled cartridges can reduce the dangers occurring in connection with periodic necessity to refill the reservoir with additional drug, namely the dangers of both compromised sterility and non authorized introducing of air bubbles and dust contaminations by unskillful users.

Additional aspects of the invention mitigate risks of the leak and uncontrollable overdose of liquid medicine, and alarming in the case of the insurmountable occlusions with a minimum quantity of sensors detecting occlusions.

Further aspects of the invention provide fast and reliable detection of accidental changes of several critically important parameters occurring from time-to-time either outside or inside of any hydraulic part of the device. Such changes include partial occlusion of the flow passage, and further provide compensation of the changes to maintain the desired dosing regime even in the cases of the high level of incomplete occlusion or non-fatal internal damages of the device.

Yet further aspects of the invention include device of simple construction of the entire device, which can eliminate the need of using the expensive high-precision components, reduces the cost of production, and substantially increases long-term reliability of the whole device.

In certain embodiments, devices of the present invention comprise few functional blocks, namely: a hydraulic system "a" comprising a reservoir which contains a fluid and has at least one exit opening; a sensor system "b" producing output signals; a controlling system "c" comprising a programmable processor capable of both: (i) acquiring the output signals produced by the sensor system "b", and (ii) controlling a driving force system "d" which is capable of changing over time a force squeezing the fluid out of a reservoir. The hydraulic system "a" also comprises detectors ("detector means") connecting the exit opening with the reservoir. This detector means comprises at least one such component, which has a predetermined non-zero hydraulic resistance $R_2$ so that output hydraulic resistance of the device $R_{exit}$ cannot be less than $R_2$. The reservoir is supplied with at least one expandable element made of resilient material so that elastic deformation of at least part of this expandable element reflects the current status of the entire process of the fluid delivery. The sensor system "b" comprises at least one sensing element which is located in close proximity to said expandable element in order to be directly involved in producing analog input signals associated with the geometry of said expandable element changing due to elastic deformation. That is why both input and output signals of the sensor system "b" are associated with at least one geometric parameter of said expandable element. When the device is fully ready to work both said sensing element of the system "b" and said part of the expandable element involved in producing said analog input signals are located in the same housing. It is desirable that this housing comprises also at least a primary part of a transducer transforming input signals into output signals, and most preferably into digital output signals. The processor "c" is capable of acquiring said output signals produced by the system "b" and treating them accordingly to predetermined mathematical algorithm in order to operate the system "d". Few versions of preferred embodiments are described, which are different in regard of details, technical abilities, and algorithms controlling their performance. However, main features listed above are common for all versions of the invention, and each particular example of the disclosed embodiments is just a member of the same family of liquid drug delivery devices covered by the same general scope of the invention.

The fluid delivery process is a programmatically controlled sequence of cycles. Every cycle of the drug delivery is limited in time so that it provides predetermined micro-dose $D_0$ of the fluid related only to this particular cycle, whereas desirable average speed of the drug delivery depends on the adjustable rate of cycle's repetition controlled by the system "c". In order to begin each next cycle the processor initiates a driving force system "d" by a starting electric signal produced at programmatically predetermined moment $t_{st}$.

Before this moment the force squeezing the fluid out of the reservoir is kept about the zero, and the fluid in the reservoir is subjected to as low pressure as may be necessary to prevent the fluid to flow out of said exit opening. Actually, the initial low pressure in the reservoir is very close to an external pressure $P_{ext}$ which is typically equal external atmospheric pressure $P_{atm}$ applied to the fluid in the exit opening. That is a major reason why the fluid is stopped completely for a while preceding the cycle, and neither leakage nor overdosing can happen.

Driving force system "d" providing zero squeezing-out force before the cycle is allowed to satisfy extremely simple technical conditions. It must only be capable of fast producing the force squeezing the fluid continuously out of the reservoir after $t_{st}$, and then fast terminating said squeezing-out force after receiving an ending electric signal. That means that the desirable time-diagram of the squeezing-out force looks like quasi-rectangular pulse. One more reason why the design of the system "d" may be very simple is that its executive mechanism doesn't need to include high precision parts, and it doesn't matter what particular mechanism fulfills these requirements. For example, one can either move a piston of a syringe forth and back, or use a peristaltic mechanism, or even change quickly a pressure of a gas phase interacting with the fluid either directly or indirectly. It does not matter also if the amplitude of such pulse-like changing force varies significantly in different cycles because the method of the invention is capable of keeping the same high precision dosing in wide range of variations of said amplitude.

Due to said peculiarities of the system "d" mentioned in previous paragraph the devices of the invention posses uniquely high reliability. However, there is additional possibility to make this reliability even higher when the device of the invention is further supplied with additional emergency means providing a patient with an ability of manual application of a force squeezing the fluid out of the reservoir. Manual application of said force may be used temporarily in certain emergency cases if controlling system "c" detects substantial malfunctioning of the system "d" due to any reason. In such cases the patient should act under supervision of either acoustic or visual signals of the system "c" for as long period of the time as may be necessary to restore normal automatic functioning of the system "d".

Major novelties of the invention result from mutually correlated constructive features of both the reservoir and the sensor system "b" specifically combined with features of the method of the device operation. The reservoir comprising said expandable element has two hydraulically connected sections: (i) the first, called the compression section, wherein the squeezing-out force of the system "d" may be directly applied to limited surface area of the fluid, and (ii) the second, called the indicator section, wherein certain part of the expandable element is contacting with another limited surface area of the fluid filling the reservoir. Due to these two hydraulically connected sections are spatially separated, the direct action of pulse-like squeezing-out force in the compression section can only initiate the transfer of certain volume $\Delta V_{ind}(t)$ of the fluid in the direction of the indicator section. The arrival of additional volume $\Delta V_{ind}(t)$ of the fluid causes a resilient expansion of such part of the expandable element which relates to the indicator section of the reservoir and is involved in producing of the analog input signals. Volume expansion $\Delta V_{ind}(t)$ of the indicator section causes simultaneously both resilient deformation of said element and an appearance of time-dependent excessive pressure $\Delta P_{ind}(t)=P_{ind}(t)-P_{ext}$ in indicator section.

The deformation of the expandable element means that at least one geometric parameter of this element changes. Due to said expandable element is located in close proximity of at least one sensing element of the sensor system "b" located in the same housing, the analog input signals of the system "b" are associated with said variable geometric parameter reflecting both the change $\Delta V_{ind}(t)$ and the excessive pressure $\Delta P_{ind}(t)$. The point is that the information contained in these signals relates directly to the intensity of the fluid flow reaching the exit opening and, therefore, these signals represent the only real source of an information which can be used by the processor to control the fluid flow while each delivery cycle. Thus, the expandability of the indicator section is critically important for functioning of whole device.

There are many different choices of sensors producing analog input signals. Sensors may comprise either a piezoelectric element mechanically contacting with the expandable part of the indicator section, or non contact sensors represented by either a variable capacitor, or a magnetic sensor, or few optic sensors of different types. The transducer treating the analog input signals and transferring output signals to the processor may comprise standard auxiliary electronic means such as amplifiers, differential amplifiers, analog-to-digit converters, means capable of either transmitting or/and receiving any signals associated with analog input signals, including but not limited to wireless transmitting means or/and wireless receiving means if necessary or desirable.

Wireless transmitting and receiving any signals associated with said input signals may be reasonable if parts of the device are located in at least two housings or more. For example, the processor, the driving force system "d", and the compression section of the reservoir may be concentrated in one housing comprising means capable of wireless receiving signals. At the same time the expandable indicator section, necessary hydraulic resistors, input part of the sensor system "b" and means transmitting signals wirelessly may be deployed in another much smaller housing. In this case two reservoir's sections are connected with long flexible pipe allowing, if necessary, both connecting and disconnecting. Such small housing containing only few elements represents separate part of the device, namely an exit port assembly, which can be either deployed on a patient's skin or implanted inside patient's body because its volume may be less than 1 cm$^3$.

Wireless information exchange between electronic parts of the device, for example such as the processor and its control panel, may be very convenient when a patient needs to change processor's program. In this case the remote control panel may be located anywhere, especially if a patient is a little child and parental control is required. In addition, a long-distance wireless information exchange may be also used when necessary, for example, for urgent automatic communication between the programmable processor accumulating the information related to a patient and the personnel of medical center taking care of him or her.

General method of the invention is applicable to all devices of the invention comprising at least two such major features as: (i) the reservoir containing the fluid and having at least one resilient element contacting with said fluid, (ii) hydraulic means connecting said reservoir with at least one exit opening, said connecting means comprise a static hydraulic resistor having predetermined resistance $R_2$. The general method comprises following steps of every cycle: (a) initiating a non-zero force squeezing the fluid out of the reservoir; (b) acquiring at least one signal associated with at least one geometric parameter of said resilient element; (c) determining a moment $t_{end}$, said determining comprises treating said at least one acquired signal by either analog or digital processor capable of performing predetermined mathematical algorithm; and (d) terminating said force at a moment $t_{end}$ determined by said processor.

Before the step (a) there is no substantial squeezing-out force and the fluid in the reservoir is subjected to as low pressure as may be necessary to prevent the fluid to flow out of the exit opening. The step (a) begins when the driving force system "d" is initiated by at least one starting electric signal produced at predetermined moment $t_{st}$ detected by the processor accordingly to delivery instructions. In response the system "d" creates non-zero squeezing-out force quickly and applies it to limited surface area of the fluid in the compression section of the reservoir. Due to after $t_{st}$ the fluid is squeezed out of the compression section and arrives into the indicator section of the reservoir, the resilient element related to the indicator section is continuously subjected to depending on time pressure $P_{ind}(t)$ exceeding external pressure $P_{ext}$ within predetermined brackets $P_{max}+P_{ext}>P_{ind}(t)>P_{min}+P_{ext}$. The result is that the same continuous non-zero pressure difference $[P_{ind}(t)-P_{ext}]=\Delta P_{ind}(t)$ forces the fluid to flow out of the reservoir and causes certain geometric change of said resilient element which is reflected in signals of the sensor system. Steps (b) and (c) begin immediately after $t_{st}$ in order the processor could acquire and treat said signals as quickly as possible. This treatment determines quantitatively both pressure difference $\Delta P_{ind}(t)$ and a period $T_c=t_{end}-t_{st}$, wherein $T_c$ is such duration of the squeezing-out force which provides an equality of the predetermined dose $D_0$ and an actual dose delivered. The actual dose is represented quantitatively by a ratio, wherein a numerator is an integral found by integrating of said pressure difference $\Delta P_{ind}(t)$ over time since the moment $t_{st}$, whereas a denominator is a parameter expressing hydraulic resistance $R_{exit}$ of said means connecting the exit opening with the reservoir. The last step (d) comprises producing at least one ending electric signal at the moment of the real time coinciding with $t_{end}=T_c+t_{st}$ determined while step (c). This ending signal results in decreasing the squeezing-out force so that the pressure of the fluid in the reservoir can relax up to about its initial value which existed before the step (a). At this point the outgoing flow stops and current cycle of the fluid delivery ends so that the actual dose delivered to the exit opening is equal or very close to desirable dose $D_0$.

The advantage of both methods and devices of the invention is that the signals treated by the processor contain the information reflecting instant state of the entire hydraulic system "a" while each delivery cycle, including real time-dependence of the pressure squeezing the fluid out of the reservoir. In advanced devices of the invention these signals also reflect actual resistances of hydraulic elements involved in the delivery process. That means that all current variations of major parameters and variables of the device, causing variations of the intensity of outgoing fluid flow, are immediately taken by the processor into account accordingly to actual state of the device. That is why the duration of each cycle $T_c=t_{end}-t_{st}$ is always determined so that the actual dose delivered remains equal or very close to predetermined dose $D_0$ independently on variations of both external conditions and/or current performance of the device.

The excessive pressure created by simplified system "d" after $t_{st}$ is allowed to vary in different cycles in rather wide brackets $P_{max}/P_{min}$ up to about 10. This circumstance is taken into account by all mathematic algorithms determining the moment $t_{end}$ accordingly to constructive specificity of each particular device of the invention. For example, in most simple devices the exit opening may be hydraulically connected with any point of the reservoir, and both sections of the reservoir are connected by means having very low hydraulic resistance. In this case the actual dose is represented by the ratio wherein the integral located in the numerator is proportional to a sum of all signals acquired by the processor since the moment $t_{st}$, and the denominator is equal predetermined $R_2$ which is considered as the parameter expressing output resistance $R_{exit}$. If the $\Delta P_{ind}(t)$ is relatively stable during $T_c$ then even one signal acquired after $t_{st}$ may be enough for high precision determining $t_{end}$. In the case of unstable $\Delta P_{ind}(t)$ more signals should be acquired in order to keep high precision of fluid's dosing. Thus, even most simple devices of the invention are capable of complete eliminating fluctuations inherent for simple system "d" but their precision may drop in the case of an occlusion which increases output resistance significantly.

In advanced devices the exit opening is connected with the indicator section of the reservoir, and hydraulic communication between two spatially separated sections of the reservoir has a resistance $R_1$ which may not be less than $0.05 R_2$. More precisely the ratio $R_1/R_2$ exceeds 0.05 and is less than 200, more desirably it is in between 0.25 and 40, and most desirably it is in between 1 and 10. Due to $R_1/R_2$ exceeds 0.05 the kinetics of the excessive pressure $\Delta P_{ind}(t)$ in the indicator section becomes substantially slowed-down relatively sharp increase of the pressure in the compression section. The discovery of the invention is that slowed-down kinetics $\Delta P_{ind}(t)$ contains quantitative information about actual output resistance $R_{exit}$ related to means connecting the exit opening with the reservoir. In advanced devices actual $R_{exit}$ is determined by the specific algorithm which needs to treat at least two signals acquired while $T_c$. In this case the actual $R_{exit}$ determined is substituted to both the denominator of said ratio representing the actual dose of the fluid, and analytic expression of the integral constituting the numerator of this ratio. Due to actual parameters and variables of each cycle are determined, such as the excessive pressure $\Delta P_{ind}(t)$ and $R_{exit}$, advanced devices of the invention provide automatic adjustment of $T_c$ which leads to self-compensating both strong fluctuations of simple system "d" and potentially possible increase of the actual $R_{exit}$ occurring in the case of partial occlusion. The method of advanced devices further comprises producing an alarm signal if determined actual $R_{exit}$ exceeds predetermined level corresponding to an insurmountable occlusion. The said means that advanced devices of the invention do not require additional occlusion detector. Such devices need to be calibrated only one time before the work, and then they save calibrated parameters in processor's memory.

Most advanced devices satisfy all requirements considered in previous paragraph, but in addition their hydraulic means connecting the exit opening with the reservoir are further supplied with an element switching hydraulic resistance at predetermined pressure drop $P_{val}$. For example, this element may be a passive valve capable of switching its hydraulic resistance $R_{val}$ so that $R_2$ exceeds $R_{val}$, and more preferably $R_2$ exceeds $R_{val}$ at least by the order of magnitude when a pressure drop applied to this valve exceeds $P_{val}$. When the pressure drops below $P_{val}$ the resistance $R_{val}$ exceeds $R_2$, more desirably $R_{val}$ exceeds $R_2$ at least by the order of magnitude, and most desirable $R_{val}$ exceeds $R_2$ more than two orders of magnitude. In the presence of the self-switching valve the kinetics $\Delta P_{ind}(t)$ is combined of two different branches joining at calibrated pressure point $P_{val}$ which is used as an internal etalon. In order to analyze both branches and to obtain as high precision of determined $t_{end}$ as possible, the specific algorithm of most advanced devices of the invention requires acquiring and treating at least five, and most desirably significantly more than five signals while $T_c$. In addition to all self-compensating abilities mentioned above, this algorithm comprises calibrating whole system delivering the fluid, checking current performance of major components of this system, checking an amount of the fluid remaining in the reservoir. Also the method of most advanced devices further comprises producing a prompt report and/or alarm signal to inform a user if said amount of remaining fluid is too low, or any malfunctioning of the device is detected which cannot be self-compensated by said algorithm determining $t_{end}$. One more advantage is that after the moment $t_{end}$ the pressure drops below $P_{val}$ and the valve becomes closed. This eliminates entirely any risk of the fluid leakage and potential overdosing even in unlikely event of low residual pressure remaining in the reservoir after the end of the cycle. Due to potential residual pressure is very low, the construction of said locking valve can be simple and absolutely free of costly parts requiring high precision manufacturing.

High precision of the method related to most advanced devices of the invention may be further improved significantly if in the beginning of the step (a) before said moment $t_{st}$ the controlling system "c" produces also preliminary signal at the moment $t_{prel}$ which causes the driving force "d" to produce modest preliminary increase of the pressure in the reservoir so that this preliminary non-zero pressure increase doesn't exceed $P_{val}$. In this case an artificial state of full occlusion is intentionally created for short while between moments $t_{prel}$ and $t_{st}$ so that there is no fluid delivery at this while whereas signals of sensor system "b" measured between $t_{prel}$ and $t_{st}$ provide substantially increased precision of self-calibration of all parameters of the device.

Due to all quantitative parameters and variables defining the actual delivery are always known to the processor while each cycle, devices of the invention posses exceptional ability of immediate self-compensating of many unpredictable external and/or internal events occurring from time-to-time. One can imagine, for example, that typical delivery of desirable dose $D_0$ takes 6 s between $t_{st}$ and $t_{end}$. If simple system "d" is allowed of producing excessive pressure $\Delta P_{ind}(t)$ within brackets $P_{max}/P_{min}$ about 7, and in given cycle $\Delta P_{ind}(t)$ jumps accidentally three times above average value, then the processor detects this event and shortens the $T_c$ also three times. Namely, instead of normal 6 s it sends the ending signal after 2 s, thus keeping constant value of the actual output dose. In other example at normal $\Delta P_{ind}(t)$ the actual output resistance may spontaneously increase from normal $R_{exit}=R_2$ to very high $R_{exit}=20 R_2$ because of strong partial occlusion. In response the processor delays the ending signal as necessary (roughly about 30 s) to keep the actual output dose with no change. If the device of the invention is used for diabetes treatment of children under ten years, typical average rate of the insulin delivery is close to 10 mm$^3$/hour or less. If the delivery of the single dose $D_0$ about 1 mm$^3$/cycle takes 6 s in normal situation, the average rate requires only 10 cycles/hour. However, if medical situation requires the duration of the cycle to be as short as possible, the minimum dose of the same device can be as low as 0.02 mm$^3$/cycle with precision better than 0.001 mm$^3$. In the case of opposite medical emergency the same device can provide as high rate of the insulin delivery as 500 mm$^3$/hour. These parameters are about two orders of magnitude better than that of currently known devices of the insulin delivery. Also the ability of self-compensating makes devices of the invention exceptionally reliable because they are capable of withstanding either changes of such external parameters as air pressure and a temperature, or accidental (but not fatal) internal damages of the device because of mechanical shocks, and so on.

Simple hydraulic system of the invention admits manufacturing of parts of the device in many different forms. For example, the device and its hydraulic system can be divided in two parts so that the first part located in separate housing contains major electronics, all mechanics and the compression section of the reservoir. This part represents a separate programmable fluid supply device which can only squeeze the fluid out but cannot provide right dosing. The second separate part of entire device is the exit port assembly, consisting only of very small indicator section, few other passive hydraulic components, and minimum number of sensing elements, all located in low size separate housing. The advantage of this design is that small exit port assembly can be deployed anywhere, practically independently on the position of the first bigger part. When both parts are connected the entire device gets again its intrinsic ability of high precision fluid delivery which does not depend practically on the length of flexible connecting pipe made of a plastic even if this pipe can be substantially expanded by increased pressure while the delivery cycle. If the exit port assembly is implanted, it can get necessary electric power from the first part supplied with wires imbedded into the same plastic tube providing hydraulic communication between first and second parts of whole device.

The fluid can be placed in different cartridges, including traditional non replaceable, periodically refilled syringe-like cartridges. However, the preferred embodiment of the invention discloses a very simple, replaceable, factory pre-filled sterile cartridge, destined to be installed at least partially into a fluid delivery device and be fully disposable part of the device. The cartridge comprises: (i) means designed for stable locating of the installable part of this cartridge in the device; (ii) a reservoir comprising at least one expandable element made of resilient material which is located so that after the installation of the cartridge this element takes a position in a proximity of at least one element of a sensor system; (iii) means connecting the reservoir with at least one exit opening so that a hydraulic resistance of this connection is not less than predetermined non-zero value $R_2$; and (iv) a fluid pre-filling the reservoir, said fluid subjected to the same pressure in both the reservoir and any part of the means connecting the reservoir with the exit opening. Replaceable cartridges can be made of only low cost materials, such as elastic silicon rubber. They do not require electronics, active mechanisms, and/or high precision parts. Ready-to-use disposable cartridges can eliminate risks of compromised sterility and accidental introducing of either air bubbles or dust-like external contaminations, and can be easily replaced by any unskillful user.

DETAILED DESCRIPTION

Figure 1:
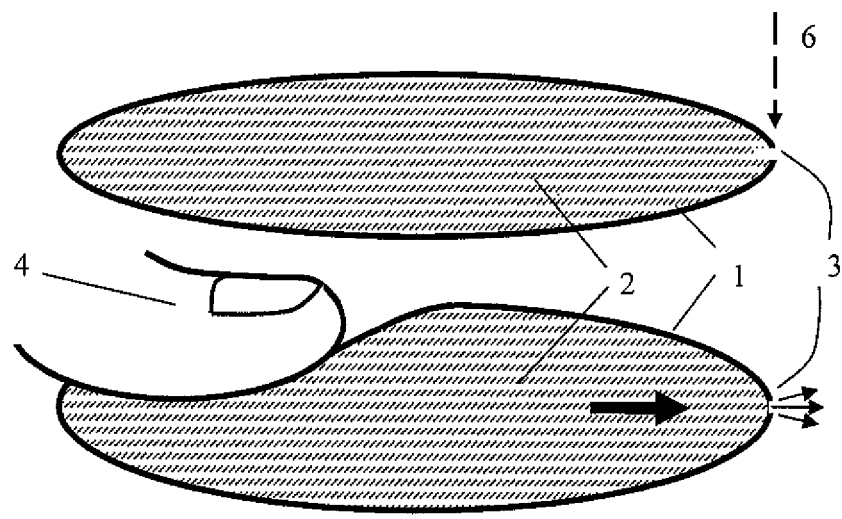
FIG. 1 depicts a method of the invention for fluid delivery by means of time-dependent compression of a reservoir made of resilient material and having one exit opening.

Accurately supplying patients with the necessary medicines during the prolonged course of treatment is an extremely critical medical task. It can be especially complex technically in the widespread case of chronic outpatient dispensary treatment (several days or more), where repeated, cyclic administration of prescribed small quantities of liquid medications are provided automatically by a compact programmed device (e.g., a pump), connected to the patient in such a way as not to interfere with his or her normal means of life. In order to supply further descriptions automatic devices for the delivery of the insulin have been chosen as an example capable of demonstrating quantitatively what reliability and high precision are required in a real life for the successful outpatient treatment of such a serious disease as diabetes. There are also many other diseases requiring at least the same high quality treatment.

At the present time there are many inventions, which relate both to entire systems of a compact devices of the hypodermic or intravenous delivery of liquid medications, and to the separate components of such devices. The use of some systems requires the application of the special methods. Technical requirements for portable automatic instruments for delivery of liquid medications can be high, because their correct and reliable working is required for maintaining the health and the life of the patient. Among many important requirements it is possible to recognize the following features.

(a) A device desirably can be the lightweight and reasonably low volume. Also it should possess the prolonged life of an operation (up to few days or more) and be attached to the patient, ensuring freedom of his or her activities and movements during the course of medical treatment. For example, at least 3 cm$^3$ of the insulin solution must be stored within the autonomous delivery device to provide the patient with such freedom for 3 days. In the case of drugs other than the insulin the autonomous automatic operation may continue much longer.

(b) For the entire period indicated the device can desirably automatically support the accuracy of the regime of the delivery of small and super small quantities of introduced medicine. In the case of insulin delivery, the desirable precision of a single dose should not exceed 0.1 mm$^3$ for adult patients, and less or about 0.01 mm$^3$ for little children.

(c) A device desirably can maintain precise dosing independent of possible changes of the external temperature, atmospheric pressure or other external variables, which frequently can occur during airplane flights or the change by the patient elevation above the sea level.

Known autonomous devices of the delivery of medicines can be divided into two basic classes, passive and active systems. The first class is represented by relatively simple passive systems, in which the only predetermined regime of the delivery of medicine is determined by the fixed construction of the device.

Class I: Passive Drug Delivery Systems

One example is found in U.S. Pat. No. 6,280,416 disclosing a device of the introduction of liquid drug with a constant velocity. The device comprises a fluid supply reservoir connected with the line of the delivery of medicine to the patient, and an additional reservoir filled with nontoxic gas and placed in the common housing together with the fluid supply reservoir in such a way that the fluid in the fluid supply reservoir would be exposed to the pressure within the housing. In other similar devices (for example, U.S. Pat. No. 6,283,943) the additional reservoir is filled with nontoxic gas creating subatmospheric pressure in the fluid supply reservoir for avoiding undesirable leakage.

However, none of the devices described make it possible to satisfy the above-indicated requirement (c) upon changing of such external parameters as either atmospheric pressure or the temperature. Also they are ineffective in the case of the occlusion of the drug delivery line because they do not comprise technical equipment capable to detect or remedy such events.

Some implanted compact devices, also intended for the liquid drug delivery with a prescribed constant speed (U.S. Pat. No. 5,785,681). It includes the reservoir in which the constant excess pressure is applied to liquid medicine. The fixed pressure in the reservoir is a driving force supporting the constant flow in the delivery line which connects the patient' body with the reservoir and includes a device for flow control. This device divides the delivery line in two consecutively joined sections. The first section contains a flow limiter having high hydraulic resistance. The second section, following after, contains both a second high-resistance limiter and parallel to it, a bypass having low hydraulic resistance. A diaphragm sensor, which reacts to a difference in the atmospheric pressure and the fluid pressure in the sensor station, is installed between the output of the first limiter and the entrance into the second flow limiter. This diaphragm pressure sensor provides mechanical control of the valve, which keeps the low resistance bypass open if the atmospheric pressure is close to the normal. At reduced atmospheric pressure, it shuts the bypass and re-directs the fluid's flow into the second limiter having high hydraulic resistance. Thus, the hydraulic impedance of the full line of the delivery reacts to a change in the external pressure, which contributes to the maintenance of the constant velocity of the fluid flow.

Major problems of a simple automatic device include one or more of the following. (i) Such systems are not flexible, and can support only one prescribed regime of the drug delivery, which cannot be changed during operation even in the case of medical need. (ii) Such systems are inadequate to react to dangerous events such as the occlusion of the delivery line in the region of its contact with the body of patient. (iii) Such systems are not capable of generating an alarm related to the end of the reserve of medicine.

Class II: Automatic Active Drug Delivery Systems

A second class includes active systems providing a controllable regime of drug delivery, determined by the programmed controller. One advantage of devices of this class is that a controller can be reprogrammed to another regime, in accordance with the medical need and the state of the patient. Such systems may be capable of independently reacting to some disturbances in the course of the drug delivery, or of promptly informing user about the serious disturbances for the purpose of the rapid correction of a dangerous situation. They also make it possible for a user to independently replenish stocks of medicine in the device, thus increasing the period of the patient independence. It is typically thought that the active programmed systems must not only correspond to the previously mentioned requirements (a, b, c), but also desirably should satisfy the following list of more complex additional conditions.

(d) It is desirable that a programmable device would be capable of automatic revealing small deviations of the real drug flow from what is prescribed by currently active program, said deviations caused, for example, by small leaks in the hydraulic system or by the partial occlusion of the drug delivery lines. It can also be desirable that the device be capable of mitigating the consequences of such accidental events.

(e) It is desirable that a device keeps predetermined high precision of drug delivery (which is typically about 1-2% of the predetermined dose) even in the case of unpredictable substantial temperature fluctuation, which may be expected within the range ±20° C. near normal room temperature.

(f) In the case of significant deviations which cannot be compensated for by device itself, it should report to a patient about the need for personal attention to correct the deviation. If the patient's health changes suddenly the device in his command must rapidly change the regime of the delivery whether for the introduction of additional drug or for the total cessation of its supply if necessary.

(g) The construction of the device desirably should minimize risks of random overdoses of liquid drug even in the case of total malfunction of the entire device, or individual subsystems or separate parts of the device.

(h) A device desirably should reliably work under conditions of prolonged shaking, impacts and vibrations caused by the displacements of a patient or transportation means. It should also be simple in control and maintenance, ensuring the correct regime of treatment for a patient with lowered mental activity and/or weakened tactile perception.

(i) A device desirably should permit refilling of medicine by a patient, to allow simple and rapid exchanging of an empty cartridge with a new factory pre-filled cartridge, while maintaining sterility and avoiding device damage caused by a user's unskillful handling.

(k) Assuming that all technical conditions enumerated above are satisfied, it is also desirable to have this simple construction of an entire system so that the cost of the production of both the device itself and replacement cartridges would be limited by the reasonable framework and cost, which offer real financial possibilities for the practical use of a device by a mass user.

None of the known active automatic fluid delivery systems, described in the patent literature, satisfies simultaneously the requirements recited above. Some of the known active compact systems of the liquid drug delivery include a fluid supply reservoir, a mechanism designed to squeeze the fluid out of said reservoir by the application of excess pressure to the liquid in the reservoir, a flow passage connecting the reservoir with the body of a patient, and programmable processor, which is intended to control the dose of the fluid delivered to exit the opening of the system. Active systems may be divided in two groups in regard of the method of an application of the force squeezing the fluid out of the reservoir.

In several systems of the first group, excessive pressure is created in a short interval of time by a pump, which is activated by an electrical motor. For example, this can be a peristaltic pump, which contains elastic tube filled with liquid and being sequentially deformed by compressing force, as it is described in U.S. Pat. No. 5,658,252, and in U.S. Pat. No. 5,772,409, and in the references to other patents being contained in it, which also assume the usage of a peristaltic pump. Other versions of compact active systems are syringe pumps, with a linearly moving piston driven by an electric motor. It is assumed that in these systems the piston stops upon delivering preprogrammed volume of the fluid by activating the proximity switches sending signals to the controller, for instance, described in U.S. Pat. No. 4,731,058, and the later U.S. Pat. No. 5,637,095. Due to high demands for reliability and accuracy of dosing, the geometry of both the pump casing and pump mechanism must correlate with design features of syringe's details by rather complex means, as it is described in U.S. Pat. No. 6,652,493. Also high requirements of medical dosing using these prior art devices can be achieved only if all parts of the syringe are made of hard materials treated mechanically with correspondingly high precision.

In prior art systems, the computer controls a short-term activation of the pump motor that makes possible, in the first place, introduction of a desired dose of the liquid drug at the appropriate time, and, in the second place, extend the life of the electrical batteries. The dosing program can be very complex as well. For example, the U.S. Pat. No. 5,181,910 describes the mathematical method of the control of the periods of time between the activations of the injecting pump for guaranteeing the linear change (increase or reduction) in the speed of the drug delivery to a patient.

In all devices of the first group the programmable processor concentrates its main "intellectual" activity on the control of specific mechanism squeezing the fluid out of fluid supply reservoir. A general idea is that proper control of the mechanism can provide predetermined dosage of the fluid. Simplest of such active systems do not contain sensors reflecting whether the exact or correct drug dosage is delivered, or the status of the flow passage, or the external variables, which can potentially influence the dosage. In such simplified cases the rigidly predetermined program of the controller does not permit the production of corrective commands, taking into account the real status of individual parts and the entire system as a whole. That is why the errors of the dosage, caused by, for example, increased friction of the piston of the syringe and/or by its irregular displacement in the housing are very possible. Neither the repair of the delivery system suffering with partial occlusions of the flow passage, nor providing an alarm signal with its complete occlusion is possible without additional sensors.

In other active systems of the first group disclosed in U.S. Pat. No. 4,559,038 the processor governs the dosage not only by starting and cutting off of the pump motor, but also by controlling of the system of valves. Due to the occlusion of delivery lines leading to exceeding a predetermined pressure level, the delivery system of U.S. Pat. No. 4,650,469 produces the occlusion signal with the use of the occlusion detector, which comprises electrical switches located both in the control module and in the flow passage.

In order to detect the occlusions leading to the elevated pressure in both flow passage and fluid supply reservoir, the invention of U.S. Pat. No. 6,485,465 is supplied with the occlusion sensor measuring the mechanical stress or pressure provided by the motor and located in the mechanism moving the piston. Other inventions described in U.S. Pat. No. 6,423,035 and U.S. Pat. No. 6,656,148 comprise both the detector of the effective force applied to piston's mechanism and an additional sensor, which measures the real position of this piston and transfers this information to the controller of the electric motor for achievement of the high dosing accuracy.

U.S. Pat. No. 5,935,106 describes a method of detecting occlusion in a drug delivery system. For this the pressure inside the elastic tube of a peristaltic pump is determined with the use of a pressure sensor brought in direct contact with the elastic tube to compress it slightly. This method comprises the preliminary determination of the stiffness coefficient of the tube together with the compressing sensor, then the first measurement of the force recorded by the sensor before the beginning of the fluid flow, and subsequent second measurement of the same force in the process of the fluid delivery. Finally the pressure of the liquid inside the elastic tube is calculated by subtracting of the first measurement from the second one where preliminarily measured stiffness coefficient is taken into account.

In this method, occlusion detection can be used only as the part of the complete delivery system, since it does not give quantitative information about the intensity of fluid flow, i.e., this one method is not sufficient for the precise dosage control. For the precise occlusion detection the system should have no less than two pressure sensors, located on the entrance of liquid into the pump and on its output respectively. This complicates the entire device and increases its cost.

Complex and expensive construction is a significant disadvantage in the majority of the known active compact systems of the first group which are using short-term pressure change as major method of liquid drug delivery. Typically these systems are represented by complex and costly combinations of high-precision actuators of the pump, mechanically or electro-mechanically operated valves, and also contain the diverse and numerous sensors which control force or pressure developed by pump engine, the position of such elements of the pump which determine the fluid dosage, pressure of the fluid in different sections of flow passage, position of replaceable cartridge in the pump casing, and etc.

However, even very high technical complexity does not eliminate the problem of inevitable gradual decrease of the device's precision during long-term use. This problem originates from low long-term reliability of certain mechanical parts requiring extremely high precision of both the initial manufacturing and further manipulation. For example, it has been mentioned before that typical syringe-like insulin delivery system must contain at least about 3 cm$^3$ of liquid drug and is capable of moving the piston having the area about 1 cm$^2$ so that its full path is as long as about 3 cm. Due to the aforementioned resolution of a typical one time dose of better than 0.1 mm$^3$, and more desirably better than 0.01 mm$^3$, the above means that the piston's position must be controlled with the resolution as high as about at least 1 micron, and more desirably about 0.1 micron. Actually, these numbers correspond to the relative precision of piston's mechanics better than or about 0.001% of the full piston's path. This problem seems to be too complex if one takes into account that notwithstanding the gradual wearing of all mechanical parts and the change of external conditions, the same high precision of the drug delivery must be conserved for at least few years of typical device's exploitation.

One more difficult problem of all syringe-like devices relates to potentially possible unpredictable temperature changes in the range ±20° C. Due to high temperature expansion coefficient about $3 \cdot 10^{-4}$, which is typical for all plastic materials, the length of 3 cm polymer housing of the syringe may fluctuate up to ±180 micron, whereas the length of piston's rod made of a metal fluctuates up to ±15 micron. That is why desirable mechanical precision in between 0.1-1 micron becomes practically impossible under such circumstances.

The second group of compact active systems providing liquid drug delivery consists of the devices in which the fluid filling the reservoir is constantly exposed at predetermined elevated pressure. In this case the main activity of the programmable processor is mostly concentrated on proper manipulation with hydraulic conductivity of such elements of the flow passage, which can be actively controlled by said processor.

As far as systems of the second group are considered, U.S. Pat. No. 6,736,796 B2 describes devices wherein a pump does not have an electric motor at all, and the liquid drug filling the reservoir is subjected to constant excess pressure. The design of the device includes a special port, which allows multiple refilling of the empty reservoir with new portions of liquid drugs. The pre-pressurized reservoir is connected with an exit opening of the delivery system by the flow passage which comprises two consecutively connected elements: (a) the elongated spiral capillary-like hydraulic resistor, and (b) externally controlled output valve which is constantly closed with the locking spring. At least two different points of the resistor, located upstream and downstream correspondingly, must be hydraulically connected with the opposite sides of the diaphragm of the differential pressure sensor so that the sensor is capable of measuring the pressure drop between these two separated points. The idea is that the signal produced by such a sensor is proportional to the intensity of the fluid flow at each given moment of the time and may be used by the processor controlling the dosage. This processor communicates with piezoelectric actuator which can overcome the action of the locking spring. That is why the instant state of the output valve obeys controlling signals of the processor.

Due to the fact that the output valve is normally closed, the fluid cannot flow before the beginning of the dosing because valve's hydraulic resistance is very high. At a preprogrammed start time the processor orders the actuator to open the valve. Its resistance drops sharply and the fluid, forced by constant excessive pressure in the reservoir, starts to flow through consecutively connected valve and capillary-like resistor. Due to the fact that the valve is now opened, the intensity of the fluid flow is limited only by the hydraulic resistance of the elongated capillary. The processor acquires sensor's signals and calculates this intensity. Then, using the calculated intensity of the fluid flow, the processor determines a specific moment when the dose delivered to the exit opening should coincide with the dose predetermined by the program. At this moment the processor makes the actuator close the valve and terminates the current cycle of fluid delivery. Taking into account that a typical single dose is very low and the fluid is subjected to rather high constant excessive pressure, the valve must be typically open for few milliseconds only.

At the first glance the technical idea disclosed above looks very attractive. However, this idea inherently contains two serious mechanical and medical problems. First of all, the open valve controlled by a piezoelectric actuator cannot have open clearance of more than few tens of microns. At the same time, high excessive pressure requires this valve to be closed very tightly before the dosing cycle. That is why the mechanical quality and corresponding cost of the actively controlled valve should be extremely high because all valve's parts must be made with at least sub-micron precision by the order of magnitude.

The requirements for such high precision raises substantial problems of reliability of the whole device. Such precisely made valves can easily become fully disabled if any hard sub-micron or micron-size contaminating particle is brought by the drug flow and lodges in the valve. In the case of improper use of the device, such contaminations (let say, ordinary dust) can be introduced by non-experienced users during reservoir refilling. Such unpredictable events can lead to very dangerous, uncontrollable drug leakage.

Another serious problem is that the precision of the dosing may change in time unpredictably. In accordance with the general idea, the processor uses the signals of a differential pressure sensor in order to calculate the magnitude of fluid flow. This involves calculation of the hydraulic resistance of an elongated capillary as given variable related to the fluid path between two points of the indicated capillary. However, due to the device not being capable of measuring this resistance, the processor's algorithm assumes this parameter to be factory pre-set constant. Evidently, it may be right in the beginning of the device's life cycle, but in long-term exploitation this resistance may change significantly if contaminating particles are brought into the device from outside, or even small air bubbles accumulate in the capillary's cavity during refilling. One more potential reason for substantial unpredictable fluctuation of capillary resistance is strong temperature dependence of fluid's viscosity. For example, the viscosity of a drug dissolved in a water changes from +73% to −52% in the range ±20° C. At different temperatures this leads to actual poor precision of drug dosing about 50-70% by the order of magnitude instead of required high numbers about 1-2%. Neither patient nor the device itself has any ability to control both gradual and unpredictable fast changes of capillary resistance, which directly influence the precision of the drug delivery.

Another technical design was disclosed in U.S. Pat. No. 6,740,059. This drug delivery system includes a separate remote control device, which is operated by the user in accordance with his medical needs, and can wirelessly communicate flow instructions to programmed local processors located in a separate housing together with two active valves obeying external controlling signals. The hydraulic system of this device is represented by the line of consecutively connected pre-pressurized fluid supply reservoir having high volume, changing in time gradually and capable of being refilled by the user. The first inlet valve is constantly closed, then the expandable bolus accumulator having low volume, and finally the second outlet valve is also constantly closed. The flow passage following after the outlet valve comprises the exit opening made in the form of sharp hard needle contacting directly with patient's body. Also the local processor may be connected to multiple different sensors, situated in different locations and including at least one of an occlusion detector, a fluid supply reservoir volume transducer, a leak detector, a reservoir empty detector, a pressure transducer, and many other detectors, or any combination of said multiple detectors. The abundance of detectors makes this system very complex and costly.

The dosing procedure consists of several operations determined by the program and the flow instructions received from remote control device. As it was mentioned above both valves are closed initially and there is no fluid flow before the delivery cycle. First of all the local processor opens the inlet valve at appropriate start moment. After that pre-pressurized fluid flows from the fluid supply reservoir to low volume accumulator until it gets predetermined low dose of liquid drug at elevated pressure. Then the local processor closes the inlet valve and thus cuts hydraulic communication between the accumulator and the fluid supply reservoir. Then the local processor opens the outlet valve and waits for some time until a rather small dose, accumulated in the accumulator's volume at elevated pressure, is transferred to the exit opening of the flow passage so that the pressure inside the accumulator gets is reduced to the same low value as external atmospheric pressure. Then the local processor closes the outlet valve and thus returns the whole system in its initial state ready for the next delivery cycle.

Due to the requirement that the driving force of this device is based on constantly pressurized fluid supply reservoir, the system suffers from the same disadvantages as the previous ones. To be more specific, both externally controlled valves are inevitably rather costly because of the necessity of extremely high precision of their manufacturing. A high-precision mechanical valve increases cost of the production of the entire system and reduces the reliability of its operation. At the same time the performance of such valves is extremely sensitive to the presence of any hard microscopic contaminations in the fluid. Accidental appearance of hard impurities or even invisible dust in valve's mechanism leads to the problem of unexpected drug leakage, which may cause dangerous overdosing. This can occur even during the insignificant pollution of valve clearance, introduced by unskillful user in the course of operating the system. The problem of non-controllable leakage has been unintentionally stressed in U.S. Pat. No. 6,740,059.

There is another device disclosed in U.S. Patent application No. 20060027523 (Feb. 9, 2006). The general idea of this application appears similar to some extent to the idea of the device discussed in two previous paragraphs (U.S. Pat. No. 6,740,059). In this application low doses of the fluid are transferred from a big fluid supply reservoir to a next smaller reservoir, which is intended to provide the user with programmatically controlled cycles of well measured micro-doses of the fluid. In order to fix a very low volume of each dose to about 0.2 $mm^3$, the small reservoir is hydraulically separated from the big one by an inlet valve, whereas the outlet valve separates this reservoir from the exit opening. The valves are self-controlled by their own pressure drop so that the fluid can move downstream only. What makes the major difference between the U.S. Pat. No. 6,740,059 and the application No. 20060027523 is: (a) a big reservoir of the application is not required to be subjected to predetermined excessive pressure; (b) both inlet and outlet valves are unavoidable parts of the pumping mechanism, wherein the small reservoir is supplied with a piezoelectric actuator capable of direct applying a force squeezing the fluid out; (d) the pumping mechanism is fully made of hard materials like a silicon or sapphire as used in semiconductor industry; (e) the hydraulic system of the device and pumping mechanism are made inseparable because they are built on the basis of solid state technology.

In 2007 the assignee Debiotech S.A. has announced that both entire hydraulic system and pumping mechanism of the diabetes therapy device, based on said application, are intended to be disposable weekly. Such devices would be extremely costly for long-term users because one week is a very short life-time of the complex and expensive parts of the device, requiring high degrees of precision in solid state fabrication. Because the fixed dose of one cycle is very low (it is about 1-2% of typical hourly dose for adult patients) a high repetition rate is required. This leads to increased power consumption, shortens the life of batteries, and increases both the weight and the size of portable device.

Taking into account that contemporary compact drug delivery devices are intended to be used by inexperienced patients, including children, teenagers, and seniors having decreased mental and technical levels, the potential dangers of both compromised sterility and the introducing of air bubbles were, before this invention, additional unresolved problems of existing devices, which result mainly from periodical patient's necessity to refill the device manually with fresh portion of the liquid drug. Serious medical consequences of all undesirable events listed above are often unpredictable.

Notwithstanding the forgoing, none of the prior art devices is capable of self-analyzing directed to detecting potential internal changes occurring with long-term use, and of self-correcting these changes so that the user should not take care of the technical state of the device supporting his or her life.

Terminology

It may be relevant to begin detailed descriptions of embodiments of the present invention with a discussion to eliminate potential terminological ambiguity related to hydraulic systems of liquid drug delivery devices. It can be desirable that a whole device is described as such static combination of all critically important parts where functional role of each particular part is brought in unambiguous correspondence with part's name expressed in commonly understood terms.

In that regard rather specific problem of hydraulic devices arises because a fluid placed inside a device becomes its inevitable liquid part widely distributed along full hydraulic path. This specific part is capable of changing its own shape and functioning in the process of dynamic interaction with many other details made of solid materials. In order to obtain the desirable fluid dose at final destination point the fluid must pass through multiple hydraulic elements intended to fulfill different functions. In complicated dynamic hydraulic systems actual functioning of each element may strongly depend on many features including but not limited to geometric shape and sizes of each selected element, peculiarities of a material which this element is made of, specific connection with other parts, the speed and viscosity of fluid flow, the shape of instant distribution of a pressure along full fluid path, and so on. A functional complexity becomes even stronger if some parameters (let say, a pressure distribution and/or speed of the flow) may change in time. The result may be that under variable circumstances some hydraulic parts begin to play more than one functional role. In this case a terminological ambiguity becomes inevitable if one uses conventional term related to that part which can reflect only one function and ignores other ones.

The said above can be easily demonstrated with simple example of potential ambiguity of such conventionally used terms as "a fluid supply reservoir" and "a flow passage" which are intended to express a relationship between what each selected part does and how this part is called. At the first glance the meanings of both terms mentioned above seem to be obvious from viewpoint of common sense. However, this first impression may be incorrect in some cases.

In order to demonstrate the idea, let first consider FIG. 1, having elastic reservoir 1 fully filled with the fluid 2 and having the shape of horizontally oriented ellipsoid supplied with one small exit opening 3 located directly on thin right wall as it is shown in upper portion of FIG. 1. Initially there is no output fluid flow because the pressure inside the reservoir coincides with outside pressure. If one applies, for example, the finger 4 to pressurize the fluid by elastic deformation of the left part of the reservoir 1 then the fluid begins to flow inside the reservoir in right direction as shown with thick arrow in bottom portion of FIG. 1, and then goes out through opening 3 (three thin arrows). It may be obvious for anyone skilled in the art that the only "a fluid supply reservoir" is unambiguously present in such simple delivery device, and a probability is about 100% that there is no such another part of this device which could be called "a flow passage".

If the shape of the reservoir 1 has been slightly changed near its center (upper portion of FIG. 2) so that finally the reservoir filled with the fluid 2 consists of two connected ellipsoid-like cavities—designated as L (left) and R (right)—where a fluid communication occurs through narrowed resistor 5 connecting two cavities. As before the only exit opening 3 exists on right wall of the cavity R. Now difficult questions arise in regard of modified delivery device of FIG. 2: What is a functional role of each cavity, and how should these cavities be characterized with the use of conventional terms?

Again, if finger 4 produces the force compressing the elastic wall of left cavity L (see the middle of FIG. 2) the pressure increases in left cavity L first. This makes the fluid to move to the right cavity, thus causing both the increase of the pressure in the cavity R and its elastic expansion. The result is that the fluid begins to flow out through the opening 3 of the cavity R. Now anyone has the right to say formally that the cavity L is "a fluid supply reservoir" whereas the cavity R serves as "a flow passage" because the fluid arrives to R from left cavity L through the resistor 5 and leaves through the opening 3. At the same time another expert has also the right to conclude that, as before, there is no "a flow passage" at all in hydraulic system shown in FIG. 2, but both cavities L and R constitute two parts of the same fluid supply reservoir 1, especially if connecting resistor 5 is not too narrow. However, the question remains without an answer what reliable criteria are to distinguish "too narrow" resistor from "not too narrow" one. The problem becomes even worse at the moment when forcing finger 4 is removed (see bottom of FIG. 2). Due to fast relaxation of elastic wall of the cavity L the pressure there drops quickly. At the same time the pressure in expanded elastic cavity R decreases with some kinetic delay in regard of fast pressure drop in the cavity L. The result is that some part of fluid flow is reversed to move from right to left because for a short while the pressure in the elastically expanded cavity R exceeds the pressure in the cavity L. Obviously, during this short while the cavity L supplies nothing and must be considered formally as "a flow passage". Moreover, during the same while the cavity R is serving as "a fluid supply reservoir" because the non-zero pressure remaining in the cavity R forces the fluid to escape through the opening 3. So, this example shows that just conventional terminology is not enough in some specific circumstances in which so-called "common sense" cannot be a good advisor.

Complicated dynamic behavior, considered above as a simple example only, reflects certain important features of embodiments of the invention. Definitions help to prevent any further terminological ambiguity. Such definitions applicable to whole description of preferred embodiments of the invention are provided below.

For the purpose of universally applicable definitions it is suggested to combine conventional terms reflecting functional roles of different parts with additional criteria based on either hydrodynamic properties of selected parts or certain geometric characteristics of fluid's body filling every part of a hydraulic system. In that regard it may be mentioned that hydraulic parts of a delivery device may be either connected inseparably in some cases or made separable in other cases providing more convenience for a customer. The point is that independent of particular constructions of separate parts and chosen types of their connections, such definitions become applicable only if a hydraulic system of a delivery device is thought to be entirely assembled and filled with the fluid to be in normal working state. When the system is fully assembled, the fluid placed inside represents a liquid continuum, which is contained within internal cavities of said parts. At least one cavity must have the exit opening or, in some embodiments, more than one exit openings to deliver the fluid to the area where liquid continuum ends and the fluid is to be subjected to an external pressure, which is an atmospheric pressure in certain cases. It may be desirable in some cases that entire hydraulic system comprises also at least one special cavity in which the surface of said liquid continuum is subjected to certain pressure of predetermined gas phase, said pressure is either normal atmospheric pressure or any different one.

The definitions provided below may contain the term "hydraulic element" or "selected hydraulic element" of the hydraulic system. Any of these terms must be understood as such part of whole hydraulic system of the device which has at least one cavity containing the fluid, said cavity limited by internal surfaces of walls made of non liquid material and having at least one such opening which can transfer the fluid either in or out of said cavity, or both in and out.

Definition No. 1. Preliminary comments: The usage of hydrodynamic criteria is always based on quantitative hydrodynamic parameters (such as, for example, an intensity of fluid flow or a value of hydraulic resistance of a selected element). They assume that selected local volume of the liquid continuum placed into the cavity of the selected element is moving with certain velocity through at least one given cross-section of the fluid path. For the purpose of present invention we provide the following definition No. 1: "The intensity $F$ of the fluid flow related to chosen cross-section of the fluid path is understood as a fluid's volume passing through said cross-section in one time unit, preferably in one second." Hereinafter all parameters and variables characterized by their quantitative values are set off in bold italic or Greek characters in order to make them better visible and distinguishable in the text of the description.

Figure 9:
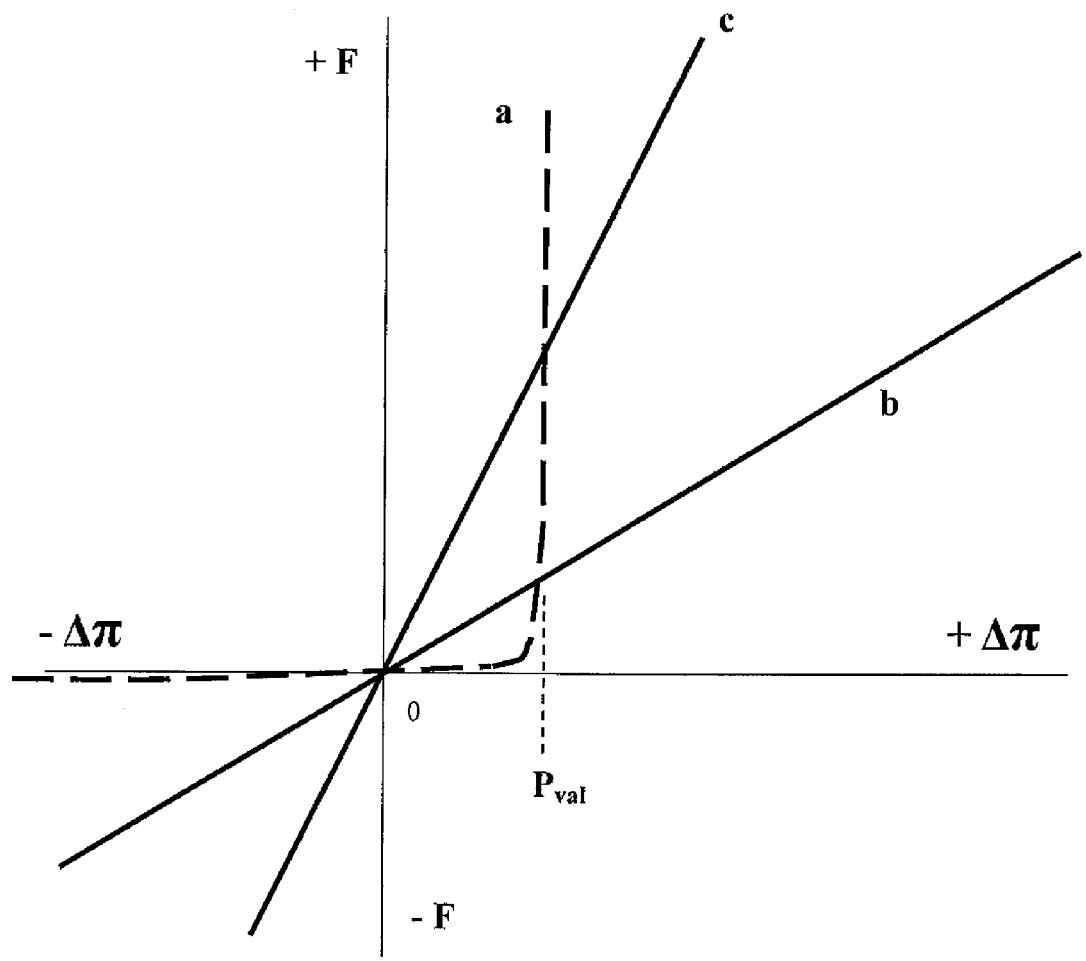
FIG. 9 depicts characteristics of embodiments of the invention, namely the dependencies of the intensity of fluid flow on the pressure drop, related to both linear and non linear passive elements of hydraulic system.

Definition No. 2. Preliminary comments: Both the concept "a static hydraulic resistor" and corresponding quantitative concept "a static hydraulic resistance $R$" are applicable to any selected element of a hydraulic system if the element satisfies the following conditions: (a) the element is not "a reservoir" determined by the definition No. 4 below; (b) two such spatially separated cross-sections of element's cavity can be chosen that the fluid arrives to said cavity through one cross-section and departs through another one; (c) the intensity $F$ of fluid flow is the same in both said cross-sections; (d) the movement of the fluid through said element is controlled only by a difference of hydraulic pressures applied to said cross-sections. A quantitative definition No. 2 is: "Any selected hydraulic element satisfying all above conditions of present paragraph is a static resistor and may be characterized by a value of its static hydraulic resistance $R$ related to the fluid path between two spatially separated cross-sections of a cavity of said element, where the value $R$ is a factor of following equation (1)

$$RF = \Delta\pi \qquad (Eq. 1)$$

where $F$ is the intensity of fluid flow passing from one said cross-section to another one, and $\Delta\pi$ is the pressure difference between both said cross-sections, providing that the pressure distribution along the surface of each said cross-section has approximately constant value." A static hydraulic resistor having at given temperature constant value $R$ may be also called "a linear static hydraulic resistor." In accordance with given definition No. 2 the hydraulic element satisfying all conditions above must be considered as "a static hydraulic resistor" independently on whether its resistance $R$ is a constant or it passively depends on either temperature or $\Delta\pi$. In the last case the resistor, having pressure-dependent resistance $R(\Delta\pi)$, may be also called "a non linear static hydraulic resistor". Graphical examples of both linear and non linear static hydraulic resistors are shown in FIG. 9.

In a given device any hydraulic element can not be called "a static resistor" if its resistance $R$ obeying formally the equation (1) may be also controlled by changing any device's parameter or variable other than a pressure difference $\Delta\pi$ defined above. For example, an externally controlled valve should be called a "dynamic hydraulic resistor" because controlling operations include at least one action other than a change of the pressure difference $\Delta\pi$.

Definition No. 3. Preliminary comments: Due to continuity of the liquid continuum distributed over multiple parts of a hydraulic system there may be a difficulty to determine where one part ends and next part begins. That is why the usage of geometric criteria requires explicitly determined concept "a local volume" of the fluid located within selected part. The following definition No. 3 is: "A local volume of the fluid located within the cavity of any selected element of a hydraulic system at any given moment of the time is equal to instantaneous volume of such part of the liquid continuum which is present inside closed surface formed by either entire internal surface of cavity's walls having no openings opened at said moment or both internal surface of cavity's walls having at least one opened opening and as many immovable virtual (or imaginary) surfaces as may be necessary to close cross-sections of all said openings opened at said moment, provided that stable shapes and positions of said virtual surfaces are chosen to obtain as low sum of areas of said cross-sections as possible." Hereinafter the word "imaginary" may be always substituted instead of the word "virtual" providing that both words have equivalent meaning.

As an example, one can use the definition No. 3 to find local volume of the fluid within the reservoir 1 shown in FIG. 1. This reservoir has only one opening, which may be closed with virtual plane oriented perpendicularly and crossing long axis of the ellipsoid 1 in the point shown by dashed arrow 6. Due to the reservoir is initially completely filled with the fluid the instant local volume of the fluid corresponding to the top view of FIG. 1 coincides with the volume limited by a combination of internal surface of non deformed reservoir's walls and the surface of virtual small disk closing the opening 3 in its most narrow place. Obviously, instant local volume of the fluid contained within the reservoir decreases in the process of the compression because some part of the fluid leaves (see bottom portion of FIG. 1). In accordance with definition No. 3 the local volume of the fluid cannot exceed the instant volume of the cavity but can be less under some circumstances. Such situation happens, for example, when the compression ends and reservoir's elastic wall returns to its initial shape but at this moment the amount of remaining fluid is less than before the compression.

Figure 2:
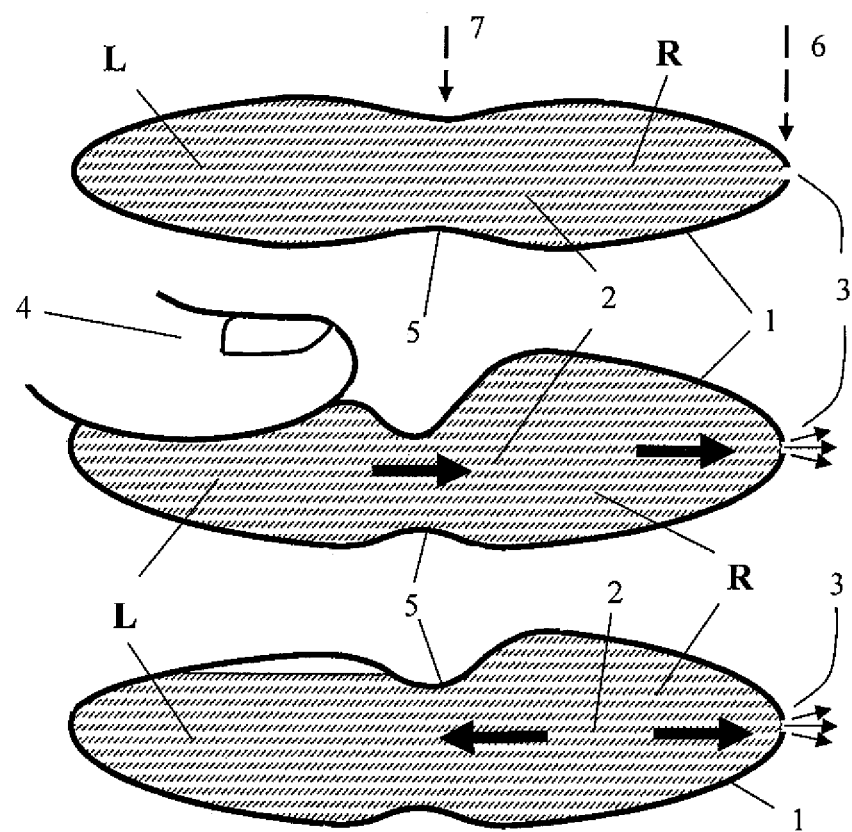
FIG. 2 depicts a method of this invention of the fluid delivery with the use of two communicating reservoirs where the left reservoir undergoes time-dependent compression and the right one provides time-dependent expansion because of resilient behavior of its walls.

A similar approach can be taken to determine the local volume of the fluid in section L of the reservoir 1 depicted in FIG. 2. Obviously, in this case the cavity L is limited by both the left part of reservoir's wall and one virtual plane shown with dashed arrow 7 which crosses the axis to close most narrow place of the resistor 5. At the same time the cavity R of the reservoir 1 depicted in FIG. 2 is limited by the right part of reservoir's wall and two virtual planes situated at positions 6 and 7 correspondingly to close both opening 3 and the resistor 5.

Definition No. 4. Preliminary comments: In order to define the term "a reservoir" we take into account that the main feature of any reservoir is its ability to contain different amounts of the fluid at different moments of the time so that the fluid arriving to a reservoir from anywhere may be accumulated, stored inside a reservoir, and supplied to other parts of given hydraulic system at appropriate moments. Obviously, this approach should be taken in accordance with specific features of each particular device. That is why any selected hydraulic element of given device may be considered as "a reservoir" only if its quantitatively expressed ability to contain different volumes of the fluid is critically required by working process of whole device. These considerations constitute the basis for following definition No. 4: "Independently on how the engineering design is done, any hydraulic element representing a part of a whole device is considered to be a reservoir if intended to perform the normal work of this device, considered as a certain process in the time, comprises such time changes of the local volume of the fluid contained within said element in accordance with the definition No. 3, which are important for proper working process of the whole device. A hydraulic element is not a reservoir if this element does not comply with conditions of previous sentence of this paragraph."

For example, if the proper function of a certain invention does not depend on naturally occurring insignificant thermal expansion of a specific element (let say, a pipe filled with the fluid) the definition No. 4 tells that such element may not be considered as "a reservoir". However, the same pipe incorporated by another invention may be considered as a reservoir if similar thermal expansion is anticipated as an inevitable part of device's functioning, and said change of pipe's volume is high enough quantitatively to be important for proper function of the device.

In that regard, in accordance with definition No. 4, both elastic cavities L and R shown in FIG. 2 correspond to the term "a reservoir" because the decrease of the compressed volume L is required to initiate a delivery of the fluid by means of the expansion of the part R, and even the final dose expelled from the part R in the very end of the process may be compared with full desirable dose. Due to the definition No. 4, the only question is whether cavities L and R are separate reservoirs or they are parts of the same reservoir. For the purpose of present invention an additional definition is provided to resolve this problem unambiguously.

Definition No. 5: "Any two hydraulically communicating reservoirs incorporated into the same device are just sections of the same reservoir if at any moment of device functioning the primary change of the fluid pressure, produced by any means including imaginary ones in any one reservoir of two, causes such immediate movement of a fluid through said hydraulic communication which results in secondary change of fluid pressure inside another reservoir of said two". In this definition the expression "imaginary means" means that an imaginary pressure change may be produced in any one reservoir of two even by certain virtual external appliance which can be imagined in principle but is not present in real device. If such pressure change is imagined in any moment of the functioning of a real device then all virtual consequences should be analyzed from viewpoint of real design of said device.

The definition No. 5 tells, for example, that both elastic reservoirs L and R shown in FIG. 2 are always understood as parts of their common reservoir 1 independently on whether the resistor 5 is wide or narrow because this resistor is always opened and can provide immediate fluid exchange between reservoirs L and R at any moment of the time. It does not matter whether secondary pressure change is delayed in time or occurs simultaneously with the primary one. It may be important also that the definition No. 5 doesn't depend on whether the communication represented by elastic neck changes its shape in time or not if this communication always remains opened. For better understanding of the definition No. 5 lets consider for a moment an opposite case shown in FIG. 2, wherein communication of reservoirs L and R comprises a valve, which may be in either opened or closed states at different moments in the device's operation. If a primary pressure change occurs in one reservoir at a specific moment when the valve is closed, then the fluid cannot move through the closed valve. Correspondingly, the primary pressure change in one reservoir causes no secondary pressure change in another reservoir. The definition No. 5 tells that in this case parts L and R must be defined as two independent reservoirs.

Definition No. 6: "Any element, providing hydraulic communication of two sections of the same reservoir, said sections being in compliance with the definition No. 5, must be also considered as a part of the same reservoir independently on whether this element taken separately comply with the definition No. 4 of "a reservoir" or not." However, in order to avoid ambiguity, in certain cases it may be desirable that names of elements complying with definition No. 6 are additionally characterized by specific terms. For example, instead of independent name "a pipe providing hydraulic resistance" one could say "a reservoir comprising two sections and a pipe connecting said sections and providing hydraulic resistance."

Additionally, hydrodynamic laws teach that stationary flow of any normal viscous fluid is possible only if a pressure applied to one limited surface area of an entire continuous fluid's body differs from a pressure applied to another limited surface area of the same fluid's body. This principle is exploited by all fluid delivery devices wherein the limited surface area of the fluid contained in the fluid supply reservoir is very different from limited surface area of the same fluid leaving the exit opening of the device. However, in certain devices the excessive pressure applied to the fluid is predetermined directly, for example, by using preliminary compressed gas phase having constant pressure. In other devices the excessive pressure is created indirectly by mechanical means, for example, by syringe-like or peristaltic pumps. Actually, the primary physical action of said mechanical means is to create only a certain force, and only then this force is converted into the fluid's pressure by an appropriate mechanism, for example, the syringe's piston shifted by said force. On the other hand, certain force is also applied to the fluid even if this is a force of direct interaction of limited surface area of the fluid with a gas phase. Taking all these considerations into account the only possible way to keep uniform terminology is to use a universal concept of a primary physical parameter, namely a force squeezing the fluid out of the reservoir. The discussion of specific technical means converting this force into the fluid's pressure is a special matter related to specific features of the invention and considered in appropriate section of present description.

One more ambiguity may be related to such widely used term as "a sensor," especially in regard of a determination of what each particular sensor is for. The term "a sensor" means a transducer transforming one specifically chosen parameter (let say, physical one) to another parameter, typically electric or electronic one, which may be conveniently used to provide an output signal. For example, the electric resistance of properly doped semiconductor plate brought into contact with a certain fluid can depend on the volume concentration of ions contained in this fluid. Thus, primarily this is a sensor of ion concentration. However, if a certain device exploits the diffusion of ions in the fluid, the osmotic pressure may change according to changes of ion concentration. So, such a device may mean "a sensor of ion concentration", but also may mean "a pressure sensor," notwithstanding the fact that just pressure as such does not influence the resistance of said semiconductor. Therefore, terminological ambiguity is obvious in this example. It arises only because real technical features are substituted by human's knowledge interpreting known relationship of both an osmotic pressure and an ion concentration in the fluid. In order to avoid this kind of terminological ambiguity the following definition No. 7 is provided.

Definition No. 7: "If an output signal (Sig) of a sensor system may be brought into correspondence with more than one interdependent parameters $(Par)_i$ related to the functioning of a given device, said sensor will be understood and defined as the sensor of such the only primary parameter (whether geometrical, or physical, or any other one), which physically permits said sensor to provide the highest partial sensitivity. In order to choose the only primary parameter the following method can apply: (a) full ranges of all interdependent parameters must be determined accordingly to the full range of normal device's functioning, then (b) a sensor's partial sensitivities $(S_{par})_i$ related to each separate i-parameter must be tested as follows: (i) all interdependent parameters must be fixed except selected one having number i; (ii) partial sensitivity $(S_{par})_i$ in regard of i-parameter having its own full range $(Ran)_i$ is defined as:

$$(S_{par})_i = |\Delta_i(Sig)/\Delta(Par)_i| \quad (Eq.2)$$

where $\Delta_i(Sig)$ is the change of sensor's output signal in response to such chosen change $\Delta(Par)_i$ of selected i-parameter which corresponds to constant ratio $\Delta(Par)_i/(Ran)_i$ for all i-parameters tested independently; and finally (c) the only primary parameter is to be determined which provides highest value of partial sensitivity $(S_{par})_i$ defined by the equation (2) above".

In order to make the definition No. 7 more clear, let return to previous example of the sensor with two interdependent parameters, namely the ion concentration and the pressure. After the full range of each of two parameters is found one must change only ion concentration, let say 10% of its full range, simultaneously keeping the fluid pressure constant by any means. Due to the fact that this semiconductor is physically sensitive to the change of ion concentration the sensor system produces a certain measurable response. After that only fluid pressure is to be changed the same 10% of pressure's full range by any means which do not involve the change of ion concentration. Obviously, only the zero or negligibly low sensor's response can be detected in the second test because the pressure as such does not influence physical properties of semiconductor plate. Accordingly to the definition No. 7 the ion concentration complies with a concept of primary parameter, and the sensor may be only called "the sensor of ion concentration."

The present description is supplied with several quantitative examples emphasizing advantages of the invention. For that purpose estimations have been chosen which relate only to a portable automatic device delivering insulin for treatment of the diabetes. However, the invention can be also used for the delivery of many other liquid drugs treating different diseases with different dosing regimes requiring different quantitative approach. That is a reason why insulin's delivery should be considered as just one example given for better understanding of the invention only, because it represents may be most impressive but only one of many potential fields of an application of the invention.

General Description of Fluid Delivery Devices and Methods of their Functioning

Different versions of fluid delivery devices are to be considered in the general scope of the present invention. Any particular member of this family is a programmable device comprising several systems which, in general, can be manufactured and used either as flexible combination of separate modules or as one compact setup. This feature, discussed later in more detail, provides customers with choices depending on the specific focus of each particular application. Advantages of the invention may be achieved if all systems and parts, shown schematically in general FIG. 3 with solid lines and numbered from 1 to 18, are involved in the fluid delivery process. Specific element 15 depicts direct interaction of a driving force system 14 with a hydraulic system. It may be desirable that optional alarm system 19, shown in FIG. 3 by a dotted line, is also included for user's convenience and safety but it is not critical for the device's functioning. Three thick white arrows control singnals 20, 21, and 22 depict important information transfer, making the systems work cooperatively whereas double-directed thick white arrow 23 depicts only certain physical interactions of an expandable element 10 with a sensor system 16. Thick black arrows 24, 25, 26, and 27 depict optional directions of signals and information transfer, which may be useful in certain embodiments.

Notwithstanding potential multiplicity of possible designs, devices of present invention exploit the same general method of cyclic fluid delivery. This method comprises the following major steps of every delivery cycle: (a) initiating a non-zero force squeezing a fluid out of a reservoir having an expandable element; (b) acquiring signals associated with a geometry of said expandable element; (c) treating acquired signals by a processor capable of performing predetermined mathematical calculations using an algorithm, which results in determining a moment $t_{end}$; (d) terminating the squeezing-out force at $t_{end}$ determined while the step (c). This is just general outline of the method provided only for better understanding of the content of few next sections describing technical details of systems of the invention. Specific cooperative interactions of said systems are disclosed below as well. More precise definitions of major steps and specific details of most important sub-steps of the general method are provided in final sections of the description. Special attention is focused on detailed description of mathematical algorithms that relate to different embodiments and lead to highly "intellectual" decisions made by the processor in accordance with variations of both external and internal circumstances.

A. Hydraulic System

Figure 3:
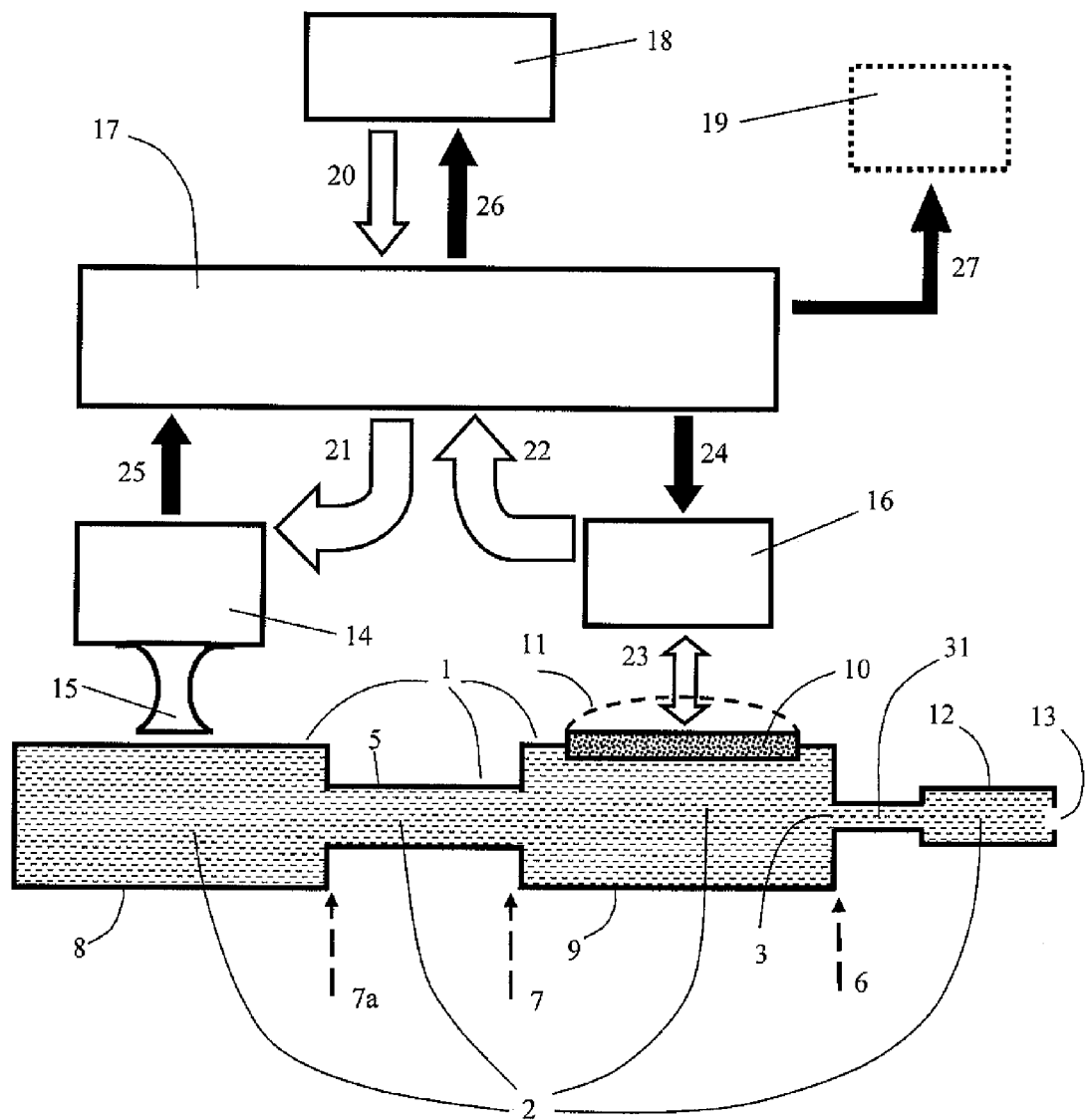
FIG. 3 depicts components and systems of fluid delivery device of the invention as well as some ways and directions of information transfer between all systems.

A hydraulic system shown schematically near the bottom of FIG. 3 comprises a reservoir 1 containing the fluid 2 and having at least one intermediate opening 3. In accordance with the definition No. 4 the entire cavity of the reservoir 1 is limited by all its walls and an imaginary plane located in the narrow cross-section of the intermediate opening 3 as shown in FIG. 3 by dashed arrow 6. The opening 3 connects reservoir 1 with means 12 providing hydraulic connection of reservoir 1 with at least one exit opening 13. Said connecting means 12 may be further called also "the flow passage" for brevity. An important feature of the flow passage 12, filled with the fluid 2, is that it comprises at least one static hydraulic resistor 31 having predetermined non-zero resistance $R_2$ which limits the intensity of the fluid flow through the exit opening 13. Means 12 may also comprise other elements contributing additional resistances. However, in any case, the presence of the resistor 31 makes full hydraulic resistance of means 12 not less than $R_2$.

Devices of the invention are intended to work in the external environment, and due to fact that exit opening 13 is a final point where the desirable dose of the fluid is to be delivered to, during the work of whole device the cross-section of this exit opening 13 is always subjected to external pressure $P_{ext}$. Most typically this external pressure $P_{ext}$ is equal atmospheric pressure $P_{atm}$ which can change in time unpredictably and should be considered as an external parameter.

Some devices may have a relatively long flow passage 12 made, for example, of flexible plastic pipe. In contrast to that other devices may have as short flow passage 12 as possible (see FIG. 15 for example). If the device is destined for a drug delivery, it may be desirable that the end of the flow passage is supplied with a sharp needle intended to be connected with patient's body. In this case the exit opening 13 is located on the tip of the needle. It can be appreciated that instead of the single exit opening 13, multiple exit openings of the flow passage 12 may be quite desirable in certain embodiments in order to provide more convenient consumption of the fluid dose delivered to a customer. A similar multi-needle exit port having many exit openings has been mentioned by Flaherty and Christopher in U.S. Pat. No. 6,740,059 incorporated herein fully by reference. However, independent of how many exit openings are present in each particular embodiment, anyone ordinary skilled in the art should appreciate that the performance of present invention does not depend on the number of said exit openings so long as at least one exit opening is subjected to the same external pressure mentioned above.

Reservoir 1 of embodiments of the present invention possesses several features discussed below. In order to simplify present description the general schematic view of FIG. 3 omits less important details, which can be made differently in different embodiments. However, one can find more technical details in FIGS. 4, 5, 6, 7, 15, 16, 21 related to a wide spectrum of examples of the reservoir 1. These details will be considered later at appropriate places of present description.

There is an important feature which relates to both the methods and the devices of the invention and makes the reservoir 1 quite different from the constantly pressurized reservoirs of devices disclosed in the prior art. The point is that before any delivery cycle the fluid in the reservoir 1 of the invention is mostly kept at low pressure, desirably as close to external pressure $P_{ext}$ as possible, and most desirably is equal to $P_{ext}$. Taking into account that the exit opening 13 is also subjected to the same pressure $P_{ext}$ at any time, before any delivery cycle the intensity of the fluid flow is as close to the zero as it may be desirable, because the force squeezing the fluid out of reservoir 1 is kept about zero and the fluid is not forced to flow outside. This initial state corresponds to top images of both FIG. 1 and FIG. 2. In accordance with the general method of the invention, the beginning of the fluid delivery cycle is initiated by an application of non-zero squeezing-out force to a certain surface area of the fluid in the reservoir 1. Direct interaction of this force with said fluid's surface area leads to an appearance of an excessive pressure of the fluid in the reservoir 1. This excessive pressure exceeds $P_{ext}$ and results in continuous squeezing the fluid out of the reservoir 1. Squeezing-out force continues up to a certain moment $t_{end}$ when preprogrammed processor produces an ending signal which leads to the termination of squeezing-out force and, correspondingly, results in stopping of outgoing fluid flow.

Accordingly to what is said in previous paragraph, it can be desirable to provide such design of the reservoir 1 that at least a limited surface area of the fluid contained in the reservoir 1 can directly interact with some technical means which are capable of changing said squeezing-out force over the time. The means may be designed rather differently as discussed later, both specific designs of said means and specific designs of each particular reservoir 1 must correspond to each other. However, independently on this specificity the common feature of any reservoir 1 of the invention is that it comprises at least two such sections 8 and 9 that each comply with the definition No. 4 of "a reservoir" if this section is considered separately. Each section is capable of fulfilling its own functional roles discussed below in many details. Another common feature is that hydraulic communication of both said sections is always opened and, in accordance with the definition No. 5, both sections are just parts of the same reservoir 1. It may be desirable in more advanced and most advanced embodiments that said opened hydraulic communication 5 connecting two said sections comprises a static hydraulic resistor having predetermined non-zero resistance $R_1$. Accordingly to the definition No. 6 whole element 5 including said resistor is also a part of the reservoir 1. Advanced embodiments require that the resistor $R_1$ provides substantially non-zero ratio $R_1/R_2$ exceeding about 0.05. In such cases the resistor $R_1$ is typically represented by specific detail, for example, a capillary (see FIG. 4) made of hard material. However, in certain simple embodiments discussed later the ratio $R_1/R_2$ is allowed to be less than about 0.05. In this case, shown for example in FIG. 5, low resistance of said hydraulic communication 5 does not require any such part which can be definitely identified as a resistor, because low non-zero resistance $R_1$ can be provided even by any short tube-like connecting detail.

Figure 15:
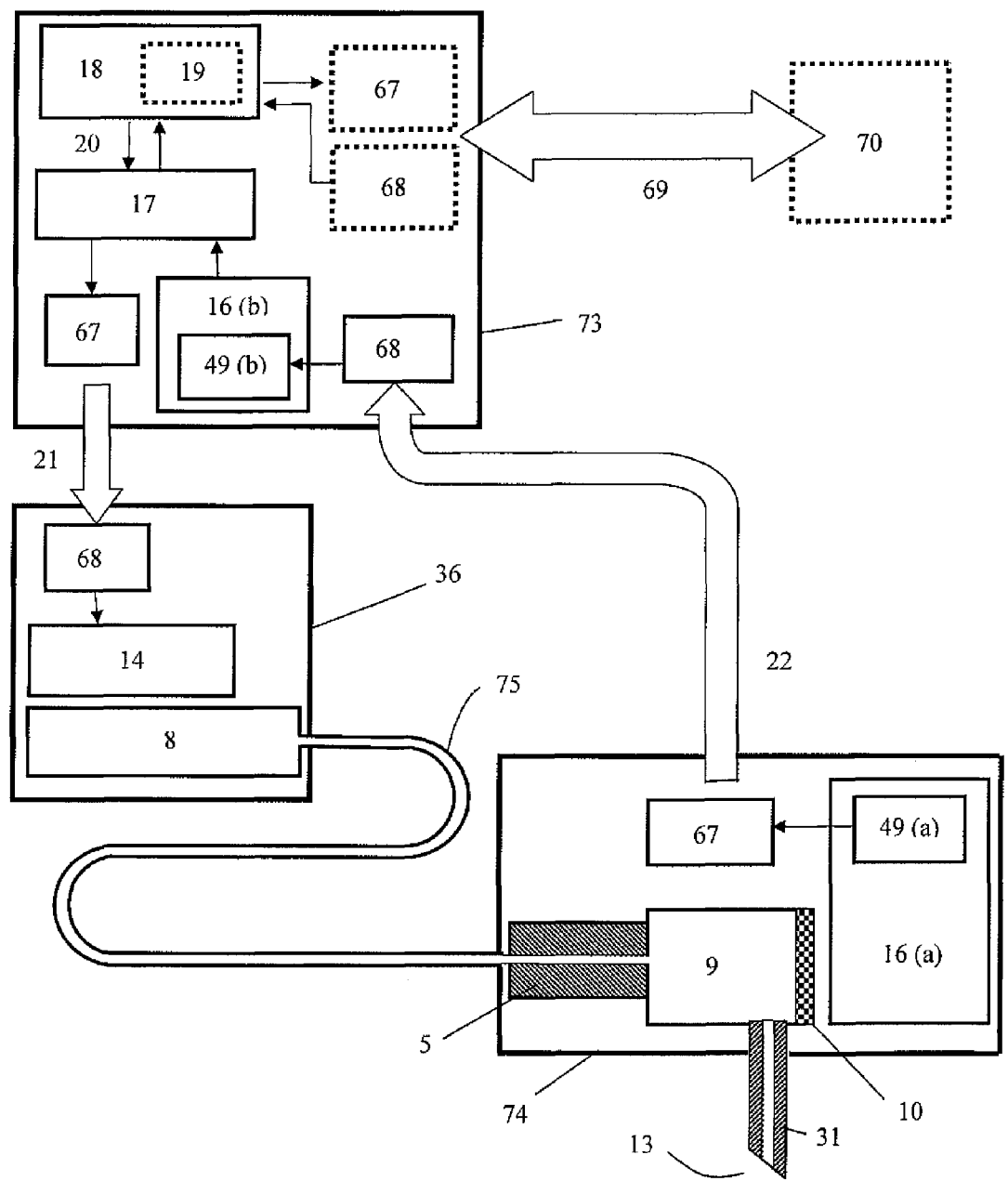
FIG. 15 depicts a block-scheme of a drug delivery device of the invention wherein parts of programmable control system are located in the same housing separated from housing(s) containing elements of hydraulic and sensor systems. This embodiment is supplied with means providing for remote information exchange, including wireless communication (shown with thick white arrows) between the control system and other systems located in different housings. Optional elements capable of providing long-distance communication of the device with outside party are shown with dotted lines.
Figure 16:
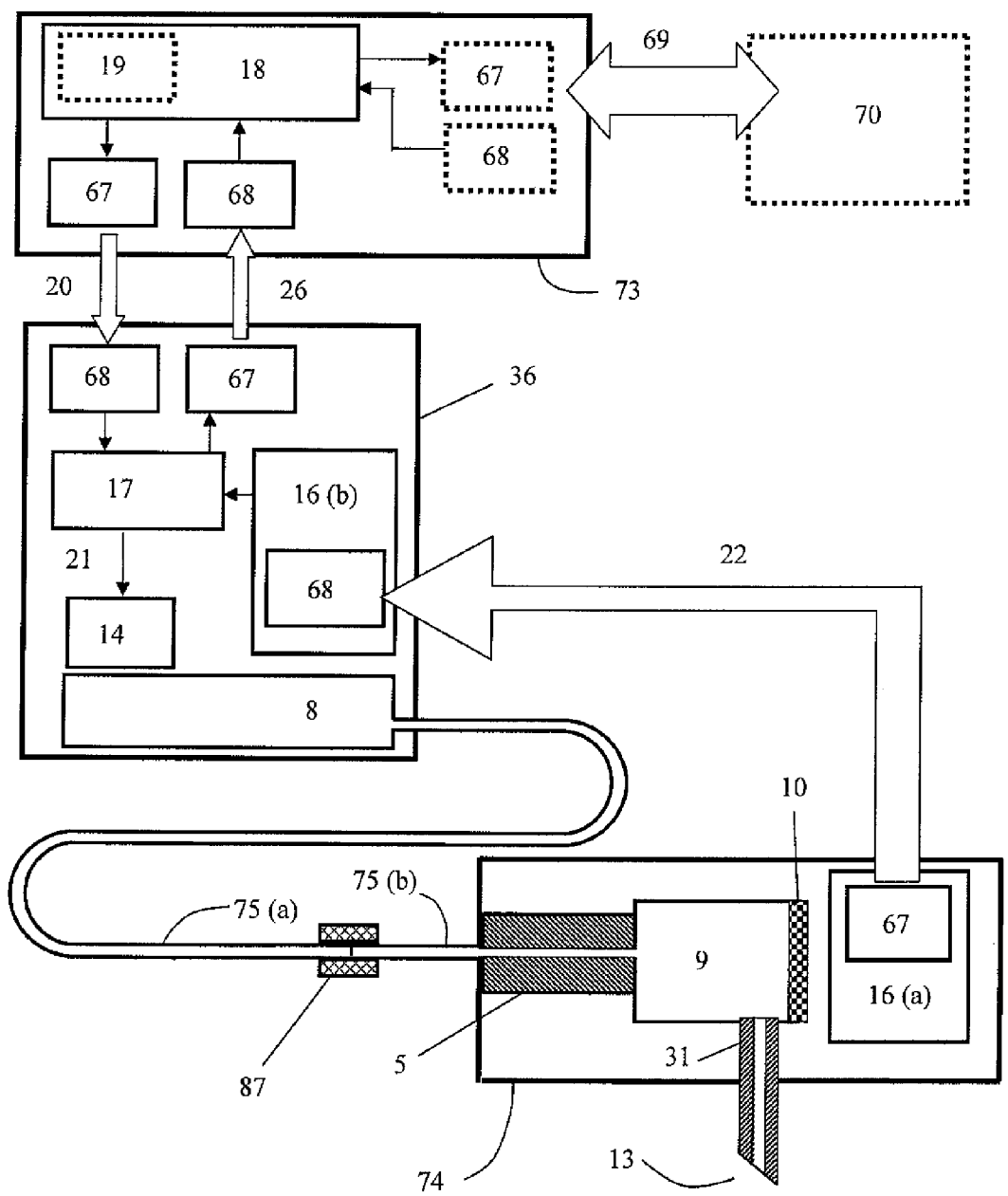
FIG. 16 depicts a block-scheme of an embodiment of this invention wherein remote information exchange is provided between programmable processor and a control panel located in different housings. This embodiment also depicts the compact design of an exit port assembly located in the separate housing and capable of being either conveniently deployed on patient's skin or implanted inside patient's body.

A spatial separation of two local volumes of the fluid located in two sections 8 and 9 can be desirable in certain embodiments. Such separation can allow each section to play its own functional roles. It is shown in FIG. 3 that the presence of connecting element 5 causes these sections to be actually separated. In many embodiments this separation occurs very naturally as one can see in FIGS. 4, 6, 7 related to such embodiments wherein all parts of the reservoir 1 are intended to be located in the same common housing 36. At the same time, spatial separation of the two sections is depicted in FIG. 15 and FIG. 16, wherein sections 8 and 9 are located in two different housings, 36 and 74, respectively. In these cases hydraulic communication between two sections of the reservoir 1 further can comprise a relatively long tube 75 (FIG. 15), or even two tubes 75(a) and 75(b) supplied with means 87 capable of both connecting and disconnecting said two tubes when necessary (see FIG. 16).

Figure 4:
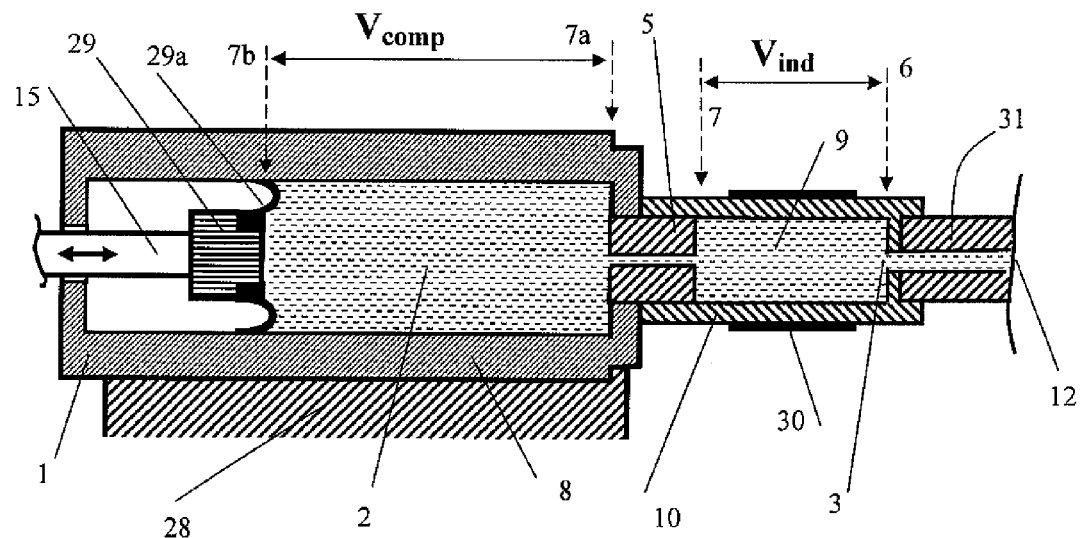
FIG. 4 depicts an embodiment of this invention having a reservoir filled with a fluid and made in the form of a syringe having both compression section and expandable indicator section separated by capillary-like static hydraulic resistor made so that its resistance $R_1$ exceeds output static resistance $R_2$ few times.

It can be desirable that reservoirs 1 of the invention have different forms and be made of different materials. The FIG. 4 shows a practical example of reservoir 1 made of a hard material in the form of a syringe firmly connected with the plate 28 situated within a housing 36 which isn't shown yet in FIG. 4. The section 8 made completely of hard material contains a piston 29 capable of moving forth and back accordingly in response to the force applied by the driving force system 14 (see also FIG. 3) via a driving shaft 15 connected to the piston. Accordingly to the teaching of present invention it may be also desirable that a ring 29a made of elastic material and shown schematically in FIG. 3 and FIG. 4 is a part of the piston 29. This sealing ring helps to avoid any leak of the fluid and provide some other important features of the invention discussed later. The piston 29 contacts with fluid 2 in reservoir 1, and simultaneously the same piston is a part of an electromechanical system 14. Full area of the piston 29 including the area of the ring 29a limits such surface area of the fluid's body which can directly interact with said squeezing-out force produced by the system 14. The second section 9, spatially separated from the section 8 by the resistor 5, comprises at least one expandable element 10. In this particular example the element is a short piece of a tube made of resilient material, for example, a silicon rubber or alike. An optional thin layer 30 covering the expandable tube 10 will be later discussed in the part of the description related to sensors. The FIG. 4 shows clearly that inside the section 9 the limited surface area of the fluid brought into a contact with expandable tube 10 is always spatially separated from already mentioned limited surface area of the fluid which undergoes direct interaction with squeezing-out force produced by the piston 29 in the section 8. Obviously, in this example the spatial separation of two said surface areas of the fluid located in the reservoir 1 is always preserved independently on current position of the piston 29. It should be also appreciated that the presence of at least one expandable element in the section 9 of the reservoir 1 provides the local internal volume of this section 9 with a feature of expandability too.

The example of the reservoir 1 shown in FIG. 4 corresponds to the group of other embodiments wherein the flow passage 12 connects the exit opening 13 directly with expandable section 9 so that both resistors 5 and 31 participate in the fluid transfer from the section 8 to the exit opening 13. It is desirable that said group of embodiments is characterized by such ratio of resistances $R_1/R_2$ that this ratio exceeds about 0.05 and is less than about 200, more desirably said ratio is in between about 0.25 and about 40, and most desirably said ratio is in between about 1 and about 10. The explanation of the reason why these quantitative limitations are desirable will be provided later.

Figure 5:
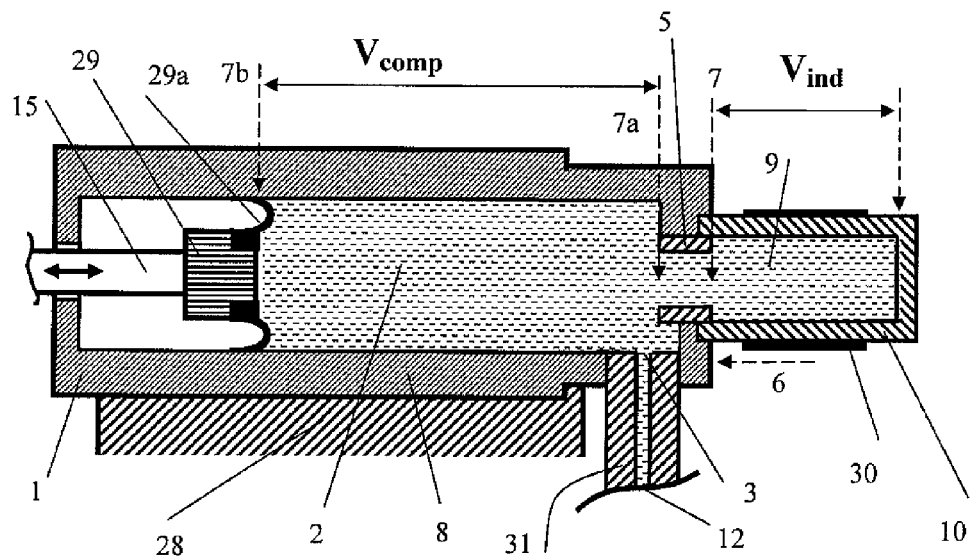
FIG. 5 depicts an example of syringe-like reservoir of this invention destined to be used in embodiments of the invention. This reservoir differs from the one shown in FIG. 4 in such points only that a flow passage is directly connected with compression section of the reservoir and $R_2$ exceeds $R_1$ more than one order of magnitude.

The FIG. 5 demonstrates another example of the syringe-like reservoir 1 designed to be used in simplified embodiments which do not require high resistance $R_1$. In this case the specific role of the resistor 5 becomes less important and the flow passage 12 may be directly connected with either the section 9 or the section 8 as shown in FIG. 5. In the last case the fluid can reach the exit opening without traveling through the resistor 5. That is a reason why the geometry of this resistor is not too much important for simplified devices corresponding to FIG. 5. In this case, the imaginary plane 6, separating the cavity of the reservoir 1 from the beginning of the flow passage 12, takes another position in accordance with new position of the opening 3. However, the requirement of a spatial separation of two said sections of the reservoir 1 remains in force in any case, and both embodiments shown in FIG. 4 and FIG. 5 fall into the scope of the present invention but each of them requires a specifically modified mathematical algorithm related to the method of the invention.

It can be appreciated that formal separation of two said sections of the reservoir 1 may be difficult in certain embodiments. Such difficulty is demonstrated by the example shown in FIG. 5 where the resistor 5 having low resistance is very short. Dashed arrows 7 and 7a in FIG. 3 help to depict that even in such cases two sections 8 and 9 can be formally separated by two virtual surfaces providing two imaginary cross-sections of the cavity of the reservoir 1 in its part related to the resistor 5. Proper choice of stable positions of imaginary surfaces 7 and 7a allows at least formal separating and quantitative determining two local volumes corresponding to sections 8 and 9 independently on how each particular reservoir 1 is designed. Because said virtual separation can be done voluntary in certain embodiments, for correct evaluation of the resistance $R_1$ it can be desirable that the distance between surfaces 7 and 7a measured along fluid's path in the cavity of the resistor 5 is chosen as high as possible until the definition No. 2 allows considering the resistor 5 as "a static resistor" having highest possible value of the resistance $R_1$.

It should be appreciated that the shape of the local cavity of the resistor 5 may differ in different embodiments, and, correspondingly, the distance between virtual surfaces 7 and 7a can vary in rather wide range. The simplest example of the shape of the resistor 5 is a capillary having appropriate length and such small internal diameter lower than internal transverse sizes of both sections 8 and 9 as shown in FIG. 4. In this case virtual surfaces 7 and 7a are to be situated on opposite ends of the capillary because it corresponds to the highest value of $R_1$. However, in some embodiments, the internal diameter of the resistor 5 may be comparable with transverse size of either section 8 or section 9 as shown in FIG. 5. In such case the resistance $R_1$ may be very low but in any case the value $R_1$ exceeds zero. In certain embodiments, the resistor 5 can be made in the form of thin diaphragm where the distance between virtual surfaces 7 and 7a may be so low that both surfaces practically coincide. However, many other shapes of the resistor 5 can be used as well if they provide desirable non-zero value $R_1$ of the resistance.

Figure 10:
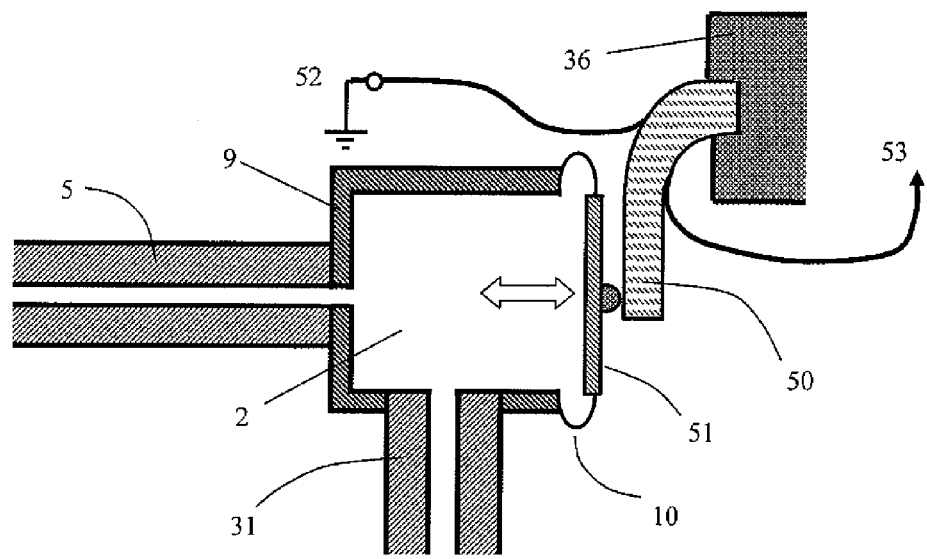
FIG. 10 depicts the example of an embodiment of the invention having a direct mechanical contact piezoelectric sensor combined with entirely metallic indicator section of non replaceable reservoir.
Figure 11:
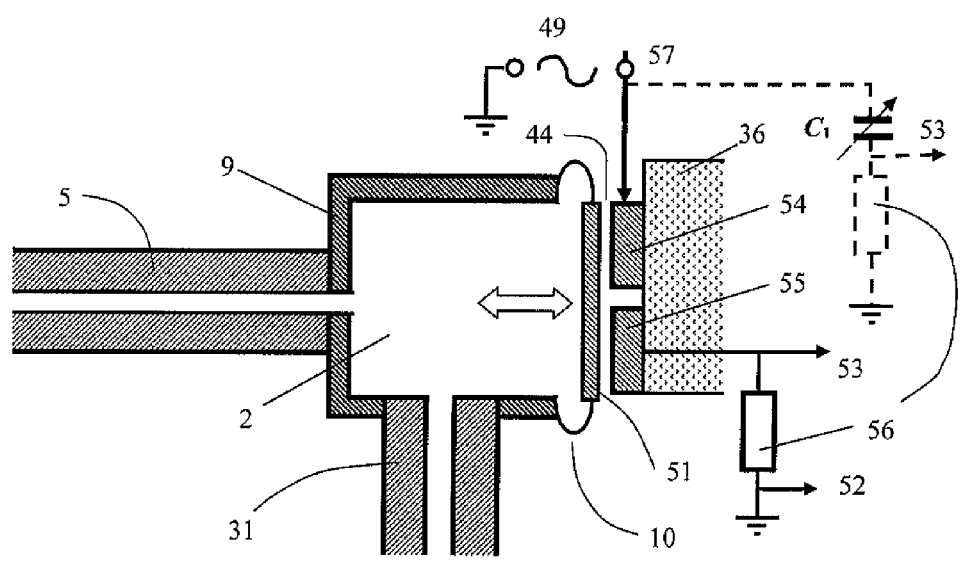
FIG. 11 depicts an embodiment of the invention having a non-contact capacitor sensor combined with a metallic indicator section of a non-replaceable reservoir.

It should be appreciated by anyone skilled in the art that the spectrum of different designs and different materials of the reservoir 1 is much wider than just syringe-like examples shown in FIG. 4 and FIG. 5. The point is that the design of the section 9 should correlate with the particular choice and design of the sensor system 16 discussed later. The teaching of the invention tells that the only general point of this correlation is that, independently on specificity of each particular design of the section 9 of the reservoir 1, this section must be expandable because it is always supplied with at least one expandable element 10 made of a resilient material. The examples of the expandable section 9, made entirely of a metal and including a resilient sylphon bellows 10 either welded or soldered with non-deformable metallic walls of the section 9, are shown in FIG. 10 and FIG. 11. These examples are very different from others shown in FIGS. 4, 5, 7, 12, 13, 14 wherein expandable wall 10 of the sections 9 is made at least partially of elastic polymer materials whether transparent in some cases or not in other cases.

Figure 20:
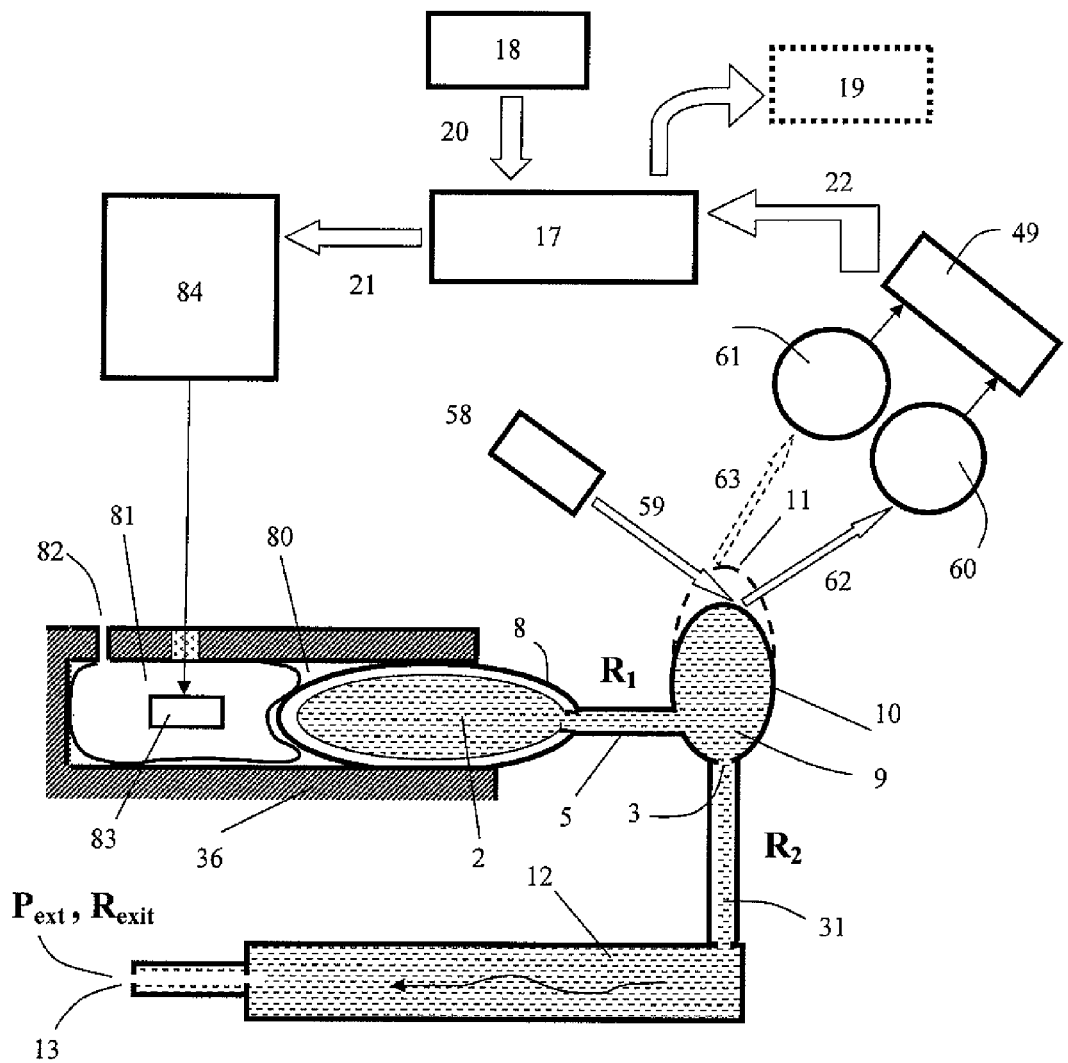
FIG. 20 depicts schematically another embodiment of the invention wherein the flow passage is connected with the expandable indicator section of the reservoir in accordance with the design represented in more details in whether FIG. 7 or FIG. 4. It also depicts the design of a driving force system having no motor at all wherein the fluid is forced to flow by controllable pressure of the gas, such as air, located in the additional elastic bag which is situated in close proximity to the elastic wall of the compression section of the reservoir.
Figure 21:
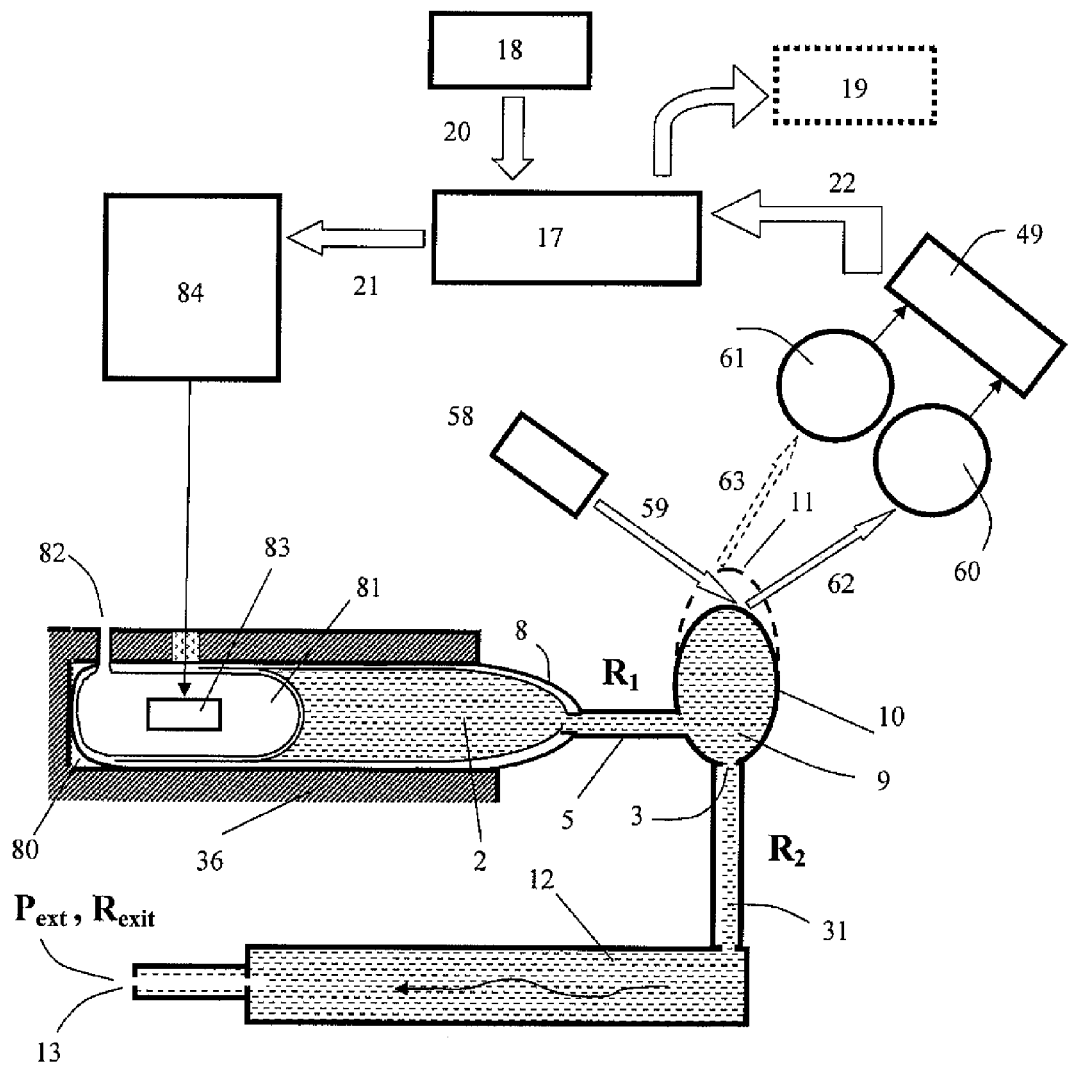
FIG. 21 depicts a schematic diagram of an additional embodiment having no electric motor, and differs from the one shown in FIG. 20 in that the fluid is forced to flow by controllable pressure of gas, such as air, located in the additional elastic bag which is situated inside the compression section of the reservoir.

The requirement of mutually cooperative construction relates also to the design of the section 8 which corresponds to the design of the means 14 responsible for an application of the squeezing-out force. The design of syringe-like section 8 made entirely of hard materials has been already discussed. As an alternative, certain elastic materials, for example a silicon rubber or similar which are easily compressible and/or expandable, can be used to design at least an internal part of the section 8 if the driving force system 14 is exploiting a thermo-pneumatic mechanism located inside the section 8 (FIG. 21). In contrast to that the external walls of the section 8 must be at least partially made of such easily deformable elastic material if the driving force system 14 comprises either a peristaltic mechanism (FIG. 22) or the thermo-pneumatic mechanism located in close proximity of said section 8 (FIG. 20). These examples demonstrate that embodiments of the present invention allow a wide choice of the materials to make the section 8 of the reservoir 1. Taking also into account what has been already said in previous paragraph, the conclusion is that the entire reservoir 1 of the invention always comprises at least one expandable element made of resilient material independently on whether resilient material is present in the section 8 or not.

In accordance with the present invention, another feature of the reservoir 1 is that during each delivery cycle the local volume of the fluid contained in each of two said sections 8 and 9 changes so much that the whole process of the fluid delivery can depend on said changes. The comparison of the scheme FIG. 3 with the simple example depicted in FIG. 2 helps to understand functional roles of each section. It can be desirable that typically the section 8 has relatively high volume exceeding the predetermined volume $D_0$ of a single dose at least few orders of magnitude. In order to raise the pressure in the reservoir 1 one needs to compress the fluid in the section 8 by any means 14 located either inside or outside of the section 8. That is why the section 8 may be called "compression section of the reservoir 1." When FIG. 2 and FIG. 3 are compared the only serious difference should be mentioned that while normal work real means 14 must be technical means instead of human's finger 4 shown in FIG. 2. However, in order to get increased reliability of the device in certain rare emergency cases even patient's finger 4 can be successfully used as temporary substitute of driving force system if technical means 14 fail due to any reason and control system informs a patient with either visual or acoustic emergency signal. Such emergency method is separately discussed in the very end of present description. Persons of ordinary skill in the art can appreciate that in order to make the fluid flow the compressing force produced by means 14 must affect a part of the surface of fluid's body. In this case the compressing force becomes the squeezing-out force. When such depending on time force is applied to the fluid in the section 8 the pressure $P_{comp}(t)$ in this section exceeds external pressure $P_{ext}$ affecting the fluid in the exit opening 13. Positive value of the expression $[P_{comp}(t)-P_{ext}]$ represents the excessive pressure which forces the fluid to flow out of the section 8 exactly as shown by middle image of FIG. 2. Obviously, this process decreases the volume of the fluid remaining in the compression section 8. For further aims it may be more convenient if said depending on time t excessive pressure in the compression section 8 is written in shorter form:

$$P_{comp}(t) - P_{ext} = \Delta P_{comp}(t) \quad \text{(Eq.3)}$$

Section 9 can play two functional roles. In accordance with the teaching of the invention, the first role of the expandable section 9 is to provide substantial change of its local volume in response to application of excessive pressure $\Delta P_{comp}(t)$ produced in the compression section 8 during each delivery cycle. In order to fulfill this function the fluid contained in the reservoir 1 makes contact with at least one elastic element 10 occupying at least some part of internal surface of the section 9. When positive excessive pressure $\Delta P_{comp}(t)$ is created in the fluid located in the compression section 8, this excessive pressure is first of all applied to the opened hydraulic communication, namely the element 5, and causes the transfer of some additional volume $\Delta V$ of the fluid from compression section 8 to the section 9. This transfer is accompanied by a certain increase of the pressure inside the section 9. Because the fluid in section 9 contacts with expandable element 10, the increased pressure deforms the element 10 and makes it expand so that the increase of the internal volume of the section 9 is equal to the additional volume $\Delta V$ of the fluid transferred from the compression section 8. This point is demonstrated by FIG. 3 wherein the non deformed element 10 is shown schematically by shadowed rectangle having the form of flat elastic membrane. Dashed curve 11 is to demonstrate the change of its shape and the increase $\Delta V$ of the volume of the section 9 caused by elevated pressure inside this section. Note that the flat membrane in FIG. 3 is provided as example only because it has been already demonstrated that actual shape of this expandable element 10 depends on chosen design which may vary in different embodiments.

It can be appreciated that resilient expansion of element 10 is accompanied by a corresponding change of at least one geometric parameter related to either the shape or certain characteristic size of this element. The said means that any change of said geometric parameter provides a direct indication of both the increase $\Delta V$ of the local volume of the section 9 and elevated pressure in whole reservoir 1. That is why the section 9 of the reservoir 1 should be further called by its full name "indicator section of the reservoir 1" or, for brevity, simply "the indicator." Moreover, that means that the fluid volume $\Delta V$ transferred from the compression section 8 to the indicator section 9 can be measured if the device is supplied with means, namely the sensor system 16, capable of producing signals associated with said at least one geometric parameter of the expandable element 10. The participation in such measurement is a role of the indicator section 9 of the reservoir 1. Due to this section is now named "the indicator," its internal volume at a particular time t, is to be further supplied with corresponding index and designated hereinafter as $V_{ind}(t)$. The corresponding change of this volume over time is designated as $\Delta V_{ind}(t) = V_{ind}(t) - V_0$ where $V_0$ is the local volume of non expanded indicator section 9 at initial fluid pressure equal $P_{ext}$.

Roles of the spatial separation of the compression section and the indicator section of the same reservoir can now be appreciated. Measurement of the volume change $\Delta V_{ind}(t)$ can be carried out correctly in the only case if deformation of the element 10 causing the volume expansion of the whole indicator section is caused only by the fluid. This means that said deformation must not be disturbed by direct involvement of the squeezing-out force provided by means 14. In order to avoid such direct involvement it may be desirable that: (i) means capable of changing over time the force squeezing the fluid out of the reservoir interact directly with only the first limited surface area of the fluid in the reservoir, actually the area located in the compression section, and (ii) said first area of the fluid is spatially separated from another limited surface area of the fluid, actually the limited area of the fluid located in the indicator section and brought into contact with such part of the expandable element 10 which is really involved in the measurement of the change $\Delta V_{ind}(t)$. This complicated sentence takes into account that resilient materials may be present in both the compression and the indicator sections, as shown for example in FIG. 7. However, only resilient deformation of this element is related to the indicator section, and in some cases only the deformation of certain part of the resilient elements related to the indicator sections, is capable of reflecting the change $\Delta V_{ind}(t)$. The word "reflecting" means that signals produced by the sensor system 16 in response of the change $\Delta V_{ind}(t)$ must not necessarily be proportional $\Delta V_{ind}(t)$. It may be quite enough if these signals are just associated somehow with at least one geometric parameter of such part of the expandable element 10 which is actually involved in the volume change $\Delta V_{ind}(t)$ of the indicator section. It is shown in the next section of the description that practical types of said involvements and said associations can vary in different embodiments. However, it should be appreciated that correctly done spatial separation of two sections of the reservoir discussed above may be enough to provide proper separation of two said areas of the fluid in the reservoir and, correspondingly, to exclude any possibility of undesirable direct involvement of means 14 in the formation of signals produced by the sensor system 16. Accordingly to what has been said above the correct spatial separation of two said sections of the reservoir 1 is such their separation, provided by means connecting these two section, that the first limited surface area of the fluid directly interacting with the squeezing-out force is fully located in the first section of the reservoir 1, and another limited surface area of the fluid contacting with said part of the expandable element 10 is fully located in the second section of the reservoir 1. When this condition is fulfilled said signals of the system 16 become capable of reflecting quantitatively actual physical properties of the hydraulic system independently on what particular means 14 are used and how they create the squeezing-out force.

The spatial separation of two said sections and corresponding spatial separation of two surface areas of the fluid's body are intentionally stressed in schematic view of FIG. 3 where compressing means 14 and 15 are located in close proximity of local cavity of the section 8 whereas the elastic element 10 is shown to belong only to local cavity of the section 9 of the reservoir 1. It has been already demonstrated that certain practical examples of said spatial separation may be sometimes less obvious and need to be analyzed carefully. However, two following considerations must be always taken into account: (i) said part of the expandable element 10 related to the indicator section has a resilient nature, and (ii) this part is deformed only by the difference of the fluid pressure $P_{ind}(t)$ inside the indicator and the external pressure $P_{ext}$ applied to the external surface of the element 10. These facts lead to following local relationship between the volume $V_{ind}(t)$ of the indicator 9 and its internal fluid's pressure $P_{ind}(t)$:

$$\alpha \Delta V_{ind}(t) = \alpha [V_{ind}(t) - V_0] = P_{ind}(t) - P_{ext} = \Delta P_{ind}(t) \quad \text{(Eq.4)}$$

where factor $\alpha$ is given stiffness factor of the indicator 9, and $\Delta P_{ind}(t)$ is the pressure difference in the indicator section 9 of the reservoir 1. Due to resilient nature of the element 10 the proportionality expressed by the equation (4) is always valid. However, it should be acknowledged by anyone skilled in the art that due to the presence of non-zero hydraulic resistance $R_1$ in the connection of two spatially separated sections of the reservoir 1 the dynamic relationships between excessive pressure $\Delta P_{comp}(t)$ in the compression section 8 and the responding changes of both the local volume $\Delta V_{ind}(t)$ of the indicator section 9 and its local pressure difference $\Delta P_{ind}(t)$ may be rather different in different embodiments. Particular types of these relationships are very important for the operation of whole device and will be thoroughly discussed later in many specific details.

It should be appreciated that in order to simplify the mathematical part of the present description, one can neglect very slight changes of the stiffness factor $\alpha$ while potentially substantial deformation of the expandable element 10 can occur. Similar slight changes are well known for all strongly deformed resilient materials and may require only certain small correction of the mathematical algorithm related to the method without any change of the general scope of the invention. This correction can be easily done while factory calibration of the device.

It has been mentioned before that the flow passage 12 comprises hydraulic resistor 31 providing non-zero resistance $R_2$. At the same time it should be appreciated by anyone skilled in the art that due to different reasons the actual output hydraulic resistance $R_{exit}$ of the device may increase accidentally in the process of the work. In the case of drug delivery devices it may happen from time-to-time because of either partial or insurmountable occlusion of the exit opening 13 brought in direct contact with patient's body. The output resistance $R_{exit}$ may also increase if the fluid flow carries hard microscopic contaminations, which may be delayed in certain narrow places of the hydraulic system like capillaries, too precise valves, and so on. The value $R_{exit}$ can increase also in the case of accidental damage of fine parts of the flow passage 12 occurring, for example, because of shaking of the device or any other kind of inaccurate usage. However, the said above means that actual output hydraulic resistance must be expressed as:

$$R_{exit} = R_2 + R_3 \geq R_2 \quad \text{(Eq.5)}$$

where additional resistance $R_3$ should be considered as an unpredictable external parameter that is either equal to zero (especially just after device manufacturing) or exceeds zero, let say after some aging of the device while its long-term work.

As far as particular designs of hydraulic systems are concerned their parts may be differently organized in different embodiments. In some cases it may be desirable to manufacture the reservoir 1 in the form of the syringe made of hard material and comprising two inseparable sections 8 and 9 where only resilient tube 10 of the indicator section 9 is made, for example, of soft silicon rubber (FIG. 4 and FIG. 5). It may be desirable in some embodiments that such tube is transparent for proper interaction of an optical sensor with fluid filling the indicator 9. In other embodiments it may be desirable that similar element 10 is covered with a thin layer 30 which does not influence the elasticity of the element 10 and simultaneously provides the surface with either high magnetization, or highly efficient light reflectivity, or an electric conductivity. If the reservoir 1 is made as irreplaceable syringe-like cartridge having piston 29 it may be desirable also that the driving shaft 15 connects the piston of said cartridge with the electromechanical system 14 so that both the syringe and its driving mechanism are inseparably fixed in their common housing 36 of the delivery device. In this case the cartridge must be supplied with additional port for periodic refilling with the fluid (not shown in FIG. 4 and FIG. 5).

An alternative approach may be desirable in other embodiments wherein only the compression section 8 of either replaceable or non replaceable cartridge is located in the housing 36 together with the system 14. The major part of the electronics, including the final part 16(*b*) of the sensor system 16 and/or the processor 17, can be deployed either in one housing 36 or in two housings 36 and 73 whichever is more convenient (see FIGS. 15, 16). The non-complete collection of parts deployed in one housing 36 or in both housing 36 and 73 can constitute only nothing but the separate programmable fluid supply device, meaning just a pump which is not capable yet of precise dosing the fluid because neither the indicator section 9 nor necessary elements of the flow passage 12 are contained in said housings of this separate device.

In this specific case the entire device of the invention can be formed only when such separate fluid supply device is further combined with an external exit port assembly having low size and shown in FIGS. 15, 16 not to scale as an example only. Such exit port assembly is located in separate small housing 74 containing as minimum number of parts as possible. The exit port assembly comprises the indicator section 9 supplied with at least one expandable element 10 made of resilient material. It further comprises means 12 connecting the indicator 9 with the exit opening 13 so that the hydraulic resistance of this connection is not less than predetermined non-zero value $R_2$. It is desirable also that the exit port assembly comprises at least one sensor element capable of producing signals associated with at least one geometric parameter of said expandable element 10. Actually, last sentence means that there is no need to place the entire sensor system 16 in the housing 74. This small housing may contain only such limited part 16(*a*) of the sensor system which needs to be inevitably located in close proximity of the expandable indicator 9. Obviously, the signals produced by this limited part 16(*a*) have to be further transmitted by certain means (see the arrow 22 in FIGS. 15, 16 for example) to the rest of the electronics, represented for example by the remaining part 16(b) of the sensor system, located in housings of said separate fluid supply device.

The combination of the small exit port assembly with said fluid supply device assumes that both sections 8 and 9 located in different housings 36 and 74 correspondingly are connected in order to form the entire device. This connection can be provided by hydraulic means comprising both the resistor 5 and the tube 75 which may be as long as necessary (FIG. 15). At least part of said connecting means is included in the design of the exit port assembly. The exact location of the resistor 5 is not too much critical for the functioning of the combination of the exit port assembly and said fluid supply device. However, it is typically more desirable that the resistor 5 providing predetermined non-zero resistance $R_1$ and representing at least part of said connecting means, is located within the housing 74 because in this case the precision of the assembled fluid delivery device does not depend on the length and expandability of the tube 75 made preferably of flexible plastic materials. The ratio $R_1/R_2$ should desirably correspond to the same requirements which have been already disclosed above. In addition it may be noted that in some embodiments the electric wires can be embedded into the wall of the same plastic tube 75 connecting housings 36 and 74 in order to provide the exit port assembly with both the electric power and most simple means transmitting the signals to electronic part 16(b) as shown by the arrow 22 in FIG. 16. At the same time it may be apparent there is no need to use wires if the exit port assembly is supplied with internal batteries and wireless transmitting means.

The main advantage of the exit port assembly formally separated from a programmable fluid supply device is that the full volume of such exit port assembly can be made below about 1 cm³. Such a small appliance may be conveniently deployed at many points on the patient's skin, or even implanted into his or her body if necessary. Especially in the last case it may be desirable that means hydraulically connecting the section 9 of the exit port assembly with the section 8 of the fluid supply device comprise the connector 87 (see FIG. 16), capable of both connecting and disconnecting said device when it is prescribed by medical or technical requirements. This connector is destined to remain outside the patient's body if the exit port assembly is fully implanted inside it. Small exit port assembly supplied with means transmitting the signals wirelessly may be extremely useful for special group of patients such as, for example, little children which need to be controlled by parents or experienced medical staff.

One more feature of the invention is that in some embodiments developed specifically for ambulatory drug delivery, the entire hydraulic system can be made in the form of very simple, low cost factory pre-filled replaceable cartridge. In some embodiments, it can be fully disposable, which eliminates the necessity of manual refilling by unskillful users. Being filled with the liquid drug by a manufacturer, such cartridges can be made free of air bubbles and potential contaminants, and can satisfy sterility requirements. It can be desirable that in order to be as simple and cheap as possible the replaceable cartridge does not contain either complicated or high precision parts of the sensor system 16 and/or squeezing-out system 14. It is anticipated that, in order to activate the replaceable cartridge of the invention, the user should only insert the installable part of the cartridge into the corresponding place of the housing of the device, and then fix the cartridge by closing the lid of the housing.

It should be appreciated that different designs of replaceable cartridges may be used in different embodiments, and simple particular designs may be particularly desired. However, independently on possible individual constructive variations, any replaceable cartridge of the invention desirably possesses one or more of the common features listed below. Namely, a such cartridge comprises: (i) certain means designed to provide stable location of the installable part of the cartridge in the housing of the device; (ii) a reservoir comprising at least one expandable element made of resilient material and situated so that after the installation of the cartridge this expandable element takes a position in a proximity of at least one element of a sensor system of the device; (iii) means connecting the reservoir with at least one exit opening so that a hydraulic resistance of this connection is not less than predetermined non-zero value $R_2$; and (iv) a fluid pre-filling the reservoir so that the fluid in both the reservoir and any part of said means connecting the reservoir with the exit opening is subjected to the same pressure which is close to an external pressure. The last condition (iv) stresses that the fluid placed into the cartridge does not need to be kept under high excessive pressure. However, initial pressure inside the cartridge may exceed external one a little bit which is only intended to avoid the formation of air bubble while connecting the exit opening of the cartridge with patient's body.

Figure 6:
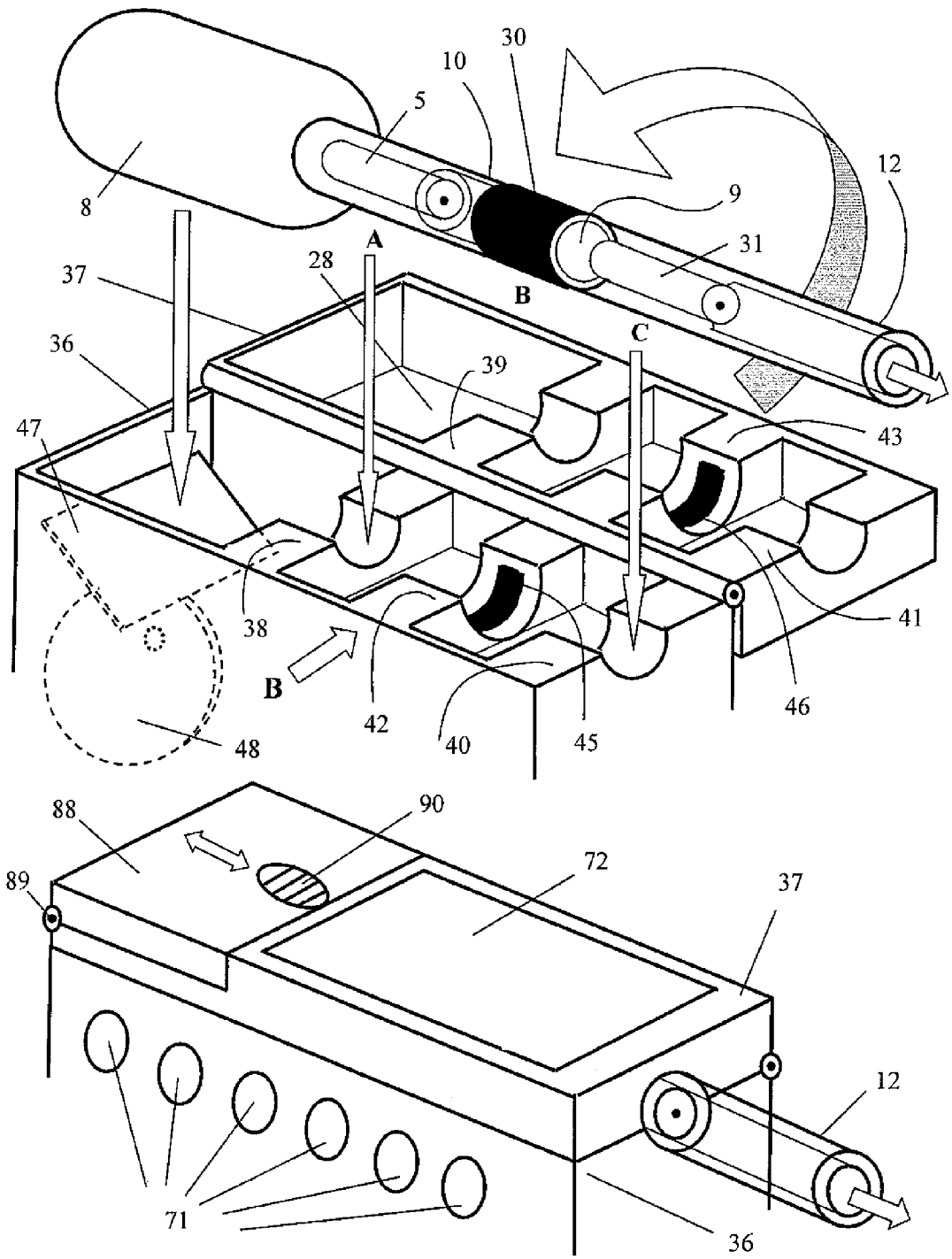
FIG. 6 depicts the general view of a replaceable cartridge of the invention having both compression and indicator sections of the reservoir made of transparent resilient silicon rubber. The top view shows how the cartridge may be installed when the lid of the housing is open. The bottom view shows the housing having closed lid after the installation of the cartridge.
Figure 7:
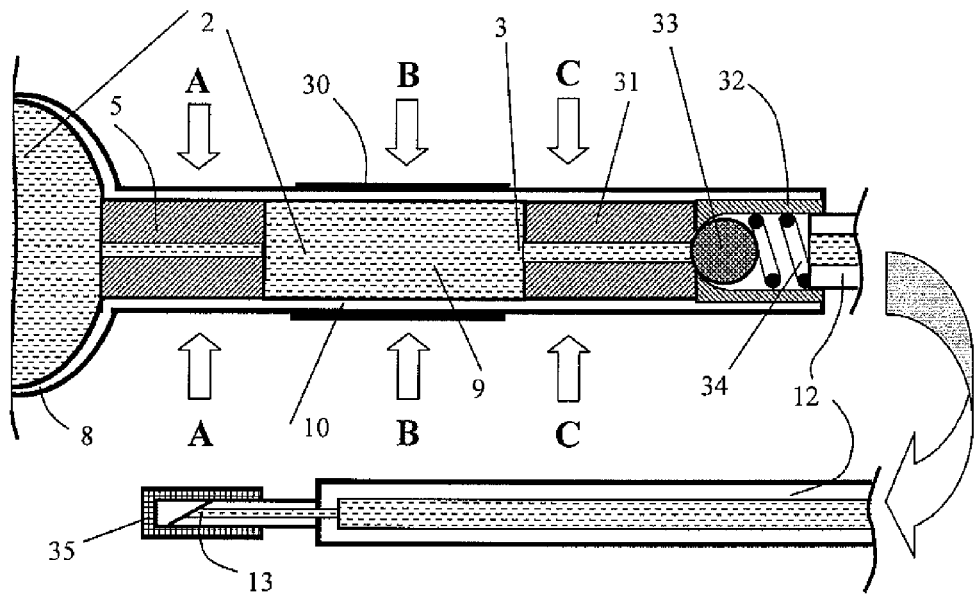
FIG. 7 depicts a parts of a replaceable cartridge of this invention pre-filled with a fluid.

The top view of FIG. 6 demonstrates schematically how the points mentioned in previous paragraph can be realized in certain particular embodiment which relates to the group of more desirable embodiments of the invention. This top view shows the situation before the installation of the replaceable cartridge, when the housing 36 is empty and its lid 37 is opened. The view of non installed cartridge is shown above the housing, and three thick arrows directed down show exact places where corresponding parts of the cartridge must be fixed after the installation. Except for a few small parts, the major body of the replaceable cartridge corresponding to this example is made of soft elastic material, preferably silicon rubber or alike. A cross-section of parts of the same cartridge is shown also in FIG. 7. The cartridge comprises relatively big section 8 made in the form of elastic bag or elastic pillow pre-filled with the fluid at low pressure which is about the same as an external pressure. The section 8 is inseparably connected with long transparent elastic tube 10 having thin wall and made of the same elastic material. The entire reservoir 1 consists of the bag 8 and two sections of said tube 10, namely "A" and "B". The section "B" is a hollow short piece of the tube that represents the indicator section 9 of the reservoir. In order to connect the bag 8 and the indicator 9, the section "A" contains a resistor 5 made of hard material like a metal or ceramic embedded into the tube. Small diameter channel in the center of the resistor 5 provides it with a property of capillary-like static hydraulic resistors having predetermined resistance $R_1$. The cavity "B" of the indicator section 9 is limited by resilient wall of the tube 10 and the resistor 5 on one side. The opposite side of the indicator 9 is limited by the second cylinder 31 embedded into the section "C" of the tube. Resistor 31 is made similar to the hydraulic resistor 5 except the length and the diameter of the capillary-like channel of the cylinder 31 is chosen so that this element provides a predetermined resistance $R_2$ representing the beginning of the flow passage 12. FIG. 7 shows that the end of the flow passage may contain sharp needle where the exit opening 13 is closed temporarily by hermetic cap 35 to preserve sterility conditions before the installation of the cartridge.

Figure 8:
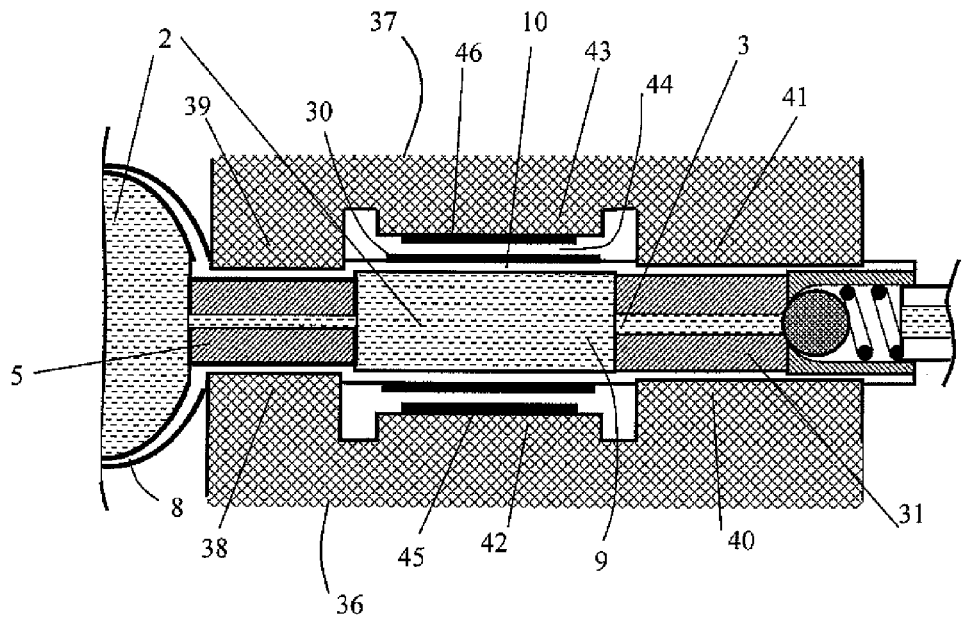
FIG. 8 depicts a cross-section of the replaceable cartridge as shown in FIG. 7 fixed inside the housing.
Figure 12:
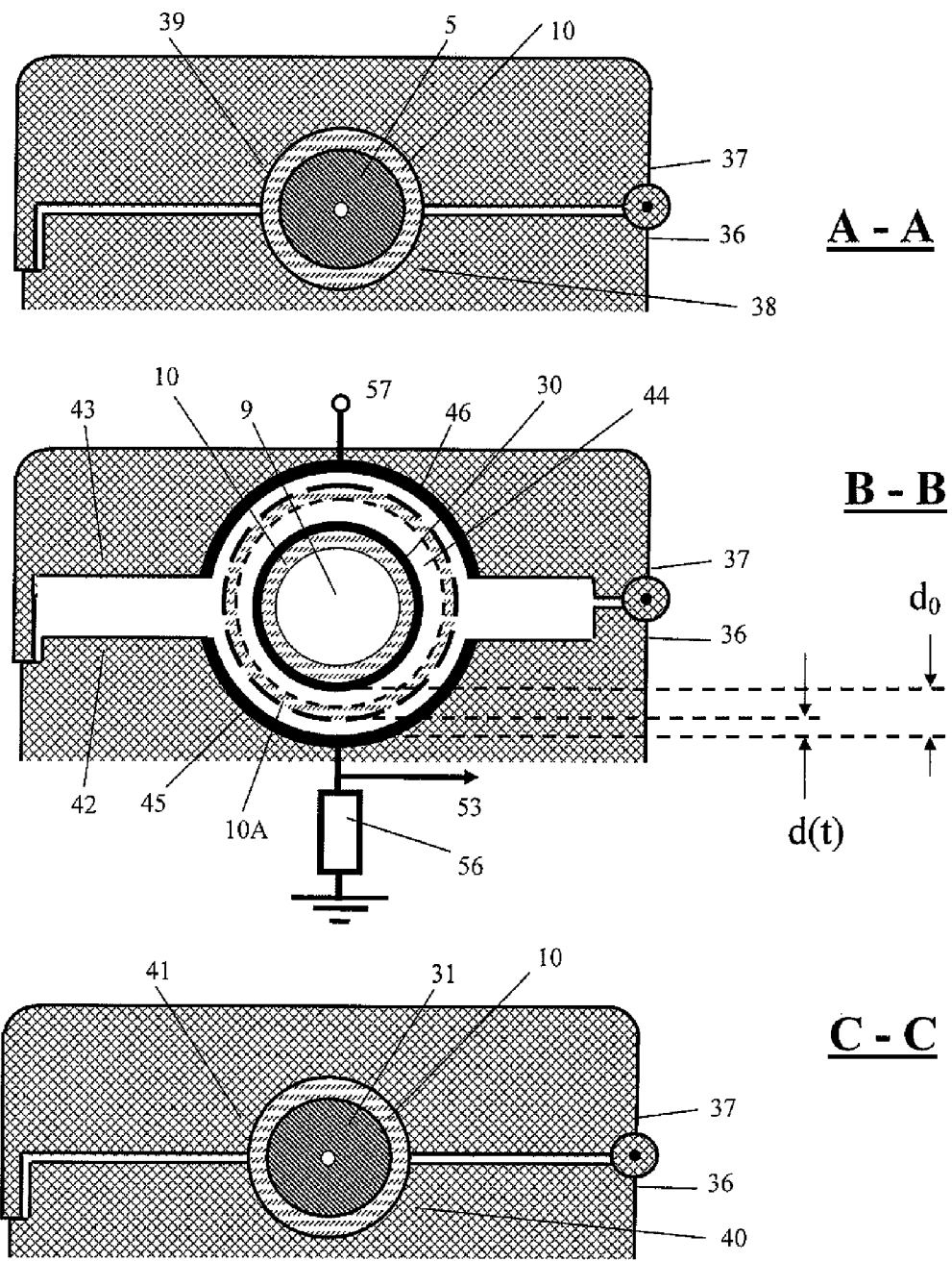
FIG. 12 depicts an example of the invention having a non-contact capacitor sensor combined with a replaceable cartridge shown in FIG. 7 where freely moving external surface of elastic indicator's tube contains an electrically conducting layer (cross-section "B-B"). Views "A-A" and "C-C" correspond to cross-sections of the same cartridge fixed by ribs of both main part of the housing and its closed lid.

It should be appreciated that external surfaces of both cylinders 5 and 31 can be used for reliable fixing the cartridge in the housing because both cylinders are made of hard materials. In order to fix both cylinders the main housing 36 and its lid 37 have a couple ribs 38 and 39 corresponding to the section "A" of the tube, and also they have another couple ribs 40 and 41 corresponding to the section "C". Each pair of ribs has a form and size that closed lid 37 causes two opposite ribs to compress the thin rubber layer on the surface of cylinders. Friction of the compressed rubber helps to fix both cylinders firmly. When the lid 37 is closed and both cylinders and 31 are fixed, the position of the expandable section "B" of the tube 10 located between 5 and 31 becomes stabilized as well (see FIG. 8 and FIG. 12). However, it should be appreciated that at closed lid 37 the ribs 42 and 43 do not compress the section "B" of the tube 10. Both FIG. 8 and FIG. 12 depict the narrow gap 44 between the surface of the section "B" of the tube 10 and the broken circle formed by hard surfaces of ribs 42 and 43. This gap permits free resilient expansion of the internal volume of the indicator 9. Roles of thin ring-like layer 30 covering the section 9 and two half-ring stripes 45 and 46 fixed on corresponding ribs of the housing 36 and its lid 37 will be discussed herein below. Here it is relevant only to note that stripes 45 and 46 are input elements of sensor system 16. It is shown in FIG. 8 and FIG. 12 that after the installation of the replaceable cartridge the surface of its section 9 gets the position in close proximity of these input elements as it is required.

Figure 22:
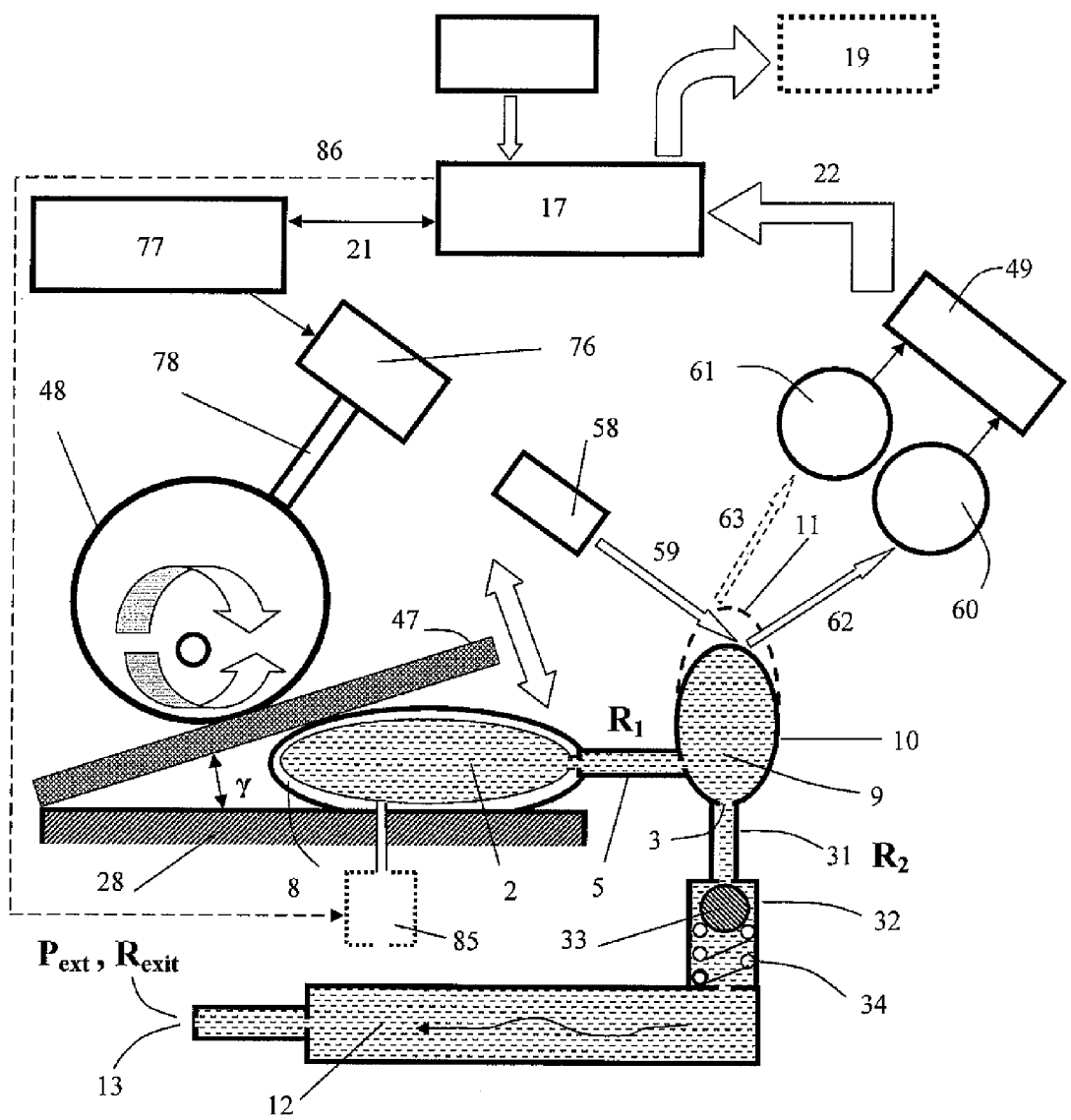
FIG. 22 depicts schematically another embodiment of the invention wherein the flow passage is connected with an expandable indicator section of the reservoir and also comprises a passive valve controlled only by the pressure drop between its ends (more details are shown in FIG. 7). An electro-mechanical driving force system shown herein is capable of producing quasi-rectangular pressure pulses in the resilient compression section of the reservoir.

One more feature of this particular example of the replaceable cartridge is that after the lid 37 is closed the elastic bag 8 is captured in the cavity formed between immovable plate 28 of the lid 37 and movable part 47 of the system 14 which is located in the housing 36 and capable of applying the squeezing-out force according to a mechanism shown in FIG. 22. Therefore, it follows from the above that in order to install the replaceable cartridge one needs only to drop it down into the housing 36 accordingly to three thick vertical arrows in FIG. 6, and then the lid 37 is to be closed by rotating it counter-clockwise in the direction shown with thick rounded arrow. After that the entire reservoir 1 of the replaceable cartridge is stabilized inside the housing 36, and only final part of the flow passage 12 goes outside in order to be connected with patient's body as shown in bottom view of FIG. 6. In order to begin the fluid delivery with new replaceable cartridge installed, one needs only to remove hermetic cap 35 preserving the sterility of factory pre-filled cartridge.

It may be appreciated by anyone skilled in the art that other designs of simple, low cost, fully disposable cartridges are possible as well based on the approach similar to the one disclosed above. For example, the factory pre-filled disposable cartridge may be formally subdivided in two hydraulically communicating parts in accordance with the hydraulic scheme shown in FIG. 15. In this case such cartridge comprises the compression section 8 made of appropriate elastic material and supplied with specially designed means in order to fix only this section in the housing 36 together with squeezing-out means 14, and further the cartridge comprises the long flexible tube 75 connecting the section 8 with the disposable exit port assembly located in the separate housing and having rather simple construction which has been already described above. Moreover, it will be explained later how and why the invention can work very well even with low precision squeezing-out means 14. Taking this into account it may be also appreciated if the compression section 8 of fully disposable cartridge is represented by syringe-like simple part satisfying only very modest technical requirements.

Everything what has been said before in regard of means connecting the reservoir 1 with the exit opening 13 relates preferably to embodiments, independently of whether the replaceable cartridge is used or not. However, said connecting means, called also the flow passage 12, may be further improved. To achieve that, it may be desirable that the flow passage 12 further comprises the element, which in accordance with the definition No. 2, is considered as a pressure-dependent static hydraulic resistor capable of switching its resistance accordingly to pressure drop applied to this resistor. It may be desirable that this pressure-dependent resistor exhibits non linear dependence of the intensity of the fluid flow F upon the pressure drop $\Delta\pi$ as shown in FIG. 9 (a). Technically this type of the dependence $F(\Delta\pi)$ can be realized by the passive valve 32 shown in FIG. 7 as an optional element of any replaceable cartridge, or shown in FIG. 22 as an inevitable element of any most desirable embodiment. The difference between characteristics of passive non-linear valve 32 and other linear hydraulic elements, such as static resistors 5 and 31, is easily seen from FIG. 9 where strait line (b) serves as the example of typically desirable characteristics of the resistor 5, line (c) is the example of typically desirable characteristics of the resistor 31. Dashed curve (a) in FIG. 9 shows that the valve 32 remains closed if the pressure drop $\Delta\pi$ applied to its ends is negative or less than calibrated value $P_{val}$. At a positive pressure drop a little bit more than $P_{val}$ the valve 32 becomes open and provides rather low hydraulic resistance. It may be obvious for those skilled in the art that the non-linear hydraulic characteristics shown in FIG. 9 (a) can be provided by variety of different passive valves, and particular details of present valve 32, namely the ball 33 and calibrated spring 34 (see FIG. 7), should be considered as an example only.

In other embodiments of present invention the valve 32 is destined to fulfill two different functions which are combined in the same design. First, this valve can prevent even low undesirable leakage of the fluid from the exit opening 13 in unlikely case if after the end of the fluid delivery cycle the reservoir 1 remains subjected to some low residual pressure which does not exceed $P_{val}$. The second function of the valve 32 is to provide highly stable internal standard of the switching pressure point $P_{val}$ based on high mechanical stability of calibrated spring 34. This internal standard is used by discussed later most advanced mathematical algorithm of the invention in order to provide automatic self-calibration and self-control of all critically important systems of whole device. Both these functions can be fulfilled successfully if quantitative relationship of the predetermined value $R_2$ and the hydraulic resistance $R_{val}$ of the valve 32 satisfies at least following requirements: (i) $R_2$ exceeds $R_{val}$, and more preferably $R_2$ exceeds $R_{val}$ at least one order of magnitude when a pressure drop applied to said pressure-dependent valve is more than predetermined value $P_{val}$; (ii) in the opposite case the resistance $R_{val}$ exceeds $R_2$, more desirably $R_{val}$ exceeds $R_2$ at least one order of magnitude, and most desirable $R_{val}$ exceeds $R_2$ more than two orders of magnitude when said pressure drop is less than said $P_{val}$.

B. Sensor System

A purpose of the sensor system 16 shown in FIG. 3 schematically is to transform certain appropriate geometric parameter associated with either entire local internal volume $V_{ind}(t)$ of the indicator section 9 of the reservoir 1 or time-dependent change $\Delta V_{ind}(t)$ of the same volume into corresponding output signals which are to be transferred to programmable processor 17 for further treatment (see arrow 22 in FIG. 3). It has been already demonstrated that the volume expansion of the indicator section cannot be separated from the deformation of its expandable element 10 and, correspondingly, output signals of the sensor system 16 are always associated somehow with certain geometric parameter of said expandable element 10. Examples of many different sensors provided below show how said appropriate geometric parameter can be chosen and used in each particular case. However, independently on what particular physical principle is exploited by the sensor, there are few features which are common for all sensor systems of the invention. The first common feature is that every sensor system 16 comprises at least one input sensing element which: (i) must be located in proximity of the expandable indicator section 9 of the reservoir 1, and (ii) is directly involved in producing analog input signals of the sensor system 16, said analog input signals are associated with at least one geometric parameter of the expandable element 10 of the indicator 9. The second common feature is that every sensor system 16 comprises a transducer 49 (see, for example, FIGS. 19, 20, 21, 22) which (i) transforms said analog input signals into the output signals and (ii) transmits these output signals to the processor. Typically the transformation of analog input signals is performed by standard microelectronics which may include either amplifiers or/and differential amplifiers, high frequency generators, analog-to-digit converters, and/or many other standard electronic appliances which do not require special disclosure. The only obvious and inevitable requirement is that an electronic format of said output signals produced by the system 16 must correspond to the format of the input signals of the processor 17.

It should be appreciated that independently on physical form of output signals both analog input signals and said output signals contain the same information related to the primary physical process $\Delta V_{ind}(t)$. The physical form of output signals can be chosen according to the kind of electronic processor 17 treating this information. In principle, certain simple algorithms of mathematical treatment of the information, for example integration of signals, can be realized by very traditional analog electronics. Correspondingly, in some embodiments the output signals of the system 16 may be analog ones if they are intended to be treated by corresponding analog processor 17. However, for better precision of whole delivery device it may be desirable that the sensor system 16 produces digital output signals reflecting either $V_{ind}(t)$ or $\Delta V_{ind}(t)$ so that any of these variables, represented by said output signals in digital form, can be treated by more contemporary digital processors. It can also be desirable and can be easily achieved with contemporary analog-to-digit transducers 49 whereby input analog signals of the system 16 are converted to digital output signals with the precision of at least about 0.1% of full range of analog input signals. It may be even more desirable that said analog-to-digit converting occurs with the precision about 0.01% by the order of magnitude.

However, the present invention doesn't depend on the physical form of the output signals. Also it doesn't depend on what electronic means are used to transform said analog input signals of the sensor and further deliver the information contained in these signals to said processor. For example, in some cases it may be convenient to transmit output signals to the processor by wires only, especially if whole device is assembled in the only housing comprising both the processor 17 and the entire sensor system 16. In other embodiments comprising two separate housings or more, it may be more appropriate if the entire sensor system 16 is subdivided in two or more parts. For example, first input part 16(*a*) may comprise input sensing elements and a primary transducer 49(*a*), whereas a second output part 16(*b*) may comprise a secondary transducer 49(*b*) so that each transducer is located in its own separate housing, for example, 36 and either 73 or 74, respectively, as shown in FIGS. 15, 16. The primary transducer 49(*a*) is capable of transforming said analog input signals to certain another signals which are intermediate signals also associated somehow with said analog input signals.

Also FIG. 16 shows that the primary transducer 49(*a*) located in the housing 74 comprises certain means 67 capable of transmitting said intermediate signals to the another separate housing 36 comprising means 68 capable of receiving said transmitted signals. It should be appreciated that even in this case wires can be sometimes used to transmit signals from 16(*a*) to 16(*b*) and further to the processor 17. In other cases it may be more convenient for customers and/or manufacturer if such transmitting of signals is provided wirelessly by either radio waves or pulses of infrared light. In the last case of wireless communication the input part 16(*a*) must be supplied with wireless transmitter 67, and the output part 16(*b*) must be supplied with corresponding wireless receiver 68.

Another feature of the invention is how analog input signals can be produced. It should be appreciated by anyone skilled in the art that at least one sensing element of the input circuitry of the system 16 must physically interact with such at least one part of the indicator 9 which is capable of changing its at least one geometric parameter simultaneously with physical changes $\Delta V_{ind}(t)$. In FIG. 3 double directed arrow 23 depicts such interaction schematically. There are many different physical types of interactions which may be successfully used within the scope of the invention. The examples of such interactions are: (i) mechanical or electro-mechanical interaction of certain parts of the indicator 9 with at least one sensing element providing the analog input signals of the sensor system 16, (ii) interactions involving electric or magnetic fields, (iii) interactions using light beams, and so on. In the present description attention is focused on specific ways of the formation of analog input electric signals directly produced by sensing input elements of a corresponding sensor. Due to the geometry of the elastic element 10 of the indicator 9 is chosen to be the primary parameter of the sensor (see the definition No. 7) it should be apparent that both the indicator section 9 of the reservoir 1 and said at least one sensing input element of the sensor system 16 are desirably fixed relative to each other so that only changes of the geometry of the element 10 are permitted to cause corresponding changes of the sensor's analog input signals.

Thus, taking into account multiple types of different physical interactions applicable to the sensor system 16, there is no possibility to make the only choice of specific sensor's name based on physical nature of any particular interaction. At the same time it should be further appreciated by anyone skilled in the art that, independently on particular type of said interaction used for the creation of primary analog signals, any such primary analog signal always changes in either direct or indirect association with the change of at least one geometric parameter of elastic element 10 of the reservoir 1, and only this geometric change corresponds directly to time-dependent volume change $\Delta V_{ind}(t)$. That is a reason why in accordance with the definition No. 7 an acceptable primary physical parameter of sensor systems of the present invention is a certain geometric parameter related either directly or indirectly to either the size or the shape of at least one expandable element of the reservoir 1. Correspondingly, the general name of all sensors of the invention should be the following: "Sensor capable of producing signals associated with at least one geometric parameter of the expandable element of the reservoir." Wide applicability of this definition to all sensors of the invention follows from examples below.

FIG. 10 depicts an example of a sensor wherein at least one such element of the sensor system 16, which is directly involved in producing of the analog input signals, is a piezo-electric element 50 located either in the housing 36 or 74 in certain proximity of expandable section 9 of the reservoir 1 filled with the fluid 2. One end of the element 50 is fixed in said housing whereas its opposite end is brought into either direct or indirect mechanical contact with external surface of the indicator 9 made entirely of the metal. For example, this type of fully metallic indicator combined with the piezoelectric sensor can be used as the part of the exit port assembly discussed before (see FIG. 15 or FIG. 16). FIG. 10 shows that in this particular case the metallic disk 51 forms the external surface of the indicator 9 capable of relocating in the process of indicator's expansion. The disk 51 is supplied with intermediate tip which defines the exact point of the mechanical interaction with piezoelectric element 50. Desirable variability of the indicator's internal volume is provided by short resilient sylphon bellows 10, connecting movable disk 51 hermetically with immovable hard walls of the indicator 9. In order to establish reliable mechanical contact with piezoelectric element 50 the immovable part of the indicator 9 is also fixed in the housing so that at low initial pressure of the fluid the resilient bellows 10 is slightly compressed. Any positive or negative change of the fluid pressure inside the indicator makes the disk 51 to move (it is shown with double directed arrow). This movement results simultaneously in: (i) the change of the shape of elastic bellows 10, (ii) the change $\Delta V_{ind}(t)$ of internal volume of the indicator 9 caused by the change $\Delta P_{ind}(t)$ of its internal pressure, and (iii) the deformation change of piezoelectric element 50. In response to all these changes the element 50 produces the change $\Delta U(t)$ of input voltage which is further transferred to either the primary transducer 49(a) or entire transducer 49 by the grounding wire 52 and the signal wire 53. Thus, in this example transducer's output signal S(t) is always associated with geometric parameter characterizing the expansion of the sylphon bellows 10 which represents the resilient part of the reservoir entirely made of the metal. One can see obviously that in this particular example said geometric parameter associated with output signals S(t) is the curvature radius of the sylphon bellows.

It can be appreciated that the example shown in FIG. 10 may be desirable for such fluid delivery devices where the expandable indicator 9 of the reservoir 1 and the piezoelectric element 50 are fixed inseparably, because the whole sensor requires high precision fixation of their positions in the housing. That is why this type of sensors can be suitable for devices supplied with non-replaceable cartridges.

It may be appreciated by anyone skilled in the art that in certain cases the output signal of properly designed transducer depends linearly on its input signal reflecting changes of both $\Delta V_{ind}$ and $\Delta P_{ind}$. One can express such linear dependence with the use of certain constant factor β which reflects the inverse sensitivity:

$$\beta S(t) = \Delta V_{ind}(t) = [V_{ind}(t) - V_0] = [P_{ind}(t) - P_{ext}]/\alpha = \Delta P_{ind}(t)/\alpha \qquad (Eq.6)$$

where the equation (4) has been also used to express the relationship between S(t) and $\Delta P_{ind}(t)$. It is desirable that simple linear equation (6) is equally applicable to all examples of the sensor system 16 provided hereinafter. Minor deviation from actual linearity, which may happen in some practical devices, can be further easily corrected by corresponding algorithm of the programmable processor.

A second example shown in FIG. 11 does not require so high precision of the fixing of the indicator 9 relatively the position of input sensing elements of the sensor system 16. This example represents non contact capacitor sensor wherein the metallic indicator 9 is practically the same as in FIG. 10, and its immovable part is fixed in the housing. Two electrically conducting metallic plates 54 and 55 are also fixed on insulating support of the same housing 36 so that the partial capacitance formed by only plates 54 and 55 is low. The wire 57 connects the plate 54 with the AC generator of the transducer 49 of this particular sensor system. It is desirable that said AC voltage applied to the plate 54 is stable enough in regard of both the frequency and its amplitude. At the same time the plate 55 is the only sensing element which is connected with the main input circuitry of the transducer by the wire 53 grounded by an input resistor 56. Simple equivalent electric diagram of the input circuitry is shown with dashed lines in the top right corner of FIG. 11. Accordingly to this diagram the AC voltage of the plate 55 depends on the capacitance $C_1$ existing between the plate 54 and the only sensing plate 55 when capable of relocating metallic disk 51 makes relatively high contribution into this capacitance.

In order to obtain good sensitivity of such sensor system, the movable part of the indicator 9, namely the disk 51, should be located in proximity to both plates 54 and 55 so that narrow gap 44 is formed between electrically conducting disk 51 and two conducting plates 54 and 55 as shown in FIG. 11. Due to the disk 51 is capable of relocating accordingly to the deformation of the sylphon bellows 10, the gap 44 is a variable depending on the curvature radius of the sylphon bellows 10. It should be appreciated by anyone skilled in the art that due to electrically conducting area of movable metallic disk 51 overlaps widely with electrically conducting areas of fixed plates 54 and 55, the variable gap 44 depending on the state of the internal volume of the indicator 9 makes the main contribution in variable capacitance $C_1$ between fixed plates 54 and 55. Consequently, the change $\Delta V_{ind}(t)$ associated with the change of curvature radius of the sylphon bellows 10 provides the change of the gap 44, resulting in corresponding change of the capacitance $C_1$ which leads to amplitude change of AC analog input signal produced by the plate 55. The transducer 49 measures this amplitude and produces corresponding digital output signals. This long chain of dependencies explains why and how the output signals of the sensor system 16 are associated with the geometric parameter of the sylphon bellows 10, namely with variable curvature radius of the sylphon bellows 10.

It can be appreciated that the absence of direct mechanical interactions in the non contact capacitor sensor depicted in FIG. 11 makes this type of sensors well compatible with replaceable cartridges. For example, if the AC frequency is about 1 MHz or more, and the area of the overlapping of the disk 51 with fixed plates 54 and 55 is about 1 $cm^2$ then analog input signals are well measurable even if the gap 44 varies in quite reasonable range between about 0.1 mm and 0.3 mm. Correspondingly, every time when the replaceable indicator section of the reservoir 1 is fixed in the housing, this fixing can be done with relatively low precision about 0.05 mm. In this case the variation of the gap's width influences only the sensitivity but the system 16 as such keeps its ability of producing proper signals. It will be shown later that algorithms of most advanced devices of the invention are capable of self-calibrating the sensitivity so that no additional trouble occurs for unskillful users. In addition it is necessary to stress that shown in FIG. 11 electric diagram of capacitance measurement is provided as simplest example only. Those skilled in the art may know that other measurement schemes can be used as well, for example, more complex capacitance bridge provides much better precision and higher sensitivity.

It may be desirable in some embodiments that at least one element of the sensor system, which is directly involved in producing of analog input signals, comprises a magnetic detector fixed within the housing. Magnetic detector is capable of forming non contact magnetic sensor if said detector is fixed in proximity of magnetized substance which is attached to any such part of the indicator section 9 of the reservoir which is capable of the relocation accordingly to the deformation of its expandable element 10. For example, magnetized substance can be attached to the surface of movable disk 51 considered before, or whole disk can be made of constantly magnetized metal. In this case high precision measurements associated with at least one geometric parameter of the expandable element 10 can be done with magnetic sensor. Due to such type of non contact sensors is well known there is no need to discuss its details here.

Further example shown in FIG. 12 demonstrates how non contact capacitor sensor may be formed in most desirable case where fully replaceable cartridge shown in FIG. 6, FIG. 7, and FIG. 8 comprises indicator 9 having tube-like elastic wall 10 made, for example, of silicon rubber. In this particular example the short piece of external surface of elastic wall 10, corresponding to the indicator section "B", is covered with thin conducting layer 30 made, for example, of graphite powder embedded into silicon rubber or certain electrically conducting polymers which do not influence the elasticity of the tube 10. At the same time the section "B" of the housing 36 contains electrically conducting half-rings 45 and 46 located on insulating ribs 42 and 43 correspondingly. If the cartridge is installed into the housing 36 (see FIG. 6) and its lid 37 is closed the indicator's part of the cartridge takes the position shown in cross-section "B-B" of FIG. 12. Both conducting half-rings 45 and 46 are situated coaxially with conducting cylindrical layer 30 and form the variable cylindrical capacitor which is electrically similar to what has been disclosed previously in FIG. 11. As before, the value of the capacitance $C_1$ depends on the width of the gap 44 between conducting surface 30 of the section "B" of resilient tube 10 and both half-rings 45 and 46. At low initial fluid pressure the capacitance is low as well because gap's value $d_0$ is relatively high. Any increase of fluid pressure $P_{ind}(t)$ inside the indicator 9 causes the expansion of its internal volume $V_{ind}(t)$ and the change of external radius of both the tube 10 and electrically conducting layer 30. In FIG. 12 dashed circle 10A having increased external radius demonstrates the transition from initial shape of the tube 10 to its expanded shape. This expansion leads to decreased gap d(t) resulting in increased capacitance measured by the transducer 49 and transformed into output signals of the sensor system 16. Thus, in this particular example said output signals are associated with such active geometric parameter of the expandable element 10 which is the width of variable gap 44 depending on the external radius of the elastic tube.

One can note that shown in FIG. 12 middle section "B" related to the indicator 9 is suspended between sections "A" and "C" fixed reliably by compressed ribs of the housing (see also FIGS. 6, 7 and 8). Due to this suspension the axis of the elastic section "B" can only fluctuate near its central position. However, it should be appreciated that coaxial construction of non contact capacitor sensor shown in FIG. 12 is much more preferable than the construction of FIG. 11, because the coaxial design of the variable capacitor eliminates the high frequency noise of the sensor system related to accidental elastic displacement of the section "B" of the tube 10 caused by vibrations of the device, accidental strikes while transportation, and so on.

Figure 13:
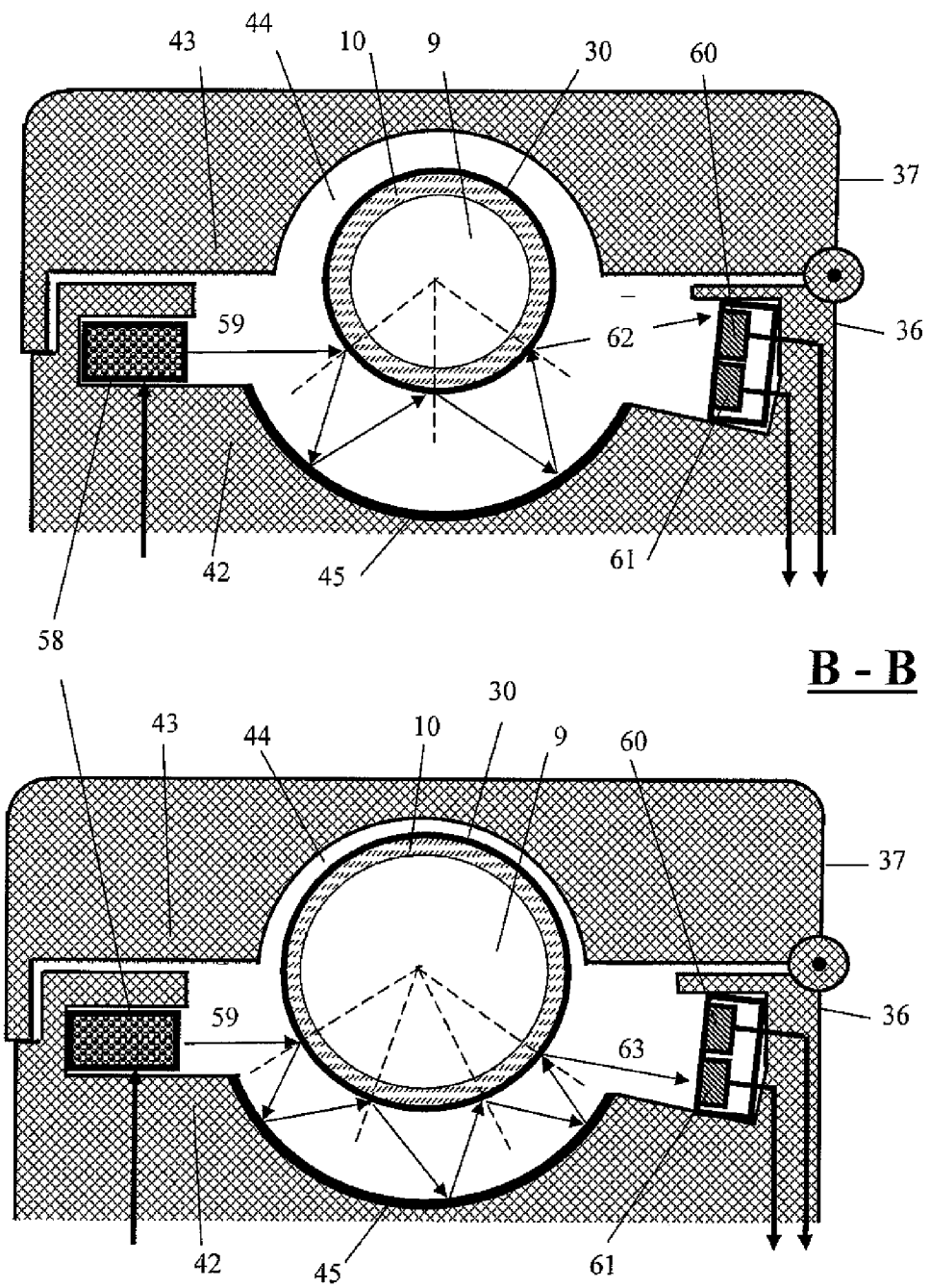
FIG. 13 depicts an example of the invention having a non-contact optical sensor combined with a replaceable cartridge as shown in FIG. 7, where both housing and freely moving external surface of an elastic indicator's tube are capable of reflecting light. Top and bottom views show corresponding directions of a light beam at either low and high pressure within the indicator.

Non contact sensors of the invention can also exploit certain optic features of the indicator section of the reservoir 1. FIG. 13 represents further example of such non contact optical part of the sensor system which is directly involved in producing analog input signals associated with the changes of at least one geometric parameter of elastic tube 10 which is a part of reservoir 1 of either replaceable or non replaceable cartridge. (It is assumed in FIG. 13 that such cartridge is already installed within the housing and both sections "A" and "C" are fixed similar to what is shown in FIG. 12. For visual aids dashed lines corresponding to radii of the section "B" of the tube are provided). This sensor comprises source 58 (for example, a low intensity semiconductor laser) of primary light beam 59 directed onto the section "B" of the reservoir. Also the sensor comprises at least one photo-detector of reflected light, and more desirably it comprises at lest two such photo-detectors 60 and 61, all fixed in the housing 36. In contrast to previous sensor, half-ring 45 fixed on the rib 42 is capable of reflecting the light as a mirror. Also the section "B" of the elastic tube 10 comprises very thin surface layer 30, which is capable of reflecting the light like a mirror and does not influence the elasticity of the tube. It may be also desirable that output signal of the transducer 49 is proportional to the difference of input signals of detectors 60 and 61.

When a cartridge is installed, the tube 10 closes direct way of primary beam 59 as it is shown in the top view of FIG. 13 corresponding to low pressure inside the indicator 9. In this case the tube 10 has low radius of curvature. Primary beam 59 begins its trip between reflecting surfaces 30 and 45 so that it becomes the final beam 62, which falls preferably to the detector 60. Obviously, at low pressure the detector 60 produces high analog signal whereas the detector 61 produces low analog signal, and their difference reflected in output signal of the transducer 49 is positive. If the internal pressure of the indicator 9 increases the resilient tube 10 expands and gets increased radius of curvature (see bottom view of FIG. 13). This causes the shift of final beam 63 in the direction of the detector 61 and can even result in negative output signal of the transducer 49 if the change of the volume $V_{ind}(t)$ is high enough. Gradual transition from positive to negative output signals can be recorded during a gradual volume change from its initial zero value up to its highest value allowed by the dynamic range of the transducer. The same principle can work well if light reflecting variable surface 30 and/or 45 have other shapes. Therefore, this example shows how the output signal of optical sensor system 16 is associated with geometric parameters related to the shape of external surface of the expandable element of the reservoir 1.

Figure 14:
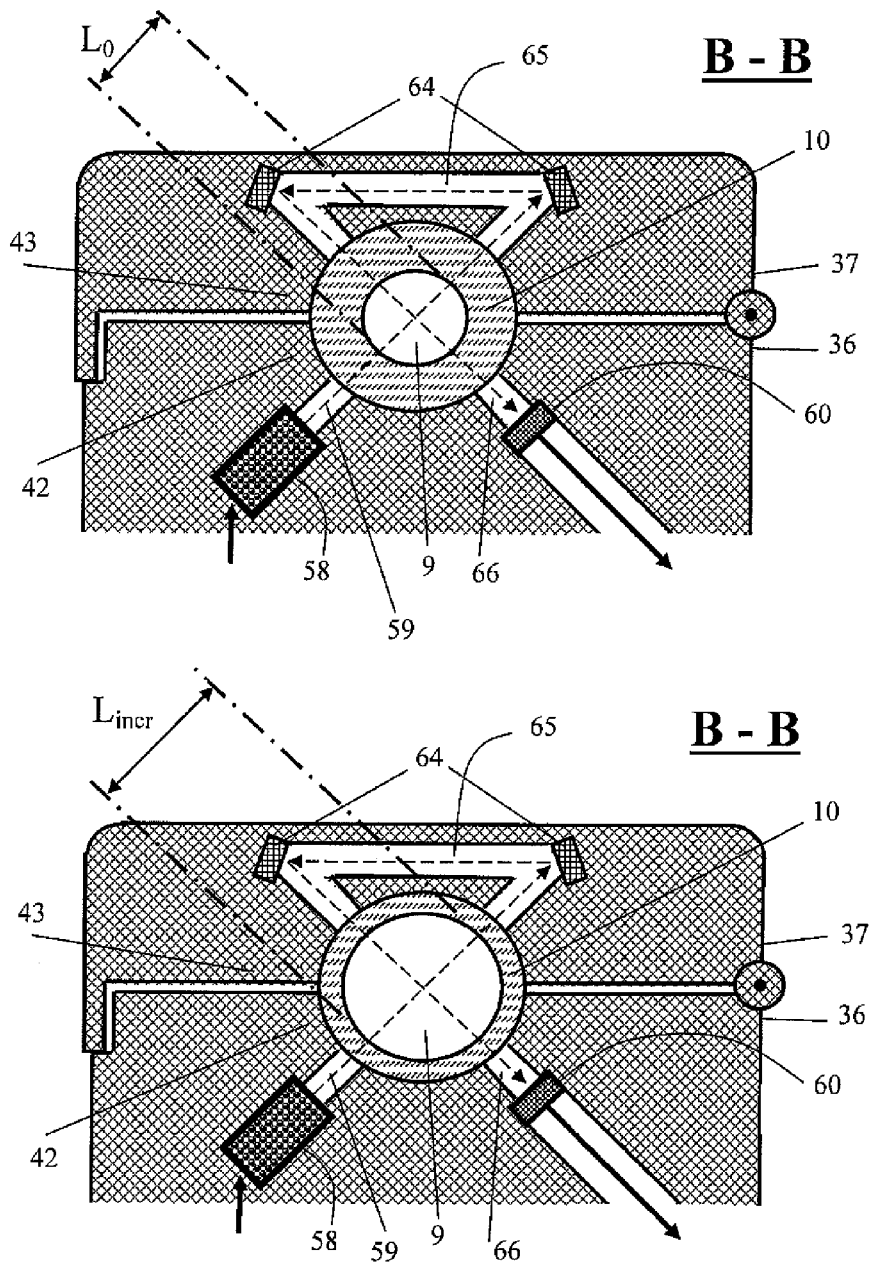
FIG. 14 depicts an example of the invention having a non-contact optical sensor combined with a replaceable cartridge as shown in FIG. 7, where an external surface of the transparent indicator's tube is fixed within the housing and only the shape of internal surface of the resilient tube changes while pressure changes.

It has been mentioned before that the suspension of the elastic section "B" may result in its undesirable vibrations and increased high frequency noise of the sensor system, especially in a narrow frequency range close to a resonance frequency of this section. That is why it may be desirable that the external surface of the indicator section 9 is fixed reliably in order to avoid such vibrations. The last example shown in FIG. 14 demonstrates that optical sensors are capable of measuring $V_{ind}(t)$ or $\Delta V_{ind}(t)$ even in such particular embodiments wherein the indicator section 9 made of elastic tube 10 having relatively thick wall is fixed reliably by compressed ribs 42 and 43 located correspondingly in the housing 36 and its closed lid 37. However, due to the fact that the thick wall of the tube 10 is made of highly elastic plastics similar to silicon rubber, the internal surface of the tube remains capable of relocating so that even modest increase of the internal pressure compresses thick plastic wall and changes simultaneously both tube's internal diameter L(t) and its volume $V_{ind}(t)$. The top view of FIG. 14 corresponds to low internal diameter $L_0$ of the tube 10 of the indicator 9 at low initial pressure. The bottom view of FIG. 14 shows increased internal diameter $L_{incr}$ at modestly high pressure. The light source 58 fixed in the housing 36 produces narrow beam 59 directed to cross the transparent elastic tube 10 near its diameter. One can see that this beam travels four times through transparent wall of the tube and two times through the volume of the fluid filling the indicator 9. This way is shown in FIG. 14 with dashed arrows. Two small mirrors 64 fixed in the channel of the lid 37 provide proper directions of reflected beams 65 and 66. The final beam 66 transmitted by the expandable internal volume of the indicator section 9 reaches the only photodetector 60 fixed in the housing 36 and creates analog input electric signal.

The principle of the optical sensor shown in FIG. 14 is based on the fact that any fluid is capable of absorbing the light in certain specific range of its optical spectrum. In this range the longer optical path 2L corresponds to higher absorption. It is desirable that the wavelength of the light source 58 is chosen in such optical range, which corresponds to both high absorption of the fluid in the reservoir (or its optically active component) and relatively high transparency of the tube's plastic material. It may be appreciated by anyone skilled in the art that in the case related to this particular sensor the intensity $J_{66}$ (L) of the outgoing light beam 66 recorded by the detector 60 obeys well known optic law:

$$J_{66}(L) = J_{59} \exp\{-2L(\Delta P_{ind})\epsilon c\} \quad \text{(Eq.7)}$$

where $J_{59}$ is the intensity of the light beam produced by the light source 58, the c is molecular concentration of either fluid itself or its optically active component (let say, the drug dissolved in the fluid), and c is its extinction factor corresponding to specific optical spectrum of given fluid at chosen wavelength of the light. The effective path of the light $2L(\Delta P_{ind})$ expresses a dependence of the internal diameter of the indicator's tube on the pressure change $\Delta P_{ind}$. Typically the variable L can change in between $L_0$ and maximum $L_{iner}$ so that $L_0 \gg L_{iner} - L_0$. In this case the variable $(L_{incr} - L_0)$ is proportional to $\Delta P_{ind}$.

It can be appreciated that in this example the recorded light beam does not change its direction. Instead, the analog input signal produced by the detector 60 is proportional to only the intensity of the transmitted light which, in contrast to previous examples, depends on internal geometric parameter of the expandable element 10 of the reservoir. Equation (7) shows explicitly that both the intensity of the transmitted light recorded and output signals of this type of non contact optical sensor are exponentially associated with such specific geometric parameter of the indicator 9 as its internal diameter L depending on the pressure change $\Delta P_{ind}$ and reflecting volume change $\Delta V_{ind}(t)$. Those skilled in the art may note that due to exponential law of the equation (7) is always known in advance, the actually recorded non linear variable $J_{66}$ can be easily transformed to such output signal S(t) which satisfy the linear equation (6). It does not matter whether this obvious logarithmic transformation is done directly by the transducer 49 or said transformation is included into special mathematical algorithm of programmable digital processor 17.

C. Programmable Control System

It can be desirable that the programmable control system comprise programmable processor 17 and control panel 18. Flexible organization of the control system and ways of information exchange between its parts are shown schematically in FIG. 3, FIG. 15 and FIG. 16. The control system may include few optional blocks shown with dotted lines. Actually, the control system plays an important role of preprogrammed "brain," which organizes the work of all the systems of the device in real time. It can be appreciated that time-sensitive actions can be performed by any electronic processor with a given precision in time. This precision is an inherent feature of any preprogrammed action and need not be described in detail herein. In accordance with the method of present invention the "brain" mentioned above is designed to fulfill the following major operations.

(a) Initiating a squeezing of the fluid out of the reservoir at the predetermined start moment when next delivery cycle is to be performed accordingly to programmed instructions. In order to do so the processor, having its internal clock, fulfills consecutively two sub-operations: (i) waiting until running real time coincides with preprogrammed start time-point $t_{st}$ of the next cycle; (ii) when the coincidence of both said times is detected the next operation is sending (see the arrow 21 in FIG. 3) the first, at least one signal to the driving force system 14. This action results in producing non-zero squeezing-out force and causes sharp increase of the pressure in the compression section 8 of the reservoir 1. It follows from the properties of the hydraulic system disclosed before that sharp jump of the pressure in the compression section 8 causes certain time-dependent (or, in other words, dynamic) continuous exposure of the expandable indicator section 9 to certain pressure difference which relates directly to the fluid delivery process.

(b) The next general task of the processor is analyzing the dynamic response of the expandable indicator section of the reservoir 1. The fulfilling of this task also consists of few sub-steps: (iii) acquiring at least one information signal S(t) formed by the sensor system 16 (see the arrow 22 in FIG. 3) and preferably more than one signal; (iv) treating these signals in accordance with predetermined mathematical algorithm in order to analyze specific features of signals and evaluate real parameters of current fluid delivery process; (v) determining the expected moment $t_{end}$ when the squeezing-out force must be terminated in order to stop outgoing fluid flow and provide an equality of the predetermined dose of current cycle and an actual dose delivered.

(c) When an expected time-point $t_{end}$ is determined the last task of the processor is terminating the squeezing-out force. It requires two sub-steps: (vi) waiting until running real time coincides with time-point $t_{end}$ determined in sub-step (v); (vii) when the desirable coincidence of both values is detected the processor must send the second, at least one ending signal to the driving force system 14. This ending signal results in sharp decreasing the squeezing-out force so that the pressure of the fluid in the reservoir can relax up to about its initial value before the cycle. Processor can also fulfill some additional operations which are described in details in the part of the description related to methods.

It has been mentioned before that in certain cases the processor may comprise analog circuitry which may be desirable only if the math operation (v) comprises the simplest algorithm of direct integration of signals S(t). However, due to analog mathematics provides less precision and is now a little bit obsolete, in further discussion of present invention it is always assumed that the contemporary digital processor is used which is capable of using rather complex mathematical programs in order to treat digital signals.

The control panel 18 is designed to activate one or more of several different programs stored in processor's memory in accordance with current needs of a user. For example, a special program can be used to calibrate the device automatically after the installation of the new cartridge. Other programs may correspond to different medical regimes of the drug delivery which can be chosen and changed at any moment by a user accordingly to his or her current medical state. In order to provide customer's control over whole device the control panel 18 should be supplied with control buttons 71 and information LCD display 72. It may be desirable in some embodiments that all systems of whole delivery device, depicted in FIG. 3, are assembled in the single housing similar to the housing 36 shown in FIG. 6. If this is the case, the bottom view of FIG. 6 shows the example of how these control elements 71 and 72 may be located on the lid 37 and/or the side wall of the only housing 36 wherein the processor, the sensor system, full hydraulic system, and driving force system are assembled together.

However, it can be appreciated that the invention provides a flexible approach for spatial organization of the control system because of three features of the invention: (i) the hydraulic system uses only passive hydraulic elements and does not contain any material part which needs to be continuously operated while the delivery cycle; (ii) the driving force system 14 also does not need to be continuously operated while the delivery cycle because it produces pulse-like squeezing-out force which needs only to be turned on at $t_{st}$ and then turned off at $t_{end}$; (iii) taking the two previous points into account the control system acts like "a supervisor" watching the actual delivery process patiently and providing only start-stop commands when necessary. That is why the control system of the invention is focused mainly on its own "intellectual" activity occurring in time rather than on actual continuous operations with other material objects. That is a reason why the processor of the invention can "think" and operate effectively independently on particular place of its location.

In other embodiments it may be more desirable for customer's convenience that entire control system including both the processor 17 and the control panel 18 is concentrated in at least one separate housing 73 (FIG. 15). The secondary part 16(b) of the sensor system may be also located in the housing 73. Desirable processes of the information exchange between the control system and other systems can be performed with the use of either wires or any appropriate wireless means. In the last case the housing 73 must be equipped with the wireless transmitters 67 and receivers 68 providing signal exchange with other housings 36 and 74. In order to stress the compatibility of the device of present invention with remote control means, all potential ways of wireless communications are shown in FIG. 15 and next FIG. 16 with thick white arrows whereas ordinary electric wire connections are represented by thin black arrows. It seems to be obvious for everyone skilled in the art that in the case of remote communication the driving force system 14 in the housing 36 and certain primary part 16(a) of the sensor system 16 in the housing 74 must be also supplied with wireless receiver 68 and transmitter 67 correspondingly.

Those skilled in the art may appreciate also that there is no technical necessity to concentrate all parts of the control system in the same housing 73 shown in FIG. 15 if specific embodiment is supplied with the wireless communication means. For the purpose of the example only it may be desirable from technical viewpoint and more convenient for a customer that the processor 17, driving force system 14, and the section 8 of the reservoir 1 are located together in the same housing 36 whereas flat remote control panel 18 is placed in separate housing 73 (FIG. 16). In this case it may be also desirable that local control buttons 71 and display 72 are located on the flat side of the same housing 73. Remote information exchange between processor 17 and control panel 18 is depicted by arrows 20 and 26. For simplicity the presence of wireless transmitters and receivers is shown in FIG. 16 by their numbers only.

The location of systems of the device in several separate housings, shown in FIG. 15 and FIG. 16 schematically, may be desirable in the particular family of drug delivery devices designed especially for children, wherein the length of the flow passage and the dimensions of the exit port assembly directly contacting with baby's body, must be as low as possible. In this case it may be reasonable to combine the driving force system 14 and the compression sections 8 of the reservoir 1 in one separate housings 36, whereas the indicator section 9 of the reservoir 1 and at least certain part 16(a) of the sensor system 16, for example, its sensing element producing the analog input signal, are combined in another separate housing 74, thus forming the exit port assembly. Examples shown in FIG. 15 and FIG. 16 demonstrate that the exit port assembly located in separate housing 74 can be made extremely compact and be supplied with hard needle 31 representing as short flow passage as possible. Simple design and low size of the exit port assembly allows its easy deploying in most desirable place of little baby's body. Moreover, if separate housings 36 and 74 are used, the exit port assembly 74 may be fully disposable part of the device because relatively long flexible tube 75, included into the hydraulic communication of sections 8 and 9 of the reservoir, may be easily connected and/or disconnected when necessary by using the connector 87 (FIG. 16). Such a simple exit port assembly does not need to contain controlling processor or any part of the driving force system. This assembly may be supplied with the means capable of transmitting signals by either wires or more preferably by wireless transmitter 67. A further advantage of the embodiments shown in FIG. 15 and FIG. 16 is that the separate housing 36 may be deployed in other convenient place of the baby's body whereas the control panel 18, deployed in the separate housing 73, remains under the control of adult people which are either baby's parents or medical specialists.

However, in any case the general scope of the invention does not depend on how many housings are used to locate different parts of the device, and what particular means provide their information exchange if it occurs in accordance with the general teaching of the invention. At the same time it should be appreciated that there is one feature characterizing the speed of the control system in its combination with the sensor system. This feature is the maximum frequency $f_0$ reflecting the process of sequential generation of output signals S(t) by the sensor system, their further transfer to programmed processor in the form of the information cluster, and final mathematical treatment of this information in order to fulfill operations (iv, v) disclosed in the third paragraph of this section. The said above means that the device is spending at least minimum finite time $1/f_0$ in order to produce and treat each single information cluster reflecting, for example, the instant state of the delivery process in one given time-point. Assuming that one cycle of the fluid dosing requires at least the time $T_c$, the number N of such information clusters (or points) produced by the sensor system and treated by the processor in one delivery cycle cannot exceed $N=T_c f_0$.

Minimum N depends on how the device is designed and what mathematical algorithm is used. It will be shown later that in the case of a simple device the minimum N is at least one and desirably it is more than one. However, more advanced devices providing better characteristics may require at least N=2 or more, and most advanced devices of present invention require at least N=5 or more.

There are other options that are not critical for the device functioning but may be rather useful for users. In rare cases of improper functioning of the device the mentioned above analysis (iv) should detect such dangerous events and result in optional alarm signals produced by optional alarm sub-system 19 which is intended to inform a user that the device itself is not able to work properly. It may be desirable also that a user is provided with the information on reasons of improper work, said information produced by analyzing algorithm and reflected on the display of the control panel 18. One more option can be used if particular fluid delivery device of the invention is intended to be used for vitally important drug delivery. In this case either the processor 17 or the control panel 18 may be supplied with additional long-distance wireless transmitters 67 and receivers 68 providing remote communication 69 of the patient's device with medical professionals 70 capable of prompt resolving emergency situations. This external medical help may include personal directions provided to a patient, or remote re-programming of the processor 17 if it seems to be necessary from medical viewpoint.

In order to make the device well controllable it may be desirable in some embodiments that the driving force system 14 reports to the processor 17 how its start-stop commands are understood and fulfilled. The arrow 25 in FIG. 3 shows this optional way of the information exchange. It may be desirable also that optional signals 24 are sent by the processor to activate the sensor system 16 while the delivery cycle. These optional signals can help to synchronize the information exchange and conserve batteries in the dead time periods between cycles.

D. Driving Force System

The driving force system 14 shown in FIG. 3 schematically is designed to activate the fluid flow by squeezing the fluid out of the reservoir 1. In accordance with the teaching of the invention, during each cycle only a predetermined relatively low dose $D_0$ of the fluid is to be delivered to the exit opening of the device. That is why it is desirable that the system 14 is represented by such technical means which are capable of changing the force squeezing the fluid out of the reservoir 1 over time. It may also be desirable that the squeezing-out force continues only for a limited time $T_c$ corresponding approximately to the duration of one cycle of the fluid dosing. It may be desirable that the system 14 is capable of creating pulse-like squeezing-out force applied only to certain limited surface area of the fluid filling the compression section 8 of the reservoir 1 in order to cause rapid increases in the pressure in said compression section. As it has been described before, the time-dependent pulse-like change of the excessive pressure in the section 8 is designated as $\Delta P_{comp}(t)$. In accordance with the equation (3) the term $\Delta P_{comp}(t)$ expresses a difference of full fluid pressure $P_{comp}$ in the compression section 8 and external pressure $P_{ext}$ which is typically external atmospheric pressure. Due to fact that the driving force system 14 is capable of causing the compression of the fluid in the reservoir, it may be also called hereinafter as "the compression system" for brevity. As it has been already mentioned, before each dosing cycle the fluid in the reservoir is subjected to as low pressure as may be necessary to prevent the fluid to flow out of the exit opening. Actually, this low pressure in whole reservoir, including its compression section 8, must be close to an external pressure $P_{ext}$ which is typical atmospheric pressure.

Each dosing cycle begins at programmatically predetermined moment $t_{st}$ which is the moment of the real time. However, in order to make the description as simple as possible it is more convenient hereinafter to consider all processes of each given cycle in terms of its local time t which is chosen so that local t=0 at the moment $t_{st}$ of the real time. What is said in previous paragraph means that the cycle starts at local moment t=0, and $\Delta P_{comp}(0)$ is about the zero.

The desirable pulse-like excessive pressure $\Delta P_{comp}(t)$ begins when compression system 14 gets the first starting electric signal initiated by programmable control system. It is desirable that immediately after start signal the increase $\Delta P_{comp}$ occurs rapidly until it reaches a certain level $P_0$ corresponding to predetermined bracket condition $P_{max}>P_0>P_{min}$. It also may be desirable that after a short raising period further increase of the pressure is stopped so that the elevated pressure in the section 8 remains close to obtained high value $\Delta P_{comp}=P_0$ during the time $T_c=t_{end}-t_{st}$ of the delivery cycle. In other words this means that the first starting signal activates the system 14 for only rather short time $T_{up}$ which should be enough to cause a pressure increase $\Delta P_{comp}=P_0$. After that the system 14 goes automatically to the waiting mode and does nothing until it receives the next signal from the processor. This process is analogous to what is depicted in the middle image of FIG. 2 where fast increase of the pressure in the elastic reservoir is caused by one quick move of the finger 4, and then excessive pressure remains almost constant for some time even if a position of compressing finger is fixed.

Termination of the delivery cycle is a reverse of the above process. It occurs when the system 14 gets at least one ending electric signal initiated by control system at local moment $t=T_c$. It is desirable that the ending signal activates the system 14 again and makes it to remove the compressing force over a short time $T_{down}$. After that pressure drop occurs in the section 8 until $\Delta P_{comp}$ returns back to its initial zero value. This process is analogous to what is depicted in the bottom image of FIG. 2 after the finger 4 is removed and elastic wall of the reservoir relaxes quickly.

Figure 17:
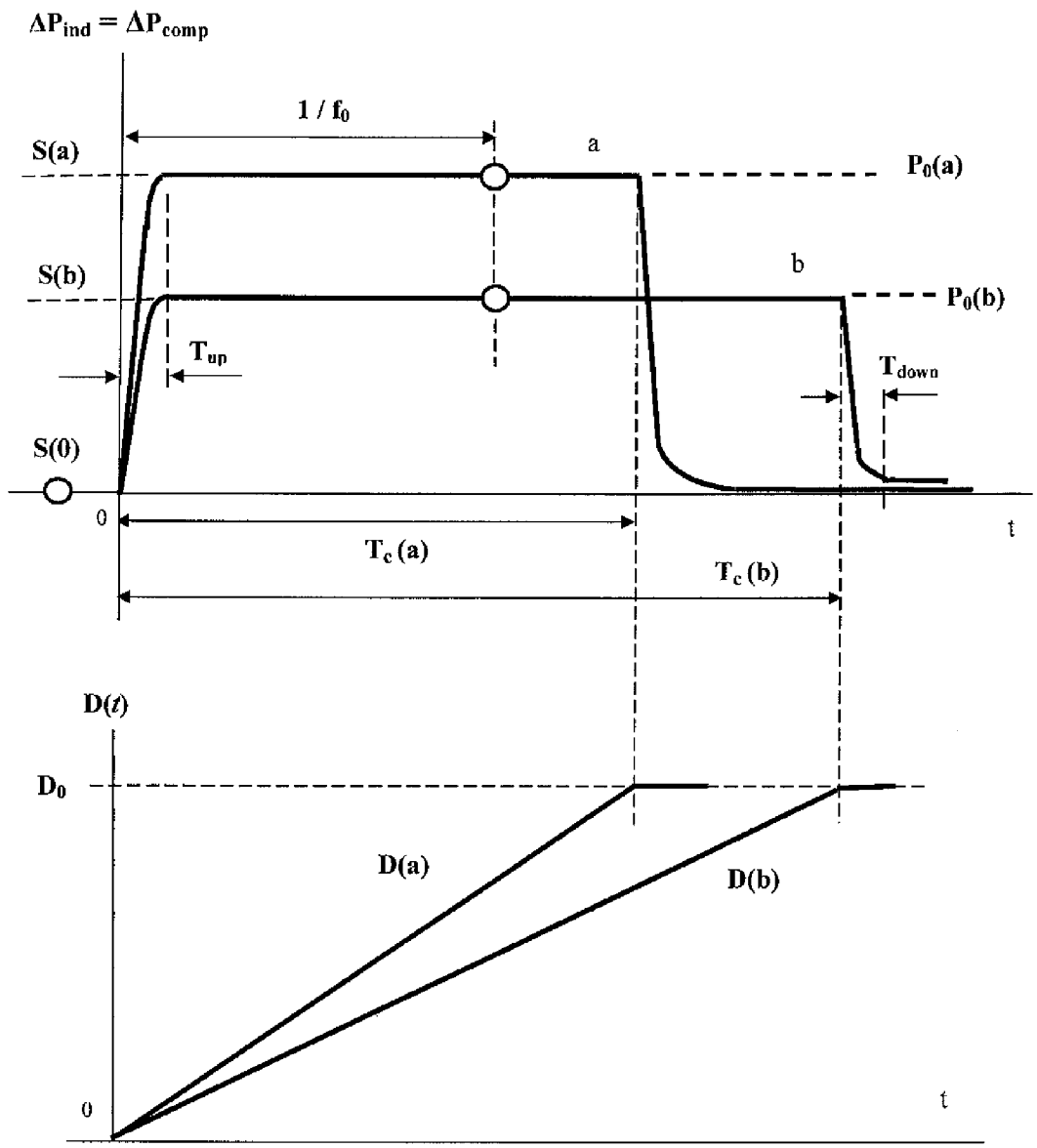
FIG. 17 depicts examples of two different quasi-rectangular time-diagrams of pressure pulses produced in the compression section of the reservoir of an embodiment of a device of this invention (top view), and the corresponding time-diagrams of the fluid doses delivered to the device's exit opening (bottom view). White circles correspond to the readings of output signals produced by the sensor system. For simplicity these output signals are shown as if their scale coincides with the pressure scale of the indicator section of the reservoir.

Thus, it can be desirable that the time diagram representing $\Delta P_{comp}(t)$ must look as purely rectangular pulse having the desirable amplitude $P_0$ and algorithmically determined duration $T_c=t_{end}-t_{st}$ which is understood hereinafter as the time interval between said starting and ending signals. However, it can be appreciated that in real devices the shape of actual diagram $\Delta P_{comp}(t)$ may differ significantly from ideal one. Two diagrams shown in the top of FIG. 17 represent more realistic examples of two independent cycles $\Delta P_{comp}(t)$ having different amplitudes $P_0(a)$ and $P_0(b)$ notwithstanding their quasi-rectangular shape is close to ideal expectations. An advantage of the present invention is that precision of the fluid delivery can be maintained in the face of even substantial variations of real diagrams $\Delta P_{comp}(t)$ related to different cycles. Thus, a mechanism of the compressing system 14 can be made simple without the need for high precision parts. For example, the amplitude $P_0$ produced in different cycles may be up to five times more and/or up to five times less than its average value expected by a preprogrammed processor. In other words, the bracket ratio $P_{max}/P_{min}$ can be as high as about 25. Moreover, some embodiments can work properly even if the elevated plateau of the pressure pulse is not quite stable and can change during $T_c$ up to about 70% of $P_0$ or even more (see top view of FIG. 18 for example). Discussed later "smart" algorithms related to the method of present invention are capable of compensating very strong variations of the shape of $\Delta P_{comp}(t)$.

It can be appreciated that due to "soft" technical requirements the mechanism of the compression system 14 of the invention may be simpler and less precise than complicated high precision mechanisms of known devices of the prior art. However, actual behavior of the system 14 desirably satisfies at least certain minimum requirements related to average $T_c$. It may be desirable that average interval $T_c$ exceeds at least about two times the typical time $T_{up}$ of fast transition from initial level $\Delta P_{comp}(0)=0$ to the highest pressure achieved in the compression section 8 during $T_c$. It can be desirable that average $T_c$ exceeds $T_{up}$ at least about ten times, and it can be desirable that average $T_c$ exceeds $T_{up}$ by about fifty times or more. For example, if the average duration $T_c$ of the dosing cycle is chosen to be about 20 s then a desirable transition time $T_{up}$ can be not longer than 0.4 s, and alternatively, not exceed 10 s.

It may also be desirable that after the ending signal is sent by the control system, a rapid pressure drop occurs in the compression section 8 of the reservoir 1 during as short time $T_{down}$ as the first transition time $T_{up}$ discussed above. The examples depicting both transition times $T_{up}$ and $T_{down}$ are provided in FIG. 17 and FIG. 18.

Figure 19:
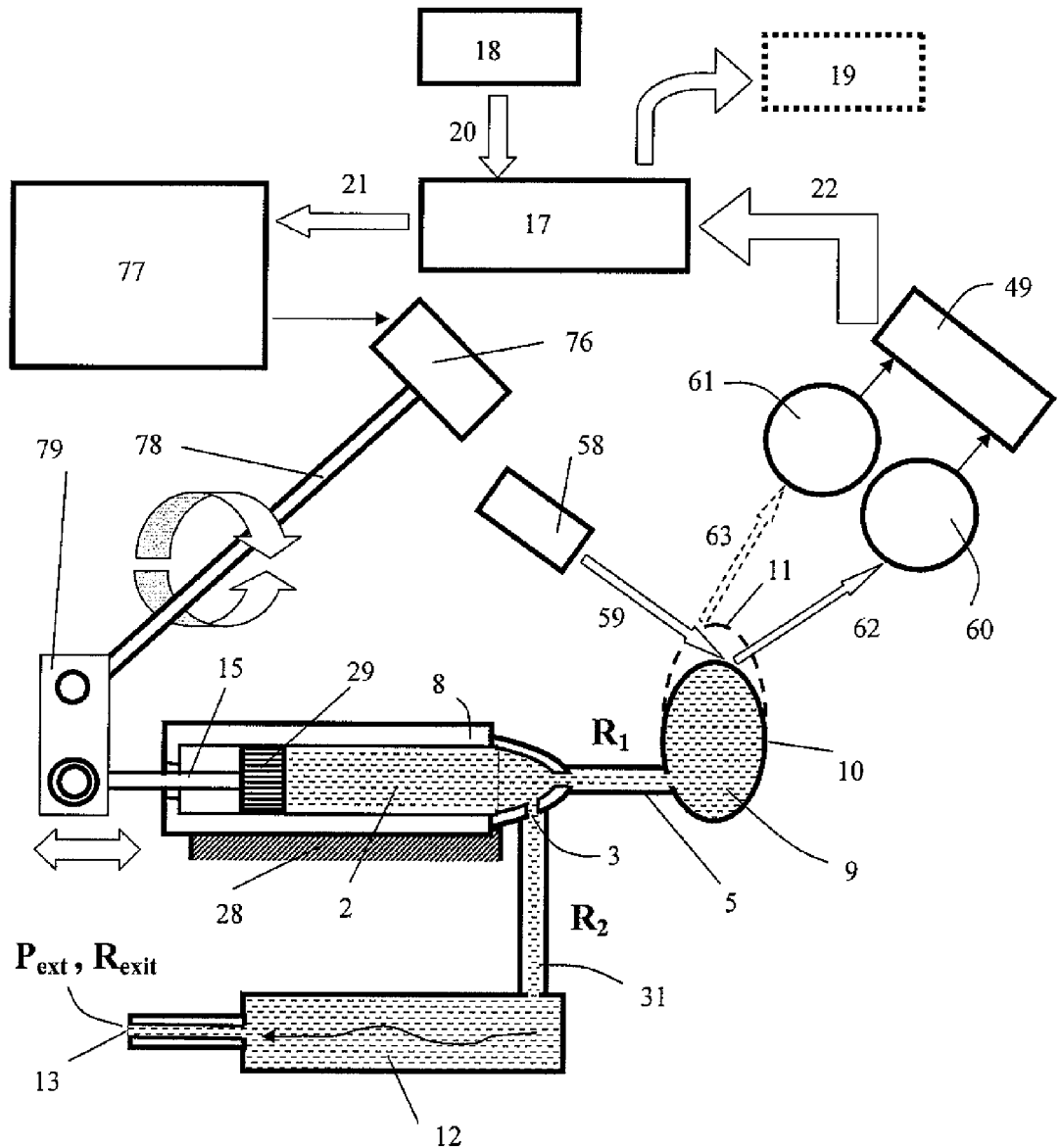
FIG. 19 depicts schematically an embodiment of a device of the invention wherein the flow passage is connected with the compression section of the reservoir (see also FIG. 5 for more details). The electro-mechanical driving force system, built on the basis of a traditional syringe, is shown as an example.

Multiple different executive mechanisms of the system 14 can be used to fulfill simple technical conditions disclosed above. FIG. 19 represents schematically an example of a simple device of the invention wherein the compressing mechanism of the system 14 exploits traditional syringe shown also in FIG. 5. In order to change the squeezing-out force over time, this kind of compressing system comprises piston 29 inserted into the syringe's body 8, and an electromechanical system capable of moving said piston in either of two opposite directions according to two control signals 21 sent by the processor. Also, this mechanism comprises block 76 combining the electric step-motor with the mechanical reducer. The motor is connected with standard power supply 77 causing the step-motor to make a programmatically determined number of angular steps in any direction, whether clockwise or counterclockwise (see thick round arrows), according to either starting or ending signals of the processor 17. The rotating driving shaft 78 of the reducer is combined with the lever 79 in order to transform this rotation into back-and-forth movement (shown with thick double directed arrow) of the piston rod 15. In this example it is desirable that the syringe's body 8, the piston 29, and all moving parts of the system 14 are made of hard materials. At the same time all elastic properties of the syringe-like reservoir shown in FIG. 19 are fully concentrated in its indicator section 9.

A typical cycle of a syringe-like compressing system 14 shown in FIG. 19 is described below. A first starting signal sent by the processor 17 causes the step-motor to make programmatically predetermined number $M_{up}$ of steps. Correspondingly, the counterclockwise rotation of the driving shaft 78 makes the piston 29 to slide predetermined distance $\Delta l$ in the right direction. This first movement takes a short time $T_{up}$, for example about 0.2 s, and then the step-motor stops to conserve the battery. Piston 29 applies the compressing force only to the limited surface area $S_{pist}$ of the fluid 2 located inside the syringe 8 and causes sharp increase of fluid's pressure $\Delta P_{comp}(t)$. It can be desirable that the volume $\Delta V$ expelled by the piston's relocation exceeds the preprogrammed fluid dose $D_0$ of current delivery cycle by the order of magnitude, for example about 20 times. It may be obvious for those skilled in the art that the process of expelling may be accompanied by certain expansion of both elastic ring 29a and the body of the syringe 8 made of hard material. It is desirable also that simple devices satisfy the condition $R_2 \gg R_1$ as shown in FIG. 5. Due to the transition time $T_{up}$ being short, and the flow passage 12 comprising substantial non zero resistance $R_2$, the fluid volume $\Delta V$ expelled by the piston cannot leave from exit opening 13 immediately. Instead, due to a relatively low $R_1$ this volume is moved quickly from the section 8 made of hard material to expandable section 9. FIG. 19 shows how the initial shape of the elastic element 10 gets its expanded shape 11 in the process of a rapid pressure increase in the indicator. It can be appreciated that the fluid's volume $\Delta V$ expelled by the piston into expandable indicator section 9 during the short transition time $T_{up}$ can be expressed as: $\Delta V_{ind} = S_{pist} \Delta l$. In the case of a simple device supplied with the syringe-type system 14, the amplitude $P_0$ of jump-like pressure increase is practically the same in both the compression and the indicator sections of the reservoir 1. In accordance with the equation (4) it obeys the following expression:

$$P_0 = \alpha S_{pist} \Delta l \qquad (Eq.8)$$

Both the resistance $R_2$ and actual pressure $P_0$ measured by the sensor system during each cycle are known to the processor, which calculates both the real magnitude of the fluid flow and right cycle duration $T_c$ corresponding to the desirable dose. When the proper $T_c$ is reached and desirable dose $D_0$ is obtained, the processor sends the ending signal to the power supply block 77 of the system 14. After that the step-motor 76 makes predetermined number $M_{down}$ of back steps, rotates the driving shaft 78 clockwise and makes the piston 29 to slide back in the left direction. This takes short time $T_{down}$ only and results in fast decrease of squeezing-out pressure in the reservoir as shown in top view of FIG. 17. It should be appreciated that typically the numbers of motor's steps are to be chosen in accordance with simple condition $M_{up} > M_{down}$, providing an effective way of controlling the piston's actions.

Expression (8) can be further used in order to compare more specifically the features of the devices of the invention with those of prior art syringe-like drug delivery devices. The quantitative example considered below is based on a few parameters which can be practically used in simple devices of the invention. A device is supplied with the syringe-like system 14 wherein typical syringe has piston area about $S_{pist} = 1$ cm². For a quantitative comparison, consider that typical preprogrammed one-cycle dose of the insulin is $D_0 = 12$ mm³, and desirable precision of the insulin delivery is selected to be about 0.1 mm³. In order to provide such a dose in one cycle, the piston of prior art devices must be shifted 0.12 mm with the precision better or about 0.001 mm, thus corresponding to about 1 micron. The difficulty of getting such high precision is well known, and therefore the desired precision of 0.1 mm³ does not seem to be realistic.

In contrast, equation (5) tells that in simple devices of the invention the factor $\alpha$, depending on resilient properties of the elastic element 10 and characterizing the expandability of the indicator section 9 of the reservoir, can be easily made equal 1 Kgram/cm⁵. In this case it also follows from equation (5) that the average amplitude of the pressure pulse in both compression and indicator sections of a simple device (for example see the curve (a) in top view of FIG. 17) is about $P_0 = 0.2$ Kgram/cm² when the program orders the piston's shift equal $\Delta l = 2$ mm. So, during the short time $T_{up}$ the piston is pumping up the expandable indicator section 9 with the additional fluid volume about $\Delta V_{ind} = 200$ mm³, which is really about 20 times more than requested dose $D_0 = 12$ mm³.

At the same time resistor 31 included in the flow passage can be made in the form of the short needle having typical length of about 2 cm and internal diameter of about 0.07 mm, thus providing high hydraulic resistance about $R_2 = 330$ (Kgram·s)/cm⁵. It follows from the equation (1) that rather moderate magnitude of the outgoing flow $F = 0.6$ mm³/s appears in the exit opening 13 when the pressure difference 0.2 Kgram/cm² is applied to said high resistance $R_2$. Correspondingly, the delivery cycle must continue about $T_c = 20$ s in order to obtain the full desired dose $D_0 = 12$ mm³. It should be apparent that both the processor 17 and executive mechanics of the system 14 can easily control the cycle's duration $T_c$ with the precision at least 0.025 s or better. At given intensity $F = 0.6$ mm³/s this time-precision 0.025 s corresponds to very high dosing precision 0.015 mm³ easily achieved even with the simplest device of the invention. This estimate shows advantages inherent even for the simplest embodiments of the invention. At the same time it can be appreciated that particular numbers are provided above as an example only, which cannot create any limitations for any other embodiments of the invention.

The estimate of previous paragraph contains the assumption that elevated pressure remains constant while whole period $T_c$. Real processes can be close to this assumption because the expandability of the indicator 9 is high, and low dose $D_0$ leaving the reservoir for $T_c$ represents only small fraction of the volume expansion $\Delta V_{ind}$ of the section 9. At quantitative parameters chosen for this particular example it is easy to see that $\Delta P_{comp}(t)$ changes during $T_c$ not more than about 5%. Due to this change is fully predictable the processor's algorithm can take it into account and make necessary correction of calculated $T_c$. It may be obvious for everyone skilled in the art that much higher stability of $\Delta P_{comp}(t)$ can be easily achieved if one increases the preprogrammed volume change $\Delta V_{ind}$ and/or decreases preprogrammed $D_0$. For example, the stability of the pressure $\Delta P_{comp}(t)$ becomes better than 1% in each $T_c$ if predetermined dose $D_0$ of one cycle is chosen to be 2.4 mm$^3$. Correspondingly, in order to keep the same final dose 12 mm$^3$ one needs only that the high precision cycle of 2.4 mm$^3$ is repeated five times.

In order to complete the quantitative comparison of prior art devices and those of the present invention, let make an assumption that due to certain errors occurring in one embodiment, the piston 29 has been actually moved only 1.3 mm instead of programmatically expected value $\Delta l=2$ mm. It follows from equation (8) that due to such mechanical error the real pressure increases only up to $P_0=0.13$ Kgram/cm$^2$ which is much lower than expected (compare, for example, curves (b) and (a) in top view of FIG. 17). Correspondingly, the intensity of the output flow becomes equal low value $F=0.39$ mm$^3$/s. However, in order to keep the desirable output dose $D_0=12$ mm$^3$ constant, one needs only to increase the duration of the delivery cycle from the previous 20 s to new $T_c=30.8$ s (see bottom view of FIG. 17). This task is the responsibility of processor 17 which calculates the correct $T_c$ on the basis of the information about the real amplitude $P_0$ received from the sensor system 16. This calculation causes proper delay of the ending signal and restores desirable output fluid dose. Therefore, one can see that even a large mechanical error of a piston's shift of about 700 microns, occurring accidentally in the system 14 of the invented device, does not influence the final precision of the fluid delivery. At the same time prior art devices fail if their similar error exceeds 1 micron. These numbers explain why and how the devices of the invention can achieve better precision and reliability simultaneously with simplification of their executive mechanisms.

Those skilled in the art may appreciate that neither parts made entirely of hard materials, such as the piston of the syringe and/or its body, nor the electric motor are required features of the means 14 capable of changing over time the force squeezing the fluid out. FIG. 20 and FIG. 21 represent schematically two other examples of embodiments wherein there is no electric motor at all. In these embodiments the compression section 8 is to be supplied with the walls made at least partially of easily deformable elastic materials. In both examples the section 8 of the reservoir 1 is placed into the limiting cavity 80 of the housing 36, and the system 14 comprises the expandable bag 81 made preferably of highly elastic plastic material and filled with a gas, which is preferably the air. The system 14 further comprises certain means capable of changing a temperature of the gas in the bag 81 according to control signals produced by the processor 17. In order to do so it may be desirable that there is an electric heater 83 placed inside the bag 81 and connected with electronically controlled power supply 84 which can be turned on and off in accordance with signals of controlling processor 17. In accordance with the first example shown in FIG. 20, the expandable bag 81 is located in the same cavity 80 in close proximity of at least such part of the section 8 of the reservoir 1 which is supplied with said elastic wall. In this case the bag 81 has no direct contact with the fluid, but any expansion of the bag 81, caused for example by increased gas pressure inside the bag, applies the compressing force to the elastic wall of the compression section 8 of the reservoir 1, deforms this elastic wall (exactly as the deforming finger 4 does in the middle of FIG. 2), and thus creates the squeezing-out force inside the reservoir 1. In the second example shown in FIG. 21, the expandable bag 81 is located inside the compression section 8 of the reservoir. In this case it does not matter whether external walls of the section 8 are made of elastic material or not because expandable bag 81 contacts with the fluid and is capable of applying the squeezing-out force directly.

It may be desirable that before the dosing cycle, the gas in the bag 81 is subjected to external atmospheric pressure $P_{atm}$. For example, this condition can be fulfilled if the bag 81 filled with the air has very small opening 82 having so high aerodynamic resistance that the air pressure inside the bag 81 becomes equal $P_{atm}$ for relatively long time exceeding typical period $T_c$ by at least one order of magnitude and desirably much more than one order of magnitude. For example, if the average $T_c$ is close to 20 s it may require 600 s or more to establish the equality of internal pressure in the bag 81 and $P_{atm}$. It may be also desirable that walls of the limiting cavity 80, which surrounds both the bag 81 and the section 8 of the reservoir, are made of the material providing good heat conductivity. For example, this material may be a metal such as copper or aluminum, or any composite material having good heat conductivity. If this is the case it provides the ability of quick heat exchanging between the cavity 80 and the air in the bag 81.

Before the fluid delivery cycle, the electronic power supply 84 is in the off state in order to conserve the battery. In accordance with some embodiments, the starting signal sent by processor 17 turns the power supply 84 on, and the air temperature inside the bag 81 can increase up to predetermined value. For example, even rather modest heating of the air to a temperature of about 60° C. is enough to produce a rise in gas pressure about 0.2 Kgram/cm$^2$, which can lead to substantial expansion of the elastic bag 81 and, correspondingly, to the appearance of the force applied to the fluid surface in the section 8 of the reservoir. If block 84 maintains constant heating power, this pressure can remain practically constant during $T_c$ and the fluid delivery processes occur as described previously. When period $T_c$ determined by the processor is over, the processor sends its ending signal and turns block 84 off in order to stop heating. Due to low heat capacity of the gas contained in the bag 81 the low excessive heat is permitted to escape through the conducting walls of the cavity 80. This leads to drop of excessive air pressure expanding the bag 81 and to a corresponding pressure drop inside the compression section 8. That is why such embodiments having no motor (FIG. 20 and FIG. 21) are also capable of producing quasi-rectangular pulse diagrams $\Delta P_{comp}(t)$ similar to that shown in the top of FIG. 17.

Those skilled in the art may appreciate that desirable pulse-like quasi-rectangular diagrams $\Delta P_{comp}(t)$ can also be produced if the reservoir 1 made at least partially of the elastic material is combined with electromotor-driven peristaltic system 14 shown in FIG. 22, which is capable of both compressing and decompressing at least part of elastic wall of said reservoir. This particular example of the system 14 may be preferably used in drug delivery devices designed especially for the installation of the disposable cartridge having elastic reservoir 1. Details of FIG. 6 demonstrate clearly how such cartridge can be placed into the housing 36 so that the elastic section 8 of the reservoir is positioned between immovable plate 28 and the compressing plate 47 which is capable of changing its angle γ. This change of the angle γ is demonstrated in FIG. 22 by thick double directed arrow near the right end of the plate 47. Before the delivery cycle the initial pressure inside the reservoir is practically equal to $P_{ext}$. Correspondingly, the initial angle $\gamma_0$ is chosen so that the plate 47 just touches the elastic wall 8 of the reservoir with about zero compressing force. If desired, some embodiments can be also supplied with the optional valve 85 which is generally closed and can be opened for short times only by special command 86 of the processor in order to eliminate low residual pressure inside the reservoir.

In order to produce desirable quasi-rectangular change $\Delta P_{comp}(t)$, the starting signal of the processor 17 urges the step-motor 76 to rotate both the driving shaft 78 and the eccentric wheel 48 so that the plate 47 decreases the angle γ and compresses the elastic section 8 in order to cause an increase of the fluid pressure. After the desirable pressure change $P_0$ is obtained, the step-motor stops to conserve the battery. Due to the elasticity of the compressed section 8 the excessive pressure $P_0$ remains practically constant during $T_c$. When the power supply block 77 receives the ending signal, the step-motor rotates the eccentric wheel in the opposite direction, increases the angle γ up to about its initial value, and thus eliminates the squeezing-out force. The following quick relaxation of the elastic wall of the section 8 leads to the fast drop of the pressure inside the compression section of the reservoir. Obviously, the resulting shape of the $\Delta P_{comp}(t)$ is very similar to quasi-rectangular pulse diagrams in top views (a) of FIG. 23 and FIG. 24.

In some embodiments of the invention, the elastic reservoir of the disposable cartridge may be designed so that after the installation of new cartridge the surface of the plate 47 becomes firmly connected with the elastic wall of the section 8. If this is the case then the device, supplied with such peristaltic system 14, gets the ability of causing from time-to-time some modest expansion of the elastic wall 8 and, correspondingly, producing short-term negative pressure change inside the reservoir. This relatively rare action may be desirable in devices capable of automatic self-calibrating when a new cartridge has been recently installed. Mechanical expansion of the elastic section 8, causing said negative pressure change, can be only performed in accordance with special signal of the processor fulfilling said calibration program and making the step-motor to increase the angle γ above its initial value $\gamma_0$.

Examples of different driving force systems 14 discussed above provides evidence that the pulse-like pressure change in the fluid, filling the compression section of the reservoir, can be achieved with multiple choices of different mechanisms and materials. Each particular choice may depend first of all on how other parts of the device are designed and what technical demands are to be satisfied in given specific application. However, it should be appreciated that the general teachings of the present invention do not depend on the technical peculiarities of the system 14 if the real shape of the time-dependent pressure pulse $\Delta P_{comp}(t)$ produced by this system is close enough to the ideal shape anticipated by the preprogrammed algorithm of the processor. In the next sections of this description preprogrammed algorithms certain devices are based preferably on quasi-rectangular shapes of $\Delta P_{comp}(t)$, whereas other devices can be suitable even with relatively unpredictable shapes $\Delta P_{comp}(t)$ which may be very different from quasi-rectangular ones.

E. Methods for Programmable Drug Delivery: General Points

Here, it may be relevant to recapitulate a few points which apply to certain versions of the invention. Hereinafter, any current cycle of the fluid delivery will, in this section, be called simply "the cycle" for brevity. Processor 17 has its internal electronic clock providing real time synchronization of all operations of the current cycle, including measurements, sending and/or receiving all service signals, mathematical operations, and so on. That means that the processor's memory stores a reading of the real time corresponding to preprogrammed moment $t_{st}$ of the beginning of current cycle. Real time $t_{st}$ of the processor's algorithm operates with local time starting at t=0. That is why processes and operations related to this cycle are represented below in terms of local time t≧0, and the preceding period is denoted as t<0. Because the processor remembers the start point $t_{st}$, it can correlate the local time t of the cycle with running readings of the real time when such correlation is necessary.

Also at t<0 driving force system 14 keeps the squeezing-out force about zero so that both the exit opening of the device and the fluid inside the reservoir are subjected to about the external pressure $P_{ext}$. Thus, at t<0 the elastic element 10, involved directly in producing output signals of the sensor system 16, is not stressed and only its non-disturbed geometric parameter (or parameters) are reflected by the output signals during this time. It can be appreciated that due to unpredictable temperature changes, aging of materials, and other similar processes, the physical properties of both the elastic element 10 and sensing elements of the system 16 can slowly drift with time. For better precision it may be desirable that at t<0 the processor automatically acquires signals S(t) from time-to-time, for example, one signal per min, and remembers the last signal received before t=0. This last signal is denoted hereinafter as S(0). Due to drift, processes are very slow and the S(0) represents the actual starting state of both the element 10 and sensing elements of the system 16 at the moment t=0. That means that only the difference [S(t)−S(0)] can correctly reflect change of the indicator's volume caused by the appearance of non-zero squeezing-out force. However, as an approximation, the value S(0)=0 can be used, thus converting the long expression [S(t)−S(0)] to the shorter form S(t).

The first step in the delivery process is the initiating non-zero force squeezing the fluid out of the reservoir. It occurs at local time t=0 as determined by the processor in accordance with preprogrammed delivery instructions. If desired, for example in the case of an emergency, the moment t=0 may be also defined by personal actions of a patient using the buttons of the control panel 18. At t=0 the processor 17 produces at least one starting signal and transmits it to the system 14, which creates non-zero squeezing-out force for time $T_{up}$, and applies this force directly to a portion of the surface area of the fluid located in the compression section of the reservoir. This leads to an increase of fluid's absolute pressure $P_{comp}$ in the compression section of the reservoir. The increase in pressure $[P_{comp}-P_{ext}]=\Delta P_{comp}(t)$ forces the fluid to flow out of the reservoir and, correspondingly, out of the exit opening at the beginning of the dosing process. Simultaneously the non-zero pressure difference $\Delta P_{ind}(t)$ occurs in the indicator section, which is used to control the entire process of the delivering the dose of drug.

The actual $P_{comp}$ achieved during each particular cycle may differ from the desired value determined by the processor's program. Taking this into account, it may be desirable that the compressing system 14 be capable of subjecting the fluid to excessive pressure within predetermined brackets $P_{max} > \Delta P_{comp}(t) > P_{min}$. The maximum value of the excessive pressure related to given cycle is denoted $P_0$. The actual value of this parameter can fluctuate from one cycle to another one even if the processor orders the same desirable value $P_0$. Due to hydraulic connection of both compression and indicator sections, the pressure difference $\Delta P_{ind}(t)$ is also limited by pressure brackets similar to ones limiting $\Delta P_{comp}(t)$.

After initiation of $\Delta P_{comp}(t)$ the system 14 goes automatically into passive waiting mode that continues up to local time moment $t=T_c$. At this moment $T_c$ determined by the processor, the compressing system 14 receives the ending signal which orders the system 14 to terminate the squeezing-out force over time $T_{down}$. It can be desirable that this time period be short. That means that between the starting and ending signals, the system 14 is not required to do anything what could change the non-zero squeezing-out force creating both the excessive pressure $\Delta P_{comp}(t)$ and pressure difference $\Delta P_{ind}(t)$. Variations of the general method relate to actions performed by both the sensor system 16 and the processor 17 during period $T_c$ between said starting and ending signals. Actions occurring during $T_c$ comprise the second step of the general method, namely producing at least one, and alternatively more than one, output signal by the sensor system 16, and then acquiring said signals associated with at least one geometric parameter of the resilient element 10 of the reservoir 1 by programmable processor 17. Treating acquired signals by the processor performing a predetermined mathematical algorithm represents the third step of the general method. It results in determining a real time moment $t_{end}$ corresponding to the duration of the cycle $T_c = t_{end} - t_{st}$, which provides the dose actually delivered to the exit opening equal the desirable dose predetermined by delivery instructions. Actions constituting the third step of the general method will be specifically discussed later. The last step of the general method of the invention begins at local moment $T_c$ and instructs the system 14 to decrease the squeezing-out force so that the excessive pressure $\Delta P_{comp}(t)$ drops to about zero. The result of this action is that the pressure of the fluid in the whole reservoir, including $\Delta P_{ind}(t)$, can return to about its initial value. Correspondingly, the last step of the method stops the flow of outgoing fluid flow and terminates the current cycle.

The organization of the third step is worth further discussion. Due to the fluid flows from the exit opening for time about $T_c$ the actual dose delivered during each cycle depends on both the duration $T_c$ of the squeezing-out force and actual magnitude of outgoing fluid flow $F(t)$ which is also time-dependent. Determining the actual dose delivered to the exit opening is a responsibility of the processor using a predetermined algorithm to treat signals acquired during the cycle. An algorithm of the invention must take into account that in accordance with the expression (6) these signals always reflect time-dependent pressure difference $\Delta P_{ind}(t)$ in the indicator section of the reservoir. That is why the kinetics of the actual dose D(t) expressing its dependence on the time can be represented mathematically as:

$$D(t) = \int_0^t F(t)dt = \frac{1}{R_{exit}} \int_0^t \Delta P_{ind}(t)dt \quad \text{(Eq. 9)}$$

where the parameter $R_{exit}$ has been defined before (see Eq.5). The expression (9) follows from general hydrodynamic laws and gives a universal mathematical approach applicable to all devices of the invention wherein the flow passage 12 communicates hydraulically with the indicator section 9 as shown in FIG. 3. In other words, an algorithm of the invention considers the actual dose delivered to the exit opening as a time-dependent ratio, wherein the numerator is an integral found by integrating of the pressure difference $\Delta P_{ind}(t)$ over time since the moment $t_{st}$, and the denominator of the ratio is a certain parameter expressing output hydraulic resistance $R_{exit}$ of hydraulic means 12 connecting the reservoir with the exit opening.

When the dependence of the actual dose on the time D(t) is determined according to Eq.9, an algorithm of the invention further compares D(t) with the predetermined dose $D_0$ in order to find proper $T_c$ needed to provide the proper dose delivered. The actions listed above are common for all methods of the invention, and only details of some actions can be performed differently in different devices. In that regard one can note that in some embodiments the kinetic features of the pressure difference $\Delta P_{ind}(t)$ in the indicator section may be different from those of excessive pressure $\Delta P_{comp}(t)$ in the compression section of the reservoir. In order to take this circumstance into account, a few different algorithmic versions are considered below. The specificity of each particular algorithm is focused on two following matters: (i) how the integration procedure is performed, and (ii) what information source is used in order to determine the parameter $R_{exit}$ substituted into the denominator of the expression (9).

The many devices of the present invention may be subdivided in three groups representing different technical designs, namely simple devices, more advanced devices, and most advanced devices. Correspondingly, the third algorithmic step of the general method of the invention contains specific operational details and additional features related only to each particular group of the three. It may be reasonable to begin the description of these specific features from the method related to simple devices, and then to consider more advanced versions.

F. Methods for the Drug Delivery Executed by Simple Devices

A simple algorithm useful in the operation relates to devices built in accordance with a simple scheme shown in FIG. 19, wherein the opening 3 connecting the flow passage 12 with the reservoir 1, may be located at any section of the reservoir. For example, the opening 3 may be located on the wall of the compression section 8. As mentioned in the section D, it may be desirable in such group of simple devices that two hydraulic resistors 5 and 31 are made so that their resistances correspond to the condition $R_2 \gg R_1$, and in other embodiments, $0.05\, R_2 > R_1$. In this case the fluid has approximately the same pressure in both sections 8 and 9 of the reservoir 1, and both diagrams of elevated pressure $\Delta P_{comp}(t)$ and $\Delta P_{ind}(t)$ practically coincide. Before the beginning of the work, the programmable processor of any simple device must contain the value of the resistance $R_2$ which is factory pre-set constant coinciding with the output resistance $R_{exit}$ at least in the beginning of the work of the device. Correspondingly, the processor considers pre-set $R_2$ as output resistance $R_{exit}$ and substitutes this value into the denominator of the Eq.9. Due to preliminary factory calibration of the device, the processor also contains pre-set constants $\alpha$ and $\beta$. In accordance with the equation (1) the knowledge of the resistance $R_{exit}$ provides knowledge of the magnitude of the fluid flow delivered by the simple device to the exit opening at any time moment t during full time $T_c$ of the cycle. This magnitude is expressed as follows:

$$F(t) = \Delta P_{comp}(t)/R_{exit} = \Delta P_{ind}(t)/R_{exit} = \Delta P_{ind}(t)/R_2 \quad \text{(Eq.10)}$$

where both equalities $\Delta P_{comp}(t)=\Delta P_{ind}(t)$ and $R_2=R_{exit}$ are taken into account. Now the right-hand part of the expression (10) can be substituted into general expression (9) and calculated by the processor with the use of an appropriate algorithm providing the integration. Because the processor acquires the signals S(t) reflecting the kinetics of the pressure change $\Delta P_{ind}(t)$ in accordance with the equation (6), one obtains the final expression which shows the relationship between the output signals of the sensor system and the actual dose D(t) of the fluid delivered by any simple device of the first group at any moment t>0 of the cycle:

$$D(t) = \frac{1}{R_{exit}} \int_0^t \Delta P_{ind}(t)\,dt = \frac{\alpha\beta}{R_2} \int_0^t dt S(t) \qquad \text{(Eq. 11)}$$

It does not matter in this particular example whether the section 8 is made in the traditional form of the syringe made of hard materials (see FIG. 19 and FIG. 5 for details) or it comprises at least one elastic bag or pillow which may be compressed or expanded by any other means (FIG. 20, FIG. 21, and FIG. 22). All that is used is the relationship between the stiffness parameter $\alpha$ of the expandable indicator 9 and other parameters of given device. Taking into account that both the amplitudes of the pressure pulses $P_0$ created by the system 14 and the desirable doses of the fluid $D_0$ may vary in different cycles, only average values of $P_0$ and $D_0$ are used to answer quantitatively whether the parameter $\alpha$ is low or high. The parameter $\alpha$ relates to the change of the indicator's volume, which in accordance with the equation (4), can be expressed as: $\Delta V_{ind}(t)=\Delta P_{ind}(t)/\alpha$. The average value $P_{avr}$ substituted into this expression instead of $\Delta P_{ind}(t)$, provides the average volume change $\Delta V_{avr}$ which must be further compared with the average fluid dose $D_{avr}$. Two different cases may exist according to results of this comparison, and, correspondingly, two different approaches are considered below.

F-1. Method for the Case of Low Stiffness Factor of the Indicator Section

It follows from the above that in a simple device of the first group the value of the parameter $\alpha$ is considered to be low when the condition $\Delta V_{avr} \gg D_{avr}$ is fulfilled. This condition means that during cycle time $T_c$ the indicator section of the reservoir loses only a small part of its expanded volume $\Delta V_{avr}$, and, accordingly, the elevated pressure inside the reservoir remains relatively constant during $T_c$. This situation is reflected in both quasi-rectangular diagrams shown in top view of FIG. 17. Due to the relatively constant $P_0$ of each selected cycle, the equation (11) has a linear solution represented by the equation (12) below and shown in bottom view of FIG. 17, because neither pressure pulse $\Delta P_{ind}(t)=P_0$ in the indicator 9 nor output signals S(t) of sensor system 16 can change in the active period $T_{up}<t<T_c$. This statement is mathematically expressed with following formula representing the relationship between the actually delivered dose D(t) and the relatively constant value $P_0$ related to the pressure in the reservoir during the current cycle:

$$D(t) = \frac{P_0}{R_2}\left(t - \frac{T_{up}}{2}\right) = \frac{\alpha\beta S}{R_2}\left(t - \frac{T_{up}}{2}\right) \qquad \text{(Eq. 12)}$$

In most cases of practical calculations the short transition time can be neglected if $T_{up} \ll T_c$. However, one can see that short transition time $T_{up}$ is taken into account in the precise solution represented by the expression (12). It also reflects the fact that even single reading S, provided by the sensor system 16 at any voluntary chosen moment within the interval $T_{up}<t<T_c$, can be enough to determine both the constant excessive pressure $P_0$ created during the current cycle and the function D(t), representing the actual dose delivered.

The equation (12) can be used for obtaining an expression that predicts the final moment $T_c$ corresponding to the equality of the dose actually delivered D(t) and the desirable dose $D_0$ predetermined by the delivery program. A prediction of the final time-point results from the comparison of calculated function D(t) with the desirable dose, as follows:

$$D_0 \frac{R_2}{\alpha\beta S} + \left(\frac{T_{up} - T_{down}}{2}\right) = T_c \qquad \text{(Eq. 13)}$$

Therefore, the conclusion is that, in the case of low stiffness factor $\alpha$ of the expandable indicator 9, the processor is only required to acquire at least one signal from the sensor, and this is enough to accomplish the entire task related to the third step of the general method of the invention. Both the signal acquisition and the following mathematical prediction provided by the formula (13) must be complete at the time $t \leq T_c$. The diagrams in FIG. 17 demonstrate that the shortest cycle time $T_c$ cannot be less than minimum time $1/f_0$ required to take one reading of the signal S and to process it. The algorithm based on the formula (13) does not require very high frequency $f_0$. For example the $f_0$ about 1 Hz may be enough.

The calculation of the predicted time $T_c$ means the end of the third step of the method. However, this calculation takes only time $1/f_0$ which is normally shorter than $T_c$. That is why in the case of simple devices having low parameter $\alpha$, the beginning of the last step requires performing additional actions. After the moment $T_c$ is calculated, the processor must wait for the moment of the real time corresponding to the predicted $T_c$. Only when such moment of the real time is detected the processor sends the terminating signal to the system 14. It may be desirable that the decrease of the pressure in the reservoir occurs in a short time $T_{down} \ll T_c$ so that final relaxation process does not contribute significantly into the precision of the dose delivered. However, the predicting expression (13) shows that this precision can be additionally improved if both transition times $T_{up}$ and $T_{down}$ are known in advance as factory pre-set parameters.

Two dosing diagrams shown in bottom view of FIG. 17 demonstrate how the correct determining of $T_c$, predicted by the expression (13) for simple devices having low parameter $\alpha$, provides stable dosing of the fluid notwithstanding rather high variations of the amplitude $P_0$ of the pressure pulses produced in two different cycles.

F-2. Method for the Case of High Stiffness Factor of the Indicator Section

In some embodiments a simple device, considered in the section F-1, may become a device with relatively high stiffness factor $\alpha$ of the expandable indicator section of the reservoir. For example, this may happen in an emergency situation when a patient needs to increase the dose of the drug many times so that desirable $D_0 \gg D_{avr}$. The result may be that new $D_0$ is comparable with $\Delta V_{avr}$ and previous condition $\Delta V_{avr} \gg D_0$ becomes not valid. In this case the reservoir may lose a substantial part of its expanded volume during the same cycle, and the plateau $\Delta P_{ind}(t)$ of the pressure pulse can become unstable in time as shown in top view of FIG. 18. The quantitative definition given above takes into account this situation where there is a high stiffness parameter $\alpha$.

Figure 18:
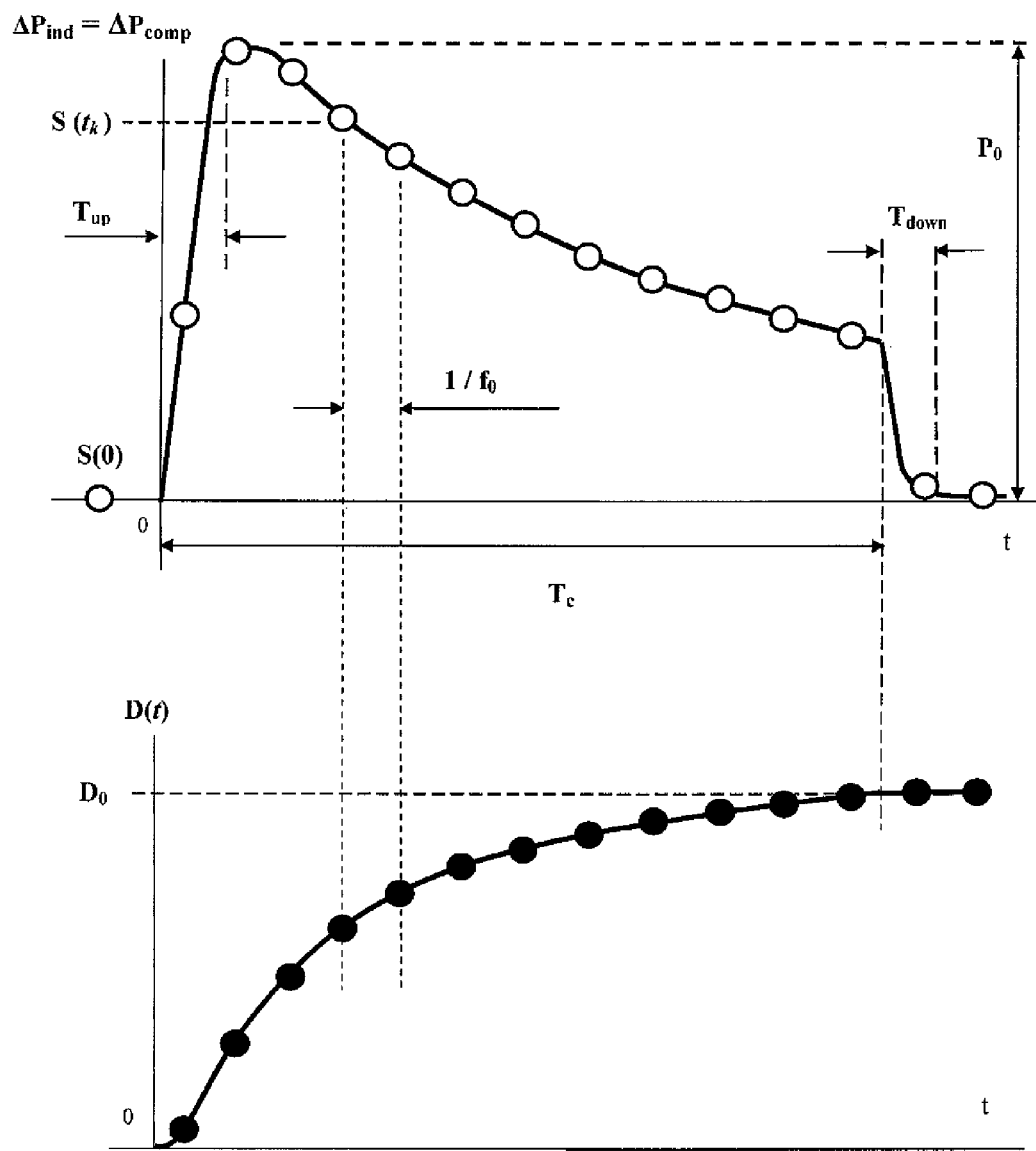
FIG. 18 depicts an example of a rather unstable plateau of a pressure pulse occurring in the compression section of the reservoir of an embodiment of a device of the invention (top view), and the corresponding time-dependence of the fluid dose delivered to the exit opening (bottom view). White circles correspond to the readings of output signals produced by the sensor system. For simplicity, these output signals are shown so as if their scale coincides with the pressure scale of the indicator section of the reservoir. Black circles show result of integrating the sensor's signals to urge the fluid dose delivered to the exit opening at corresponding moments of the time.

Other reasons may result in a high value α as well. However, independent on the particular reason, the previous predicting algorithm based on the expression (13) may not be ideal in this case of providing good precision of the drug delivery. The integral expression (11) is still valid even in this case. That is why in order to obtain the highest dosing precision, the processor should receive maximum information with as high frequency $f_0$ of measurements of signals S(t) as possible. In this case during the entire cycle the processor acquires more than one digital signal so that the actual integral dose may be represented by a discrete sum consisting of many members L(t)>1. White circles in the top view of FIG. 18 show multiple signals S(t) acquired in the case of an unstable process $\Delta P_{ind}(t)$. With higher frequency of sampling, the more L(t) is obtained during the cycle, resulting in higher final precision based on the following integral expression:

$$D(t) = \frac{\alpha\beta}{R_2}\int_0^t dt S(t) \cong \frac{\alpha\beta}{f_0 R_2}\sum_{k=1}^{L(t)} S(t_k) = D(t_L) \quad \text{(Eq. 14)}$$

This expression tells that the calculated sum $D(t_L)$ depends on the number L(t) of acquired signals as shown by black circles in the bottom view of FIG. 18. In order to determine the final moment $T_c$ one algorithm directs the processor to repeat the following cyclic real time operations starting from the number L=1: (i) the sum $D(t_L)$ is calculated first in accordance with the expression (14); (ii) then the difference $\Delta D(L) = D_0 - D(t_L)$ is calculated; (iii) if the $\Delta D(L)$ obtained at given L is positive then the processor adds 1 to the present L and returns back to the step (i) thus repeating the same cycle until $\Delta D(L) \leq 0$. The moment $T_c$ corresponds to such $t_L$ when the condition $\Delta D(L) \leq 0$ is fulfilled the first time. At this moment the third step of the method is complete and the processor begins to fulfill the last step terminating the cycle.

Comparison of expressions (12) and (14) shows that in the case of simple devices the integral constituting the numerator of the ratio (9) is proportional to the sum of all signals S(t) acquired while $T_c$ independent of whether factor α is low or high. In the first case an advantage of the expressions (12) and (13) related to low α is that this sum may contain the only signal. However, the advantage of last algorithm, related to high α and comprising multiple measurements and summation of more than one signals S(t) acquired, is that at L>>1 applicability and high precision does not depend on the exact kinetic shape of the pressure difference $\Delta P_{ind}(t)$. This means that in addition to spontaneous fluctuations of $P_0$, the shape of each pressure pulse is also allowed to be rather far from an ideal quasi-rectangular form. Moreover, in this case even the condition $T_{up} \ll T_c$ is not mandatory. Therefore, the system 14 forming pulses $\Delta P_{ind}(t)$ may be made extremely simple and cheap. The present description of the simple algorithm of digital integration is provided as an example only. Anyone skilled in the art of mathematical treatment of digital signals knows how the precision of such algorithm can be further improved if one uses the first and highest derivatives calculated from the same sequence of measured signals S(t).

At the same time the major disadvantage of whole first group of simple devices of the invention is that the simple algorithms and their operation are not capable of self-control in regard to accidental or slow long-term changes of internal parameters of the whole delivery system. For example, the descriptions in both sections F-1 and F-2 assume that the exit hydraulic resistance $R_{exit}$ is stable in time and equal pre-set $R_2$. In order to control potential occlusion, such devices must be equipped with additional sensors. This problem is addressed by more advanced methods of operation applicable to more advanced and most advanced devices discussed below.

G. Methods for Drug Delivery with More Advanced Devices

Additional embodiments of the invention represent combinations of more advanced methods and devices of the invention wherein the opening 3, connecting the flow passage 12 with the reservoir 1, can be located on the wall of the indicator section 9 of the reservoir as it is shown in FIG. 20, FIG. 21, and FIG. 22. It can also be also desirable that relationships of a few basic parameters, such as resistances $R_1$ and $R_2$, the stiffness factor α of the indicator, and the highest frequency $f_0$ of a sensor's signal acquisition satisfy one or more of a few additional requirements described below.

One additional feature is that both resistances $R_1$ and $R_2$ can be represented by corresponding quantitative expressions containing given ratio $\alpha/f_0$ as follows:

$$R_1 = n\alpha/f_0 \text{ and } R_2 = m\alpha/f_0 \quad \text{(Eq.15)}$$

where both n and m may be chosen positive numbers exceeding 1. The fulfilling of the first condition (15) is desirable in order to bring the rate $f_0$ of signal acquisition in accordance with an algorithm treating these signals. However, in order to obtain improved performance of devices of the second and the third groups, a second additional requirement provides desirable relationships of these numbers:

$$\frac{n}{m} \geq \frac{1}{m-1} \quad \text{(Eq. 16)}$$

In order to increase the range of operating parameters of more desirable embodiments, it may be desirable that $R_1$ is close to $R_2$ by an order of magnitude, and at least $R_1$ is not less than about 0.05 $R_2$ and not more than about 200 $R_2$. It may be desirable that the ratio $R_1/R_2$ is between about 0.25 and about 40. Alternatively, it may be desirable that the ratio $R_1/R_2$ is between about 1 and about 10. For example, in accordance with linear hydraulic characteristics of both resistors shown in FIG. 9, one can choose $R_1 = 24\alpha/f_0$ (line (b) with n=24) and $R_2 = 7\alpha/f_0$ (line (c) with m=7), thus providing the ratio $R_1/R_2$ close to about 3.5. It can be demonstrated that such particular choices, satisfying both conditions (15, 16), is in the range suitable for detection of a potential occlusion. However, other combinations of n and m are permitted by the conditions (15, 16) as well, and may be used in different embodiments.

Similar to simple devices described above, other embodiments allow different choices of mechanisms applying the force to the fluid in the compression section of the reservoir. However, in many of these cases it may be desirable that any particular mechanism be capable of: (a) providing a short time $T_{up}$ of the first pressure transition so that $T_{up}$ corresponds to the limitation of the following expression at least by an order of magnitude:

$$T_{up} \ll \frac{n}{f_0(1 + n/m)} \quad \text{(Eq. 17)}$$

(b) providing after a transition $T_{up}$ such pressure plateau $P_0$ in the compression section, which is relatively stable during the period $T_c$ of any delivery cycle; and (c) providing the ability to fulfill from time-to-time a special command of the controlling processor 17 resulting in the creation of the negative pressure change in the compression section of the reservoir during the special self-calibration procedure ordered by the program of the operation. To fulfill conditions stated above in the present paragraph, it may be desirable that the compressing mechanism of the sub-system 14 be chosen to be similar to the one shown in either FIG. 19, representing the syringe made of hard materials, or FIG. 21, FIG. 22, and FIG. 22 wherein the walls of the compression section of the reservoir are made at least partially of a soft material either resilient or not. It may be desirable also that the more desirable embodiments discussed in this section are designed to use fully replaceable cartridges wherein both compression and indicator sections of the reservoir are made of resilient materials as shown in FIG. 6. A reason that factory pre-filled replaceable cartridges are desirable, is that they can reduce or eliminate the possibility of internal or external contamination and thus prevent any change of factory pre-set very stable resistance $R_1$, saved in the processor's memory as an individual parameter of each particular cartridge. In this case only some changes of output resistance $R_{exit}$ can be expected if the occlusion occurs.

Figure 23:
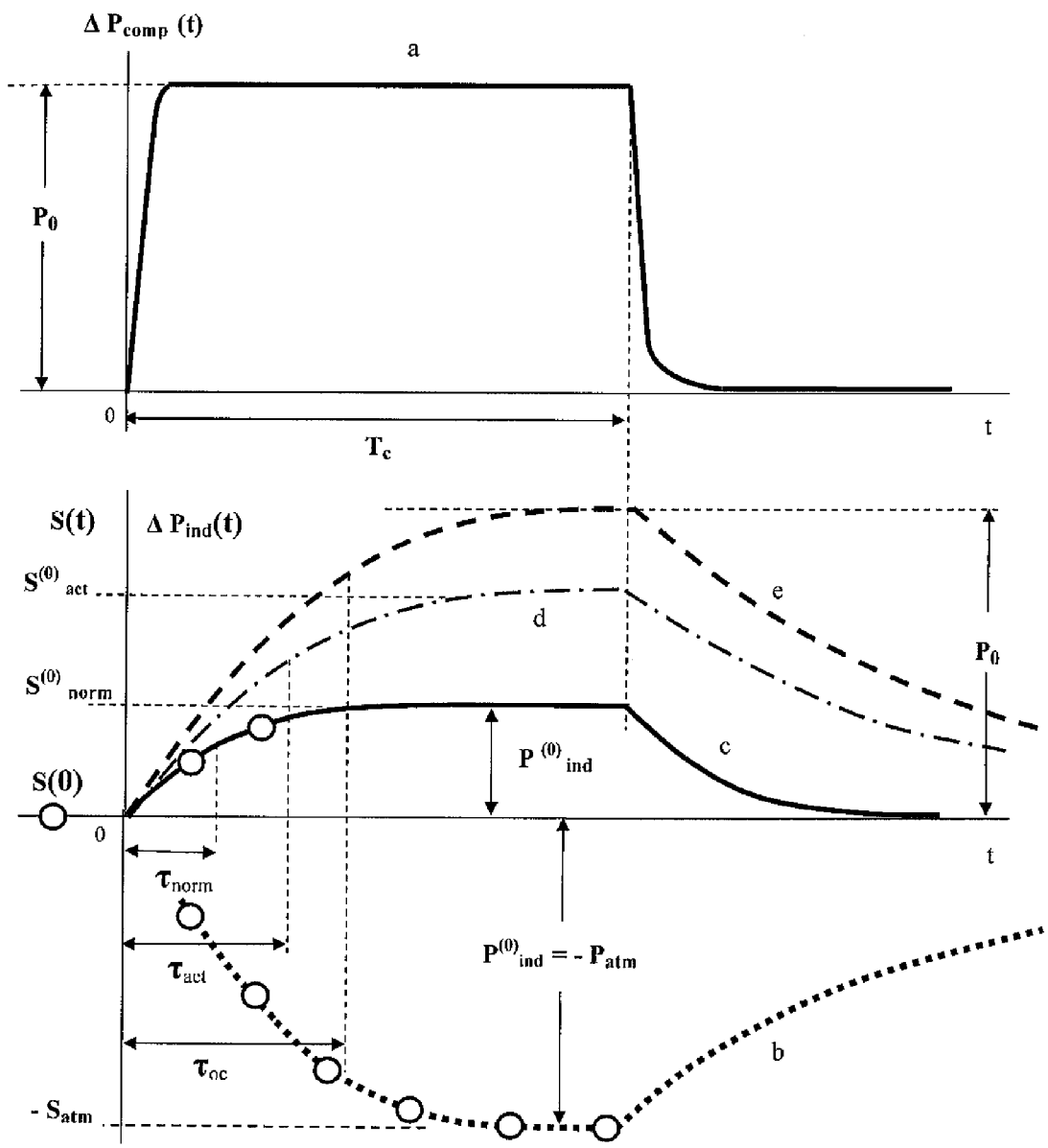
FIG. 23 depicts typical diagrams of an embodiment of the invention. The top view shows the shape of pulses of the pressure inside the compression section of the reservoir. The bottom view depicts shapes of pressure pulses in the indicator section of the reservoir and corresponding output signals of the sensor system related to different states of the output hydraulic resistance of the entire fluid delivery device. For simplicity, output signals of the sensor system are shown as if their scale coincides with the pressure scale of the indicator section of the reservoir.

In accordance with features listed in the preceding paragraphs the diagram of the pressure change in the compression section of more desirable embodiment is represented by a well formed quasi-rectangular pulse exemplified by the top curve (a) in FIG. 23, which is similar to diagrams of simplified devices in FIG. 17. Diagrams of pressure change in the indicator section of certain desirable embodiments can differ substantially from those of simple devices, because now the fluid flow arrives at indicator 9 through the resistor 5 having high resistance $R_1$ and goes out through the flow passage 12 having the output resistance $R_{exit}$. In contrast to simple devices of the invention, in more complex embodiments, the parameter $R_{exit}$ can be considered according to the expression (5) taking into account certain long-term processes changing this parameter unpredictably. The algorithm of more complex methods takes also into account that both incoming and outgoing flows in the indicator section of the reservoir depend on time differently as it follows from exact equations considered below.

In accordance with the equation (1) the magnitude $F_1(t)$ of the first fluid flow, arriving into the indicator after a short transition time $T_{up}$, may be expressed with the use of the resistance $R_1$ and the difference of absolute fluid pressures in compression 8 and indicator 9 sections. Also nothing can change if one adds and immediately subtracts the external atmospheric pressure. These mathematical operations, taking also the equations (3) and (4) into account, result in following equation which is valid at any time $t > T_{up}$:

$$F_1(t) = \frac{P_{comp} - P_{atm} + P_{atm} - P_{ind}(t)}{R_1} = \frac{P_0 - \Delta P_{ind}(t)}{R_1} \quad \text{(Eq. 18)}$$

At the same time the magnitude of the second fluid flow leaving the indicator section 9 and passing through the flow passage 12 is described by the following expression:

$$F_2(t) = \frac{P_{ind}(t) - P_{atm}}{R_{exit}} = \frac{\Delta P_{ind}(t)}{R_2 + R_3} \quad \text{(Eq. 19)}$$

where the additional output resistance $R_3$ is close to zero in the very beginning of the device's operation but it can increase spontaneously during long-term operation of the device. The reason for that may be an accidental damage of the flow passage, caused by unskillful user, or its occlusion either partial or insurmountable one.

It can be appreciated that the speed of volume expansion of the indicator section 9 is equal the difference of intensities of entering and exiting fluid flows. Both equations (18) and (19) allow transforming this statement into explicit form of the following differential equation where the expression (4) is taken into account as well:

$$\frac{d}{dt} \Delta V_{ind}(t) = \frac{d}{\alpha dt} \Delta P_{ind}(t) \quad \text{(Eq. 20)}$$

$$= \frac{P_0}{R_1} - \Delta P_{ind}(t) \left( \frac{1}{R_1} + \frac{1}{R_2 + R_3} \right)$$

The inventor has found a rigorous solution of equation (20), which is valid during time period $0 < t < T_c$, and is provided by the following expression:

$$\Delta P_{ind}(t) = \frac{P_0}{\left(1 + \frac{R_1}{R_2 + R_3}\right)} \left[ 1 - \exp\left\{ -\frac{\alpha t}{R_1} \left(1 + \frac{R_1}{R_2 + R_3}\right) \right\} \right] \quad \text{(Eq. 21)}$$

At the same time the equation (6) shows that output sensor's signals $S(t)$, reflecting the kinetics of solution (21), obey simple exponential law as follows:

$$S(t) = S^{(0)} \left[ 1 - \exp\left\{ -\frac{t}{\tau_{act}} \right\} \right] \quad \text{(Eq. 22)}$$

where the first independently measurable parameter of every cycle is the amplitude $S^{(0)}$ of the exponential kinetic curve which is correlated with both the amplitude of the pressure increase in the indicator $P^{(0)}_{ind}$ and corresponding maximum expansion of its volume $\Delta V^{(0)}_{ind}$ expressed as:

$$S^{(0)} = \frac{\Delta V^{(0)}_{ind}}{\beta} \quad \text{(Eq. 23)}$$

$$= \frac{P^{(0)}_{ind}}{\alpha \beta}$$

$$= \frac{P_0}{\alpha \beta \left(1 + \frac{R_1}{R_2 + R_3}\right)}$$

$$= \frac{P_0 \tau_{act}}{\beta R_1}$$

The second independently measurable parameter is the actual value of time-constant $\tau_{act}$, related to the same cycle and defining the actual exponential kinetics. This time-constant is correlated with other parameters of more complex devices:

$$\tau_{act} = \frac{R_1}{\alpha \left(1 + \frac{R_1}{R_2 + R_3}\right)} = \frac{\tau_{oc}}{\left(1 + \frac{R_1}{R_2 + R_3}\right)} \quad \text{(Eq. 24)}$$

where the parameter $\tau_{oc}$ is to be considered now as the device's constant related to the state of an insurmountable occlusion and discussed in more details herein below.

Examples of exponential kinetics of signals $S(t)$ recorded in different cycles are shown as curves (b), (c), (d), and (e) in bottom part of FIG. 23. Due to conditions of equations (15) and (16) being fulfilled, the pressure in the indicator section changes more slowly than that in the compression section of the reservoir. It has been unexpectedly discovered that the value $\tau_{act}$ does not depend on the pressure amplitude $P_0$. That is a reason why, even if compressing system 14 is very simple and can potentially cause wide variations of $P_0$ in different cycles, the measurements of $\tau_{act}$ can provide very precise information about the actual values of hydraulic resistance $R_{exit}$ of the flow passage at the time of each cycle, especially because the value $R_1$ is known and can be very stable, especially in the case of fully replaceable cartridges. Due to the mechanical nature of the parameter $\alpha$, which must be individually determined for every particular cartridge, it can drift in time only slowly because of very slow aging of the elastic materials. The complex methods of the operation of other devices include procedures for periodic self-calibration, which decreases or eliminates uncertainty related to potential drifts. Actually this means that the exact value of the $\alpha$ can always be known and stored in the processor's memory.

It can be appreciated that to determine the parameters of exponential kinetics of the expression (22), namely the parameter $S^{(0)}$ and $\tau_{act}$, at least two signals $S(t)$ must be acquired and treated by the processor during the initial part of the exponential pressure change in the indicator section. The analysis of exponential curves is quite standard mathematical procedure which does not need to be separately discussed further herein. It can be appreciated that this procedure can be incorporated into mathematical algorithms of more complex embodiments. It also may be apparent that the precision of the determination of parameters of exponential curves may be further increased if the processor acquires and treats more than two signals $S(t)$ during the time $T_c$. Examples of desirable discrete signals transferred to the processor are shown by white circles placed on curves (b) and (c) in FIG. 23.

It can be desirable that every time when either a new replaceable cartridge is installed or non-replaceable cartridge is refilled, a patient uses the control panel 18 and orders the processor to perform self-calibration of all internal parameters of the device except the resistance $R_1$ which is factory pre-set parameter. The start of self-calibration procedure requires that the sterile cap 35 (see FIG. 7 for example) is on in order to lock the exit opening of the flow passage 12 so that artificial situation of insurmountable occlusion takes place. In this case the output resistance $R_{exit} \approx R_3$ becomes so high indefinitely that $R_3 \gg$ both $R_1, R_2$.

Self-calibration begins at t=0 when the system 14 fulfills the special signal of the processor and expands the compression section so much that absolute pressure in the reservoir drops to about zero. That corresponds to negative value $P_0 = -P_{atm}$, which is known rather well. All necessary corrections in regard of the fluid's vapor pressure and the altitude of current geographic point above the sea level can be easily calculated by the processor. After t=0 the pressure in the indicator section reacts exponentially (see curve (b) in FIG. 23) with the actual time-constant $\tau_{act}$ equal $\tau_{oc}$, which is a characteristic parameter of a given occluded cartridge. Simultaneously with the slowed-down exponential increase of the pressure inside the indicator section, the processor acquires and treats as many discrete signals $S(t)$ as may be necessary to be sure that this pressure reaches a high and stable value. This occurs at $t \gg \tau_{oc}$ when the exponential term in both expressions (21) and (22) drops to zero and the content of their square brackets becomes equal 1. Multiple acquisition of signals $S(t)$ allow high precision measuring of characteristic value $\tau_{oc}$ which is further saved in processor's memory. It also follows from the expression (21) that due to intentionally created situation $R_3 \gg R_1, R_2$ the change of indicator's pressure obtained at that time is equal $P^{(0)}_{ind} = P_0 = -P_{atm}$, whereas the corresponding maximum signal $S^{(0)}$ measured by sensor system is equal to: $-S_{atm}$. Both these measured values must be also saved in processor's memory.

After completing of all these actions, the processor's memory contains the following values: $R_1$, $P_0 = -P_{atm}$, $S^{(0)} = -S_{atm}$ and $\tau_{act} = \tau_{oc}$ related to special case $R_{exit} \approx R_3 \gg R_1, R_2$. The immediate result following from the expression (24) is the determining the parameter $\alpha$ reflecting the stiffness of the indicator section of given cartridge at current moment of the time:

$$\alpha = R_1 / \tau_{oc} \quad \text{(Eq.25)}$$

The expression (23) may be used next to determine the parameter $\beta$ as follows:

$$\beta = \frac{P^{(0)}_{ind}}{\alpha S^{(0)}} = \frac{P_{atm} \tau_{oc}}{R_1 S_{atm}} \quad \text{(Eq. 26)}$$

After that all constants of the device become known to the processor, and it orders the system 14 to restore normal pressure in the reservoir in order to complete the calibration. The customer can be promptly supplied with the personal information that the locking cap 35 can be now removed and normal long-term operation of the device can start. In the course of long-term operation, the customer may order the processor to repeat the self-calibration procedure from time-to-time in order to correct the values of device's constants if potential long-term changes take place in the device. In the case of any abnormal behavior of the device the direct knowledge of changes occurring with separate values $\alpha$ and $\beta$ may be very useful to detect easy and rapidly what has happened to the device. However, for normally functioning devices the knowledge of only two primarily calibrated parameters $S_{atm}$ and $\tau_{oc}$ are needed.

Normal processes of the drug delivery begin after completing the self-calibration when the cap 35 is removed and the exit opening 13 is brought in the contact with patient's body. In this case the first and the last step of the general method remain the same as they have been described in the section F-1 related to simple devices having low parameter $\alpha$. The third step developed to operate more complex embodiments can use different predictive algorithms that calculate the expected moment $T_c$ corresponding to termination of the cycle. There are two reasons for that. The first reason is that, according to expression (24), the time-constant $\tau_{act}$ measured in each cycle reflects both the actual state of the delivery process and actual output resistance $R_{exit}$. Normally, in the very beginning of the operation there is no occlusion at all. So, initial $R_3 \approx 0$ and $R_{exit} = R_2$ in accordance with the expression (5). This corresponds to the lowest $\tau_{act} = \tau_{norm}$ and the lowest amplitudes of both the pressure $P^{(0)}_{ind}$ in the indicator and corresponding signal $S^{(0)}_{norm}$ as shown by the exponential curve (c) in FIG. 23. If during long-term operation, a partial occlusion takes place, the $R_3 \neq 0$ any more, and the output hydraulic resistance increases so that $R_{exit} = R_2 + R_3 > R_2$. Correspondingly to that all $\tau_{act}$, $S^{(0)}$ and $P^{(0)}_{ind}$ become higher as the curve (d) shows in FIG. 23. This increase of $R_{exit}$ causes the decrease of the magnitude of flow $F_2$ exiting the device. However, in order to keep the dose constant, this decrease can be automatically compensated by corresponding increase of $T_c$ until $\tau_{act}$ calculated by the processor's algorithm is in the allowed range $\tau_{norm} \leq \tau_{act} < \tau_{oc}$. So, in this range, the device is capable of self-recovering partial occlusions, and there is no need to disturb a patient even in the case of modestly high occlusion. The unlikely event of the insurmountable occlusion shown by the curve (e) in FIG. 23 corresponds to the equality $\tau_{act}=\tau_{oc}$, where the value $\tau_{oc}$ is already stored in the memory. When processor's algorithm detects such equality, then it must stop further operation and produce an alarm signal informing a patient promptly. This explains the first reason why the mathematic algorithm of the more complex embodiments can desirably be very different from simple expressions (13, 14) disclosed herein above. The expressions provided below show examples of how a self-recovering algorithm can work and the correct $T_c$ can be determined.

It has been already mentioned before that at least two signals S(t) must be acquired at the period $0<t<T_c$. It can be desirable that measurements are made in a limited time period $0<t<\tau_{oc}$ related to the beginning of each cycle, in order to obtain two actual parameters $\tau_{act}$ and $S^{(0)}$ corresponding to the current cycle in accordance with the kinetics of the expression (22). When these measurements are completed, the kinetics (22) of outgoing fluid flow $F_2(t)$ is fully determined in the entire time period $0<t<T_c$ as follows:

$$F_2(t) = \frac{\Delta P_{ind}(t)}{R_{exit}} = \frac{P_{atm}S^{(0)}}{R_1 S_{atm}}\left(\frac{\tau_{oc}}{\tau_{act}}-1\right)\left[1-\exp\left\{-\frac{t}{\tau_{act}}\right\}\right] \quad \text{(Eq. 27)}$$

Due to high resistances $R_2$ and $R_1$, the flow $F_2(t)$ does not stop immediately after the pressure drop occurring at the moment $T_c$ in the compression section of the reservoir. This delay occurs because the elevated pressure in the indicator remains non-zero for some while after $T_c$, and the fluid is moving exactly as it is shown in the bottom view of FIG. 2. The inventor has discovered that in the framework of hydraulic scheme shown in FIG. 20 and FIG. 21 the flow $F_2(t)$ decays after $T_c$ exponentially with the same time-constant $\tau_{act}$, which has been already determined before $T_c$, namely as:

$$F_2(t) = \frac{P_{atm}S^{(0)}}{R_1 S_{atm}}\left(\frac{\tau_{oc}}{\tau_{act}}-1\right)\left[1-\exp\left\{-\frac{T_c}{\tau_{act}}\right\}\right]\exp\left\{\frac{T_c-t}{\tau_{act}}\right\} \quad \text{(Eq. 28)}$$

This slow decay occurs at $t>T_c$ (see curves (b, c, d, e) in FIG. 23), and can contribute a substantial part of the final dose delivered to the exit opening. In order to determine the dependence of the final dose on the duration $T_c$ of the cycle, one can substitute each of two equations (27) and (28) into the general integral expression (9), to calculate each integral separately, and then to summating both integral expressions. After summating these two integrals found analytically one obtains the following result:

$$D(T_c) = \frac{P_{atm}S^{(0)}}{R_1 S_{atm}}\left(\frac{\tau_{oc}}{\tau_{act}}-1\right)T_c \quad \text{(Eq. 29)}$$

The final expression (29) shows a natural result that the fluid dose actually delivered to the exit opening is proportional to the product of both the cycle duration $T_c$ and the maximum pressure $P^{(0)}_{ind}$ in the indicator, which is reflected by the amplitude $S^{(0)}$ of sensor's exponential kinetics while this cycle. The second consequence demonstrated by the expression (29) is that the non-zero fluid dose may be delivered in the finite time $T_c$ only if there is no insurmountable occlusion and $\tau_{act}<\tau_{oc}$. In accordance with the result (29) the predicted time $T_c$ is to be calculated by the processor as:

$$T_c = \frac{\tau_{act}D_0 R_1 S_{atm}}{(\tau_{oc}-\tau_{act})P_{atm}S^{(0)}} = t_{end}-t_{st} \quad \text{(Eq. 30)}$$

The resulting expression (30) is produced in accordance with general formula (9) wherein actual output resistance $R_{exit}$ is determined during the cycle and then is directly substituted into the denominator of the expression (9). The same actual $R_{exit}$ is indirectly substituted into an analytic expression of the integral constituting the numerator of the expression (9) because it follows from the comparison of expressions (30) and (24). Because the dose $D_0$ is predetermined by the delivery instructions, and all other variables and parameters in the expression (30) have been either determined during calibration of the device or measured during the current cycle, the calculation of the predicted time $T_c$ related to this cycle is possible if $(\tau_{oc}-\tau_{act})>0$. The only non-analytic case excluding determining the $T_c$ is at least approximate equality $\tau_{oc}\approx\tau_{act}$ corresponding to an insurmountable occlusion, wherein actual $R_{exit}$ exceeds a certain predetermined level. If the algorithm detects this situation, the time $T_c$ cannot be calculated, and the processor generates an alarm signal. However, the system can self-recover fully even in cases of such high occlusion that the positive term $(\tau_{oc}-\tau_{act})>0$ becomes much smaller than $\tau_{act}$. In order to reach this aim, the processor calculates high $T_c$ in accordance with expression (30), then it waits until the real time coincides with determined moment $t_{end}=T_c+t_{st}$, and transmits the ending signal to the system 14 after corresponding delay. The result of such operation in time is that actually delivered dose is always kept either precisely equal or very close to desirable $D_0$.

To provide another example, consider the previous quantitative example where values of initial resistances were chosen as follows: $R_1=24\alpha/f_0$ and $R_2=7\alpha/f_0$. For simplicity consider that the initial contact resistance is as low as $R_3=\alpha/f_0$ so that the initial ratio $R_1/(R_2+R_3)=3$. According to expression (24) $\tau_{oc}=24/f_0$ and normal time constant corresponding to non-occluded state is $\tau_{act}=\tau_{norm}=6/f_0$. Such a situation provides the sensor system with the ability to measure at least two and more desirable up to 10-12 signals S(t) during the exponential kinetics after $t>0$. Mathematical treatment of these signals shows that their amplitude $S^{(0)}$ corresponds to the maximum pressure in the indicator, which is now only $P_0/4$ in accordance with expression (23). In order to deal with real numbers let us think also that the normal non occluded delivery of desirable dose $D_0$ requires average time $T_c=10$ s.

Consider that after some time an occlusion of the exit opening occurs so that the resistance $R_3$ increase to 113 times and is now $R_3=113\alpha/f_0$. Because $R_1$ and $R_2$ remain the same as before, the new ratio is $R_1/(R_2+R_3)=0.2$ and the corresponding time-constant increases to $\tau_{act}=20/f_0$. The amplitude $S^{(0)}$ increases as well because in the occluded state the maximum pressure in the indicator becomes $P_0/1.2$. In accordance with these numbers the expression (30) predicts that the actual dose delivered will be the same $D_0$ as before if the algorithm of the occluded device changes the $T_c$ from normal 10 s to much longer time about 80 s.

The same expression (30) demonstrates also that it can take into account that a simple system 14 may be a potential source of rather substantial variations of the pressure amplitude $P_0$ in the compression section of the reservoir. For example, if in a certain cycle the actual $P_0$ exceeds its average value, ordered by the processor, for example, 5 times, the corresponding measurement of the signal $S^{(0)}$ increases the same 5 times and the device terminates this particular cycle in shorter time $T_c=2$ s instead of the average of 10 s, thus keeping a stable output dose. In the opposite case the termination of another cycle can be done with longer time $T_c=50$ s if the actual $P_0$ is 5 times less than ordered average value.

It can be appreciated that all the quantitative estimates provided in the three previous paragraphs are given as examples only, and any particular realization of the present invention may also posses quite different quantitative features. However, even these limited examples are enough to illustrate that devices of the present invention, being supplied with the only sensor and a simple squeezing-out system, can perform better in than previously known, more complicated devices of the prior art. It can be clear also that an advantage of the invention, namely its ability for self-correction in changing internal and external environments, depends on the precision and sensitivity of the sensor because only the sensor supplies the processor with the information. The more information comes to the processor, and the higher precision of this information, the "smarter" decisions can be made. For example, some estimates show that other embodiments supplied with a high precision sensor may, in principle, withstand successfully a level of occlusion which exceeds the resistance $R_2$ more than few hundred times, and may be even more than one thousand times. In addition it may be noted that abilities of more complex devices of the invention discussed above become possible if the ratio $R_1/R_2$ is not too low and is not too high as one can easily see from the analysis of the expression (24). That explains the purposes of conditions (15) and (16) restricting both upper and lower limits of this ratio.

At the same time there are few minor disadvantages which are inherent for all devices built on the basis of more desirable scheme shown in FIG. 20 and FIG. 21. These disadvantages are not critical but it can be better to decrease or eliminate them. The first one is that a patient needs to be directly involved in the calibration procedure, namely from time-to-time he or she must participate in this operation by putting the cap 35 on and off. The second is the necessity to rely upon the stability of factory pre-set resistance $R_1$ because the system itself has no means to control $R_1$. The last one is that potentially low level residual pressure $P_{res}$ may remain in the reservoir after the end of the cycle if the driving force system 14 has too low precision because of excessive simplicity as shown, for example, in FIG. 24, curve (a). If this is a case it may lead to very slow leak of the fluid between two cycles. Next section discusses the most complex devices and desirable methods capable of reducing or eliminating disadvantages listed above.

H. Methods for the Drug Delivery with Most Complex Devices

Additional embodiments of the invention are capable of either reducing or eliminating one or more of the minor disadvantages listed in the last paragraph of the previous section. For that they require such modification of the method which is applicable only to most advanced devices having slightly modified hydraulic system shown in FIG. 22. Being compared with the devices shown in FIG. 20 and FIG. 21, an additional feature of most advanced devices is that their flow passage 12 comprises a passive non-linear hydraulic element 32, which is controlled only by its own pressure drop $\Delta\pi$ and is capable of switching hydraulic resistance at a predetermined pressure drop $\Delta\pi=P_{val}$. It may be desirable that this element 32, made for example in the form of the ball valve shown in FIG. 7 and FIG. 22, is called hereinafter "the valve" for brevity. Its non linear hydraulic characteristics are represented by a dashed curve (a) in FIG. 9. It may be appreciated by those skilled in the art that the ball valve is shown in FIG. 7 for example only. Similar functionality can be also achieved in frameworks of valves having other design which doesn't contain the ball 33. For example, the other valve 32 can be formed by two parallel sheets made of silicon rubber so that the fluid must flow between said sheets in order to reach the exit opening. In this case such other valve containing no ball is closed if $\Delta\pi$ is less than the pressure of calibrated spring compressing these sheets slightly. At certain $\Delta\pi$ exceeding spring's pressure the fluid pushes elastic sheets apart and opens up a gap providing low hydraulic resistance. This example shows that particular technical design of similar valves is not a matter of a critical importance if following points are satisfied: (i) the valve takes opened state at certain pressure drop $\Delta\pi$ equal fixed $P_{val}$ calibrated by the manufacturer and stored in processor's memory; (ii) at any $\Delta\pi>P_{val}$ the hydraulic resistance $R_{val}$ of the valve obeys at least the condition $R_{val}<R_2$, and preferably $R_{val}$ is low in comparison with $R_2$; (iii) at any $\Delta\pi<P_{val}$ the valve is reliably closed so that $R_{val}>R_2$, desirably it is closed so that the resistance $R_{val}$ exceeds $R_2$ at least by the order of magnitude, and in other embodiments, $R_{val}$ exceeds both $R_1$ and $R_2$ more than two orders of magnitude; (iv) fixed $P_{val}$ is chosen to obey the relationship: $(P^{(0)}_{ind})_{avr}>P_{val}>P_{res}>0$, where $(P^{(0)}_{ind})_{avr}$ is an average pressure in the indicator section while the cycle, and $P_{res}$ is the maximum residual pressure which may potentially remain in the reservoir operated by given driving force system 14 (see diagram (a) in FIG. 24 for example).

It can be appreciated that the condition (iv) stated in the previous paragraph excludes any possibility of non controllable fluid leakage, because after the end of the cycle the low excess pressure in the reservoir $\Delta P_{comp}=P_{res}<P_{val}$ and the valve 32 is fully closed in accordance with the condition (iii). Thus, this valve resolves immediately one problem of three mentioned above.

The explanation of how the modified method resolves two other problems takes a little bit longer time. It should be noted preliminary that both the first (starting) and the last (ending) steps of the general method remain the same as they have been described in previous sections. All differences of the modified method are concentrated only in the third general step which controls the duration of each cycle by determining the specific ending moment $T_c$ executed while the last step. The previous important requirements of the third step, related to short time intervals $T_{up}$ and $T_{down}$ and high stability pressure plateau $P_0$, remain in effect. A modified method includes that after installation of new replaceable cartridge the processor's memory must be supplied with two very stable factory pre-set calibrated values, namely $P_{val}$ and $\alpha_{ini}$, where $\alpha_{ini}$ is the value of stiffness factor of the expandable indicator 9 in the very beginning of long-term operation. The first significant difference of the modified method is that the processor needs now to be supplied with much more information than before. That is a reason why the frequency $f_0$ should be chosen as high as possible, and the number of signals $S(t)$ acquired for the cycle's duration is at least five, and for better precision it is more desirable that this number exceeds five significantly. It will be shown below that complex kinetics of signals $S(t)$ produced by the modified devices consists of at least two different branches. Quantitatively good measurement of the first branch requires at least two signals acquired for initial time interval $0<t<t_1$, whereas good measurement of the second branch of said kinetics requires at least three signals, and more desirable significantly more than three signals, acquired in the time interval $T_c>t>t_1$. It may be desirable also that acquisition of a few additional signals is required after the end of the cycle. This last option will be discussed separately.

Also it may be noted that any real valve 32 passively controlled by its own pressure drop is always characterized by a certain pressure drop interval in which the transition occurs between closed and opened states. In order to simplify the mathematical model of the modified method of most desirable embodiments, in the present description this transition interval may be thought to be about zero, because the general scope of the modified method does not depend significantly on the width of this interval. Those skilled in math art should appreciate that standard corrections of the math algorithm can be always made if one needs to get better precision of the practical device by taking said width of actual transition interval into account.

In order to obtain the correct mathematical description of the fluid delivery processes provided by specific hydraulic system of FIG. 22 comprising the valve 32, first of all one needs to modify the expressions related to both fluid flows $F_1(t)$ and $F_2(t)$. Taking into account the finite hydraulic resistance $R_1$ communication between both the compression section 8 and the indicator section 9, one can transform the previous equation (18) so that arriving into indicator flow $F_1(t)$ is represented now in the following modified form which is valid at any time t>0:

$$F_1(t) = \frac{P_{comp} - P_{val} + P_{val} - P_{ind}(t)}{R_1} \quad \text{(Eq. 31)}$$
$$= \frac{P_0 - P_{val}}{R_1} - \frac{\Delta P_{ind}(t) - P_{val}}{R_1}$$

In contrast to that the output flow $F_2(t)$ in the flow passage 12 is locked completely if the valve 32 is in its closed state:

$$F_2(t) = 0 \text{ at } \Delta P_{ind}(t) < P_{val} \quad \text{(Eq. 32)}$$

Figure 24:
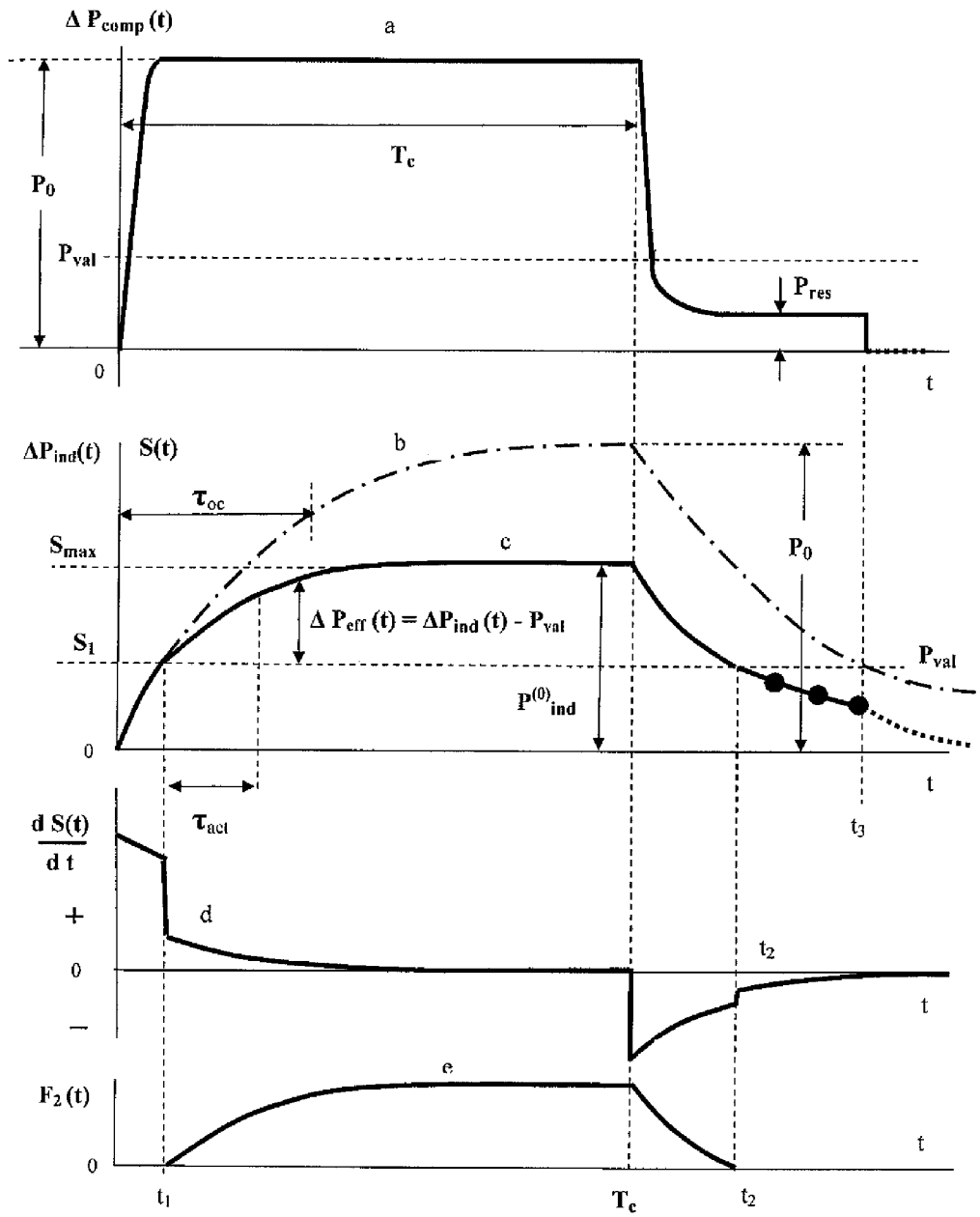
FIG. 24 depicts typical diagrams of an embodiment comprising the locking valve in the flow passage: (a) squeezing-out pressure during $T_c$ and low level residual pressure after $T_c$ in the compression section of the reservoir; (b, c) two merging branches of the pressure pulse in the indicator section of the reservoir and corresponding output signal of the sensor system in the case of either insurmountable occlusion (b) or normal work (c) which includes potential cases of partial occlusion. The diagram (d) shows a derivative of the sensor signal corresponding to curve (c). The diagram (e) represents the intensity of the fluid flow leaving the exit opening of the fluid delivery device. For simplicity output signals of the sensor system are shown so as if their scale coincides with the pressure scale of the indicator section of the reservoir.

When the valve 32 is switched to the opened state, its pressure drop $P_{val}$ is practically constant (see the curve (a) in FIG. 9). This drop reduces the pressure difference applied to output resistance $R_{exit}$ related to remaining part of the flow passage. The result is that non zero output fluid flow $F_2(t)$ depends now on the effective pressure change $\Delta P_{eff}(t) = \Delta P_{ind}(t) - P_{val}$ as follows:

$$F_2(t) = \frac{\Delta P_{eff}(t)}{R_{exit}} \quad \text{(Eq. 33)}$$
$$= \frac{\Delta P_{ind}(t) - P_{val}}{R_2 + R_3}$$
at $\Delta P_{ind}(t) > P_{val}$ Correspondingly, the initial part of each cycle consists of two kinetic branches. The first branch is described by the equations (31) and (32). The equation (32) applicable to the first branch corresponds to the presence of an insurmountable occlusion. The exponential kinetics of any entirely occluded device has been already expressed by the equation (22) where $\tau_{act} = \tau_{oc}$ and $S^{(0)} = P_0/(\alpha\beta)$. In some embodiments the artificially occluded state takes place only for a certain initial interval $0 < t < t_1$, because at the moment $t_1$, the pressure in the indicator 9 reaches the value $\Delta P_{ind}(t_1) = P_{val}$ and the valve 32 is switched to the open state. In FIG. 24 the solid line of diagram (b) shows only a real initial part of the occluded kinetics, whereas dash-dotted line shows its extrapolated continuation as if the valve 32 is never open. Actual switching of the valve 32 at the moment $t_1$ is demonstrated also by the diagram (e) in FIG. 24 where the non-zero output flow $F_2(t)$ begins only after the point $t = t_1$.

It is important to stress here that accordingly to Eq. 31 the exponential kinetics of the first branch at $0 < t < t_1$ involves only one hydraulic resistor $R_1$ which defines potential changes of important parameter $\tau_{oc}$. That is why measurements made before $t_1$ allow to take into account any change of capillary resistance $R_1$ caused, for example, by changes of a viscosity of the fluid which depends on current temperature of the device.

The second branch of the kinetics, represented by the curve (c) in FIG. 24, begins at the same $t_1$ immediately after the switching of valve 32. It can be appreciated that at the moment $t_1$ the sensor system 16 produces the following signal $S(t_1) = S_1$, which corresponds to the equality $\Delta P_{ind}(t_1) = P_{val}$. Because both $P_{val}$ and $\alpha_{ini}$ are calibrated constants of the device, the processor can use the expression (6) to calculate the following important parameter, which calibrates the readings of the sensor system in units of absolute pressure:

$$(\alpha_{ini}\beta) = \frac{P_{val}}{S_1} \quad \text{(Eq. 34)}$$

It is useful to note that in some embodiments, quantitative self-calibration of the sensor system occurs in the beginning of every cycle. This eliminates potential effects of either slow drift caused by temperature changes or material aging, or fast accidental changes of the sensor's characteristics, which may happen during long-term operation, possibly due to mechanical shocks or other unpredictable reasons.

Because the time $t_1$ in equation (32) is not valid any more, equation (33) can be used instead. The difference of two fluid flows, namely the difference of incoming $F_1(t)$ and outgoing $F_2(t)$, describes the speed of the volume expansion of the indicator 9 and leads finally to the following differential equation corresponding to the second branch of the delivery process:

$$\frac{d[\Delta P_{ind}(t) - P_{val}]}{\alpha dt} = \quad \text{(Eq. 35)}$$
$$\frac{P_0 - P_{val}}{R_1} - [\Delta P_{ind}(t) - P_{val}]\left(\frac{1}{R_1} + \frac{1}{R_2 + R_3}\right)$$

Because this equation starts at $t_1$ with initial conditions (i) $S(t_1) = S_1$, and (ii) $\Delta P_{ind}(t_1) = P_{val}$, the rigorous solution satisfying these conditions at all times $t_1 < t < T_c$ may be finally expressed as:

$$S(t) = S_1\left\{1 + \frac{\tau_{act}}{\tau_{oc}}\left(\frac{P_0}{P_{val}} - 1\right)\left[1 - \exp\left\{-\frac{t - t_1}{\tau_{act}}\right\}\right]\right\} \quad \text{(Eq. 36)}$$

The behavior of the second branch, namely the solution (36), is represented by diagram (c) in FIG. 24 starting at $t_1$. One can note that the open valve 32 provides the exponential kinetics (c) of the second branch with the characteristic time constant $\tau_{act} \neq \tau_{oc}$, which makes the diagram (c) very different from the diagram (b) representing the case where $\tau_{act} = \tau_{oc}$. The sharp transition of the solution from the branch (b) to branch (c), having a different slope, allows the easy and very precise determination of both the exact moment $t_1$ and the specific signal $S_1$ corresponding to that $t_1$. One way to do this is if the processor extrapolates both the acquired branch (b)

above $t_1$ as shown with dash-dotted line in FIG. 23 and the acquired branch (c) below $t_1$, and looks for the time-point where both extrapolations merge. Another way is to look for the time $t_1$ and to calculate the derivative of the entire sequence of all signals $S(t)$ acquired after the moment $t=0$. The diagram (d) in FIG. 24 shows that the change in slope at the moment $t_1$ results in the sharp drop of the derivative $dS(t)/dt$. If the number of acquired discrete signals is high enough, any method of these two can give precise values for both $t_1$ and $S_1$. It follows from the above that the while at least about 2.5 $t_1$ is enough time to acquire a desirable number of signals and calculate both $t_1$ and $S_1$ when the frequency $f_0$ is chosen so high that 2.5 $t_1$ $f_0 \geq 5$, and more desirably 2.5 $t_1$ $f_0 \gg 5$. At the same time it can be appreciated that the calculation time 2.5 $t_1$ $f_0$ cannot exceed the shortest time $T_c$ which can be desirable in accordance with the lowest predetermined dose $D_0$.

The value of two calculated values $t_1$ and $S_1$ is that they reflect the specificity of each cycle and can desirably be directly used for further calculation of the time period $T_c$, which determines the moment $t_{end}$ for termination of this cycle. Thus, both parameters $t_1$ and $S_1$ may desirably be calculated in the beginning of each cycle and stored in processor's memory. After this is done, the next actions performed by the processor are: the analysis of the branch (b) in order to determine time-constant $\tau_{oc}$, and then the analysis of the branch (c) determining time-constant $\tau_{act}$ related to the current cycle. Because both branches represent exponential functions, the processor can perform this analysis with the use of standard mathematical methods. Then the processor extrapolates the recorded part of the branch (c) to higher times and calculates the maximum signal $S_{max}$ that could be reached if the cycle continues for an indefinitely long time. Quantitatively determined $S_{max}$ is further substituted into the left part of the expression (36) wherein the exponent in the right part is set to zero. After that one can do simple mathematical transformations leading to the following form of time-dependent effective pressure change $\Delta P_{eff}(t)$ where the calibrating factor (34) previously determined is also taken into account:

$$\Delta P_{eff}(t) = \alpha\beta(S(t) - S_1) \quad \text{(Eq. 37)}$$

$$= P_{val}\left(\frac{S_{max}}{S_1} - 1\right)\left[1 - \exp\left\{-\frac{t-t_1}{\tau_{act}}\right\}\right]$$

The initial expression (33) describing the output fluid flow $F_2(t)$ of some embodiments in very general form, becomes fully determined by the expressions (24) and (37) as a function of the running time wherein two device's constants $\alpha_{ini}$ and $P_{val}$ are known to the processor in advance, and other parameters that can vary from one cycle to another one, namely $t_1$, $S_1$, $S_{max}$, $\tau_{act}$, and $\tau_{oc}$, are determined in the process of each particular cycle. In the time interval $t_1 < t < T_c$ this function can be expressed as follows:

$$F_2(t) = \frac{P_{val}}{\alpha_{ini}}\left(\frac{1}{\tau_{act}} - \frac{1}{\tau_{oc}}\right)\left(\frac{S_{max}}{S_1} - 1\right)\left[1 - \exp\left\{-\frac{t_1-t}{\tau_{act}}\right\}\right] \quad \text{(Eq. 38)}$$

One can note that all parameters of the formula (38) are either calibrated values or values determined in the process of current cycle. It should be appreciated that quantitative measurement of current value $\tau_{oc}$ corresponds to determining of the resistance $R_1$ according to expression (25), and any accidental change of this resistance (including its dependence on the temperature) can be recorded by the processor. At the same time potential change of output resistance $R_{exit}$ reflected by the expression (5) can be easily found from the analysis according to the expression (24). Taking into account the calibration (34) discussed before one can see that the modified method of these embodiments can provide self-calibration of the whole device of the fluid delivery, and this complete calibration may be performed by the processor in the process of each cycle. It can be appreciated that such self-calibration can be automatic.

It can be appreciated that integration of the formula (38) over time period $t_1 < t < T_c$ determines only part of the fluid dose delivered to the exit opening. At the time $T_c$ the pressure in the compression section 8 of the reservoir drops sharply but the fluid flow $F_2(t)$ decays relatively slow with the same time-constant $\tau_{act}$. The diagram (e) in FIG. 24 representing $F_2(t)$ shows that this exponential decay can continue only for the limited while $T_c < t < t_2$ because the decreasing pressure in the indicator 9 again crosses value $\Delta P_{ind}(t_2) = P_{val}$ at the moment $t_2$ (see also the diagram (c) in FIG. 24), and the valve 32 returns to the closed state. Therefore the last stage of the fluid flow $F_2(t)$ related to final interval $T_c < t < t_2$ is expressed as follows:

$$F_2(t) = \quad \text{(Eq. 39)}$$

$$\frac{P_{val}}{\alpha_{ini}}\left(\frac{1}{\tau_{act}} - \frac{1}{\tau_{oc}}\right)\left(\frac{S_{max}}{S_1} - 1\right)\left[1 - \exp\left\{-\frac{t_1-T_c}{\tau_{act}}\right\}\right]\exp\left\{\frac{T_c-t}{\tau_{act}}\right\}$$

where the final point $t_2$ of outgoing flow $F_2(t)$ satisfies the following expression:

$$\exp\left\{\frac{T_c-t_2}{\tau_{act}}\right\} = \frac{S_1}{S_{max}} \quad \text{(Eq. 40)}$$

It follows from the above that according to a general approach of the integral expression (9) the predetermined dose $D_0$ must be equal the actual dose which is formed by the such sum of two integrals. The initial part of the actual dose corresponds to the flow $F_2(t)$ expressed as (38) which is integrated in the first time interval $t_1 < t < T_c$. The final part of the actual dose corresponds to the flow $F_2(t)$ expressed as (39) which is integrated in the second time interval $T_c < t < t_2$. The sum of these two integrals representing the actual dose can be calculated. It becomes equal to $D_0$ if the expected moment $T_c$ is chosen in accordance with following transcendental equation:

$$T_c + \frac{\tau_{act} S_1}{S_{max}}\exp\left\{\frac{t_1-T_c}{\tau_{act}}\right\} = \quad \text{(Eq. 41)}$$

$$t_1 + \frac{\tau_{act} S_1}{S_{max}} + \frac{\alpha_{ini}\tau_{act} D_0}{P_{val}\left(1 - \frac{\tau_{act}}{\tau_{oc}}\right)\left(\frac{S_{max}}{S_1} - 1\right)}$$

Complicated analytical form of this equation does not create any problem because the algorithm of a digital processor can use standard numeric methods in order to determine $T_c$ corresponding to the solution of this transcendental equation (41). Due to the time 2.5 $t_1 f_0$ required to complete the prediction is shorter than $T_c$, in the beginning of the last step of the modified method the processor is waiting for such real time moment $t_{end} = T_c + t_{st}$ which is appropriate to send the terminating signal to the system 14 so that the drop of the pressure in the compression section of the reservoir occurs exactly at the predicted moment $T_c$.

It should be appreciated that the final equation (41) has been developed by the inventor only as an example to demonstrate how mathematical algorithms of the invention can be developed. This particular example considers only simple exponential kinetics of the processes occurring in the expandable indicator section 9 when a quasi-rectangular pressure pulse is performed in the compression section. The algorithm developed on this basis is rather good for cases of devices wherein a low transition time $T_{up}$ can be neglected in comparison with $T_c$, and then relatively a stable pressure plateau $P_0$ is produced in the compression section 8 of the reservoir. However, it should be appreciated that the teaching of the present invention, based on represented by the expression (9) a general method of the integration of outgoing fluid flow, includes also all other cases where the smooth pressure plateau $P_0$ may have a certain slope during the time $T_c$, similar to that one shown in the top view of FIG. 18. It follows from the mathematical scheme disclosed above that only certain math corrections of the equation (41) may be further required if the slope of $P_0$ causes additional terms in parental equation (31). There is no doubt that such corrections can be easily done with the use of very similar approach in the framework of the same scope of the invention even if the pressure pulse in the compression section is not exactly quasi-rectangular one.

The initial steps of certain algorithmic corrections are demonstrated below. For example, it may be possible that in some embodiments the system 14 is sufficiently simple that it produces a relatively long transition time $T_{up}$ that cannot be neglected under given technical requirements. In this case the basic differential equation (20) related to more advanced devices can be corrected so that instead of immediately getting the constant $P_0$, the equation contains the expression describing the actual smooth kinetics of the transition from zero excessive pressure to the pressure plateau $P_0$, as shown for example in differential equation (42):

$$\frac{d}{\alpha dt}\Delta P_{ind} = \frac{P_0(1 - \exp\{-2t/T_{up}\})}{R_1} - \Delta P_{ind}\left(\frac{1}{R_1} + \frac{1}{R_2 + R_3}\right) \quad \text{(Eq. 42)}$$

In accordance with the first term in the right side of the equation (42) the pressure in the compression section reaches $P_0$ for finite time about $2T_{up}$ and cannot be neglected. In this case the modified differential equation (42) is valid for whole period $0 < t < T_c$, and its rigorous solution differs a little bit from simple solution (21) as follows:

$$\Delta P_{ind}(t) = \frac{P_0}{(1 + R_1/R_{exit})} * * \left[1 + \frac{\alpha T_{up}(1 + R_1/R_{exit})\exp\{-2t/T_{up}\} - 2R_1\exp\{-t/\tau_{act}\}}{2R_1 - \alpha T_{up}(1 + R_1/R_{exit})}\right] \quad \text{(Eq. 43)}$$

Because the kinetic solution (43) is already found, the further development of the improved algorithm corresponding to the kinetics (43) can follow a similar approach. At negligibly low $T_{up}$ the complicated expression (43) coincides with more simple solution (21). Taking into account that real $T_{up}$ is never equal zero, this means that the improved algorithm can result in higher precision than those previously disclosed above. So, more precise solution (43) provides an example of how a mathematical correction can be done if one needs to obtain more precise algorithm controlling the device. Simultaneously it shows that in this case the entire analysis becomes more complex. Correspondingly the using of more precise algorithms may require more complicated programming of the processor and can be recommended only if increased precision is a real necessity.

It may be obvious to anyone skilled in the art that in the case of very simple compressing system 14 even low residual pressure remaining in the reservoir after the end of the current cycle is not desirable because this can influence the precision of the next cycle of the fluid delivery. That is why the method of certain embodiments may comprise one more additional step aiming to remove the residual pressure completely before the beginning of the next cycle. Two different approaches can be taken so that both comprise the acquiring of at least one, and most desirable more than one, signals S(t) after the end of previous cycle (shown with black circles on the diagram (c) in FIG. 24). In the case of the first approach the processor detects the presence of the low residual pressure and sends additional signals to the system 14 at the moment $t_3$. These additional signals cause fine adjustment of the force applied to the fluid until the pressure inside the reservoir becomes equal external pressure $P_{ext}$. Corresponding change of the pressure is shown by dotted parts of both diagrams (a) and (c) in FIG. 24. The second approach is to supply the compression section 8 of the reservoir with an optional electrically controlled valve 85 shown in FIG. 22 schematically as dotted rectangle. When valve 85 is opened it connects the cavity of the compression section 8 with external atmosphere. However, the valve 85 is closed practically all the time and does not participate at all in the fluid delivery cycle. If after the end of the cycle the processor detects the presence of the low residual pressure the optional signal 86 opens the valve 85 shortly (let say, for few seconds) until the pressure inside whole reservoir becomes precisely equal to $P_{ext}$ and the device is fully ready to begin the next cycle. The choice between two approaches depends only on which approach of two is cheaper and simpler from viewpoint of the engineering and/or fabrication.

At this point it may be relevant to point out some advantages of the modified method applicable to most advanced devices of the invention. One can see that the right side of the final equation (41) contains predetermined dose $D_0$, two calibrated factory pre-set constants $P_{val}$ and $\alpha_{ini}$ known to the processor in advance, and also only a few variable parameters need be directly determined in the beginning of each cycle. It has been demonstrated that said determinations, carried out by processor's algorithm treating signals of the sensor system, provide self-calibration of the entire device before determining the end moment $t_{end}$ corresponding to each predicted $T_c$. That is why all variable parameters of the equation (41) reflect potential changes of either external or internal conditions, including (i) the variations of external pressure $P_{ext}$ and internal excessive pressure $P_0$; (ii) potentially possible, unpredictable changes of resistances $R_1$, $R_2$, and $R_3$ which may be sensitive to the temperature, external or internal occlusions whether partial or insurmountable ones, and/or accidental mechanical damages; and also (iii) the variations of the parameter $(\alpha\beta)$ calibrating the sensitivity which may be different for each particular cartridge and can depend on the particular position of the cartridge inside the device, voltage of batteries supplying electric power, mechanical shocks, and so on. Thus, the right side of the equation (41) is fully determined so that each prediction of $T_c$ takes into account everything what may happen to the device.

Figure 25:
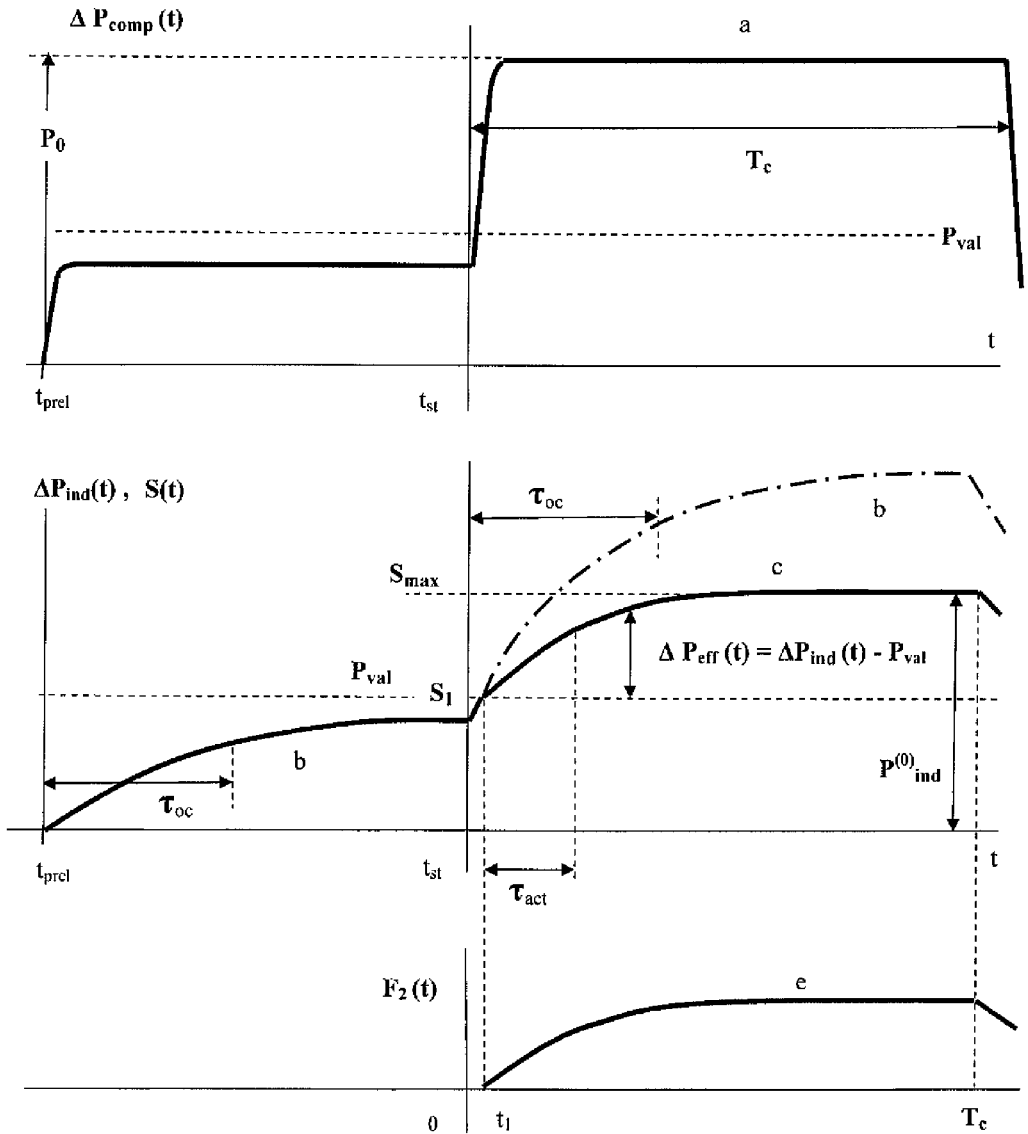
FIG. 25 depicts diagrams related to further improvement of the method applicable to most advanced embodiments of the invention.

The most advanced method disclosed above provides most impressive set of advantages of the invention. However, relatively short period of the first kinetic branch $0<t<t_1$ (see FIG. 24) may lead to not the best precision of determination of such important parameter as $\tau_{oc}$. That is why it may be desirable to improve most advance method slightly in order to obtain highest possible precision of determination of $\tau_{oc}$. The diagram of such improvement shown in FIG. 25 expresses its idea that exact determination of $\tau_{oc}$ can be done just before the beginning of main part of delivery cycle. In order to do so it is desirable that at certain predetermined preliminary moment $t_{prel}<t_{st}$ preceding the beginning of the cycle the processor produces at least one preliminary electric signal which makes driving force system to cause relatively low level non-zero squeezing out force (FIG. 25, a). Important condition is that during relatively long period between $t_{prel}$ and $t_{st}$, which may be comparable with $\tau_{oc}$ or even exceed it few times, expandable element of the indicator is subjected to the pressure $P_{ext}<P_{ind}(t)<P_{val}+P_{ext}$ so that valve 85 is closed and no fluid can leave through the exit opening. In fact, the whole period between $t_{prel}$ and $t_{st}$ represents the state of artificial occlusion shown with solid line (b) in FIG. 25. Correspondingly, at this period the processor can get at least two signals provided by the sensor system, and more preferable as many signals as necessary to determine $\tau_{oc}$ with desirable high precision. After this high precision determination is complete the processor produces main starting signal at the moment $t_{st}$ so that the main part of the cycle begins exactly as it has been described in preceding paragraphs of present section H and shown in right side of FIG. 25 (curves a, c, and e). At that part of the cycle the pressure in the reservoir exceeds $P_{val}$ (curve a) and the fluid is delivered through the exit opening (curve e). Finally, the only practical difference and advantage of improved method is that in the calibration process both said actual hydraulic resistances $R_1$ and $R_{exit}$ are determined with significantly improved precision.

The methods and compact devices of the invention may be used for the delivery of any soluble drugs in as low doses as about 0.02 mm³ of the solution or better, with high resolution about 0.001 mm³ or better by the order of magnitude. However, there is no practical upper limit if desirable dose exceeds 0.02 mm³. This statement can be confirmed by the following quantitative example related to the delivering of the insulin in order to treat the diabetes.

Consider that the average speed of delivery of insulin treatment is prescribed to be 12 mm³/hour if there is no medical emergency. The replaceable cartridge can comprise the resistor 5 having the length 10 mm and the diameter 0.052 mm which correspond to the hydraulic resistance about $R_1=500$ Kgram·s/cm⁵ for the insulin dissolved in a water. At the same time the hydraulic resistor 31 is chosen to have the length 10 mm and the diameter 0.07 mm providing the hydraulic resistance $R_2=165$ Kgram·s/cm⁵ so that the ratio $R_1/R_{exit}=R_1/R_2=3$ corresponds to normal conditions with no occlusion. The stiffness factor of the indicator 9 having internal diameter 2 mm and the length 3 mm (see FIG. 7 for example) is about $\alpha=50$ Kgram/cm⁵, whereas the driving force system is designed so that the average $P_o$ is about 0.2 Kgram/cm² in the compression section 8, which corresponds to average $\Delta P_{ind}$ about 0.05 Kgram/cm² if there is no external occlusion and $R_3=0$. It is assumed that the valve 32 is switched at the calibrated pressure drop $P_{val}=0.015$ Kgram/cm². At zero pressure difference in the indicator 9 the gap 44 of the capacitor sensor (see FIG. 8) or optical sensor (see FIG. 13) can be chosen relatively high about 0.12 mm. The desirable frequency of signal acquisition can be chosen $f_o=30$ Hz, and the precision of signal's digitization can be at least 0.1% of full range.

It is easy to use the expressions (21-41) and to see that under the normal conditions assumed in the previous paragraph, the state of the device is: $\tau_{oc}=10$ s, $\tau_{act}=2.5$ s, $t_1=0.75$ s, the change of the gap 44 about 0.045 mm (30% of full range) corresponds to the indicator's volume expansion $\Delta V$ about 1 mm³ (11% of $V_0=9$ mm³), the minimum $T_c=1.15$ s, the outgoing flow $F_2(t)$ reaches its maximum rate about 0.21 mm³/s if $T_c$ is about 5 s or longer. For initial 1.15 s of the cycle the processor acquires 35 signals which provide 22 points to measure $\tau_{oc}$ and 13 points to measure $\tau_{act}$. The amount of the insulin delivered to the exit opening for this 1.15 s initial period is equal only 0.017 mm³ which may be considered as the minimum dose inherent for this particular device. With the frequency $f_0=30$ Hz the precision of the device in the time is about 0.03 s, and corresponding precision of the dosage is close to 0.001 mm³. Taking into account the preprogrammed average speed of the insulin delivery 12 mm³/hour, it may be reasonable to choose the dose of one cycle $D_0=1$ mm³ which requires $T_c=6.16$ s in accordance with the equation (41) at normal conditions. The desirable average speed of the delivery is fulfilled if the device's program performs 12 cycles/hour or one cycle per 300 s. In the case of medical emergency the device having such parameters is capable of increasing the repetition rate up to 1 cycle per 10 s, thus increasing the average speed of the delivery about 30 times from the standard 12 mm³/hour to about 360 mm³/hour. This example is based on realistic numbers and demonstrates that the performance of devices of the invention can exceed that of prior art systems for insulin delivery by more than one order of magnitude in regard of the minimum dose, and more than two orders of magnitude in regard of the precision. The reliability and smart behavior of the invented devices is also demonstrated below in realistic numbers.

For example, in the driving force system the pressure plateau $P_0$ achieved in different cycles can fluctuate by ±50% between 0.3 Kgram/cm² and 0.1 Kgram/cm². This results in a corresponding fluctuation of $S_{max}/S_1$ between 5 and 1.67, and in entire accordance with the solution of the equation (41) the processor keeps constant preprogrammed dose 1 mm³ of each cycle by corresponding changes of the predicted $T_c$ between about 4.03 s and 18.82 s. The other case is if at normal pressure $P_0$ a partial occlusion occurs so that $R_3=19\ R_2$. Then the processor detects the increase of $\tau_{act}$ from initial 2.5 s up to 8.69 s, followed by the pressure increase in the indicator section up to 0.176 Kgram/cm² instead of normal 0.05 Kgram/cm². It corresponds to a new ratios $S_{max}/S_1=11.7$ and $\tau_{act}/\tau_{oc}=0.87$. The processor uses new numbers to resolve the equation (41) and compensate this strong occlusion completely by changing $T_c$ from 6.16 s to 21.8 s so that this increase prevents any change of predetermined dose $D_0=1$ mm³.

It should be appreciated that the quantitative examples considered above are provided for better illustration of the invention only, and should not create any limitation in the design of other devices of the same invention having rather different quantitative parameters and abilities.

Other advantages of embodiments of this invention include non-interrupted self-monitoring of internal parameters and using the processor's memory to store the history of changes detected. Analysis of that history, including periods between the cycles, can provide reliable self-diagnosis of the internal state of the device. For example, detection of a sharp drop of the measurable parameter $S_{max}$ below a predetermined level, repeated over a few cycles, may be evidence of incorrect operation or even a defect in the driving force system. Likewise, a relatively gradual decrease of the $S_{max}$ observed over several cycles may indicate that the reservoir is practically empty and the user should be advised to change the replaceable cartridge. Similarly, the history of the measurable parameter $\tau_{oc}$ which reflects the ratio $R_1/\alpha$ can be useful. The stiffness factor $\alpha$ is a mechanic characteristic and its potential change can be very gradual, because of slow aging of the elastic material. The use of fully disposable cartridges having short life-time reduces the likelihood that $\alpha$ would change significantly over time. In the case of non-replaceable cartridges designed for the long-term usage, the change of $\alpha$ influences both $\tau_{oc}$ and $\tau_{act}$, but does not change their ratio (see the expression (24)). That is why a rapid increase of $\tau_{oc}$ determined by the algorithm with a simultaneous change of the ratio $\tau_{oc}/\tau_{act}$ may only mean either the mechanical damage or accidental occlusion of the internal hydraulic resistor $R_1$, which can especially happen if an inexperienced user introduces mechanical contaminants while refilling of the non-replaceable cartridge. The opposite case can occur if $\tau_{oc}$ remains constant and only the rapid change of $\tau_{act}$ is detected. This could be a sign of either mechanical damage of the hydraulic resistor $R_2$ or the occlusion in the exit opening of the flow passage.

When a change of a parameter is detected, an additional program of the processor first analyzes potential consequences of this change. If the predetermined dosage can be preserved by making a corresponding adjustment of the device's regime during the next cycle, there is no need to disturb the user. Conversely, if a malfunction is detected that cannot be self-compensated by the algorithm controlling the delivery cycles, the processor can inform the user promptly regarding what has happened to the device and what actions are advised to improve the situation. For example, the user can be advised to change a replaceable cartridge or to refill a non-replaceable one if the program detects too little fluid remaining in the reservoir. It may be desirable that ether visual or acoustic alarm signal is produced to attract the user's attention, and report the situation and provide instructions via an LCD screen of the control panel.

Simple design and very low technical requirements related to the driving force system considered above in section D allow obtaining of uniquely high reliability of whole device even in certain very rare emergency cases when processor detects critically strong malfunctioning of automatically controlled driving force system which is represented by means capable of changing the force squeezing the fluid out of the reservoir over time. Such malfunctioning may happen suddenly, for example, if the driving force system is accidentally damaged by any reason or by a patient (especially if he or she is an inaccurate child) or, for another example, if during patient's long-term flight the battery becomes so low that the motor 76 of driving force system cannot work properly whereas there is no possibility to recharge the battery till the end of a flight. However, the device of the invention may keep quite reasonable level of its functionality for indefinitely long time with minimum participation of the patient thus saving his or her life even in such rare critical events. In that regard it is relevant to remind that the device of the invention can keep its high precision even if increased pressure in the reservoir is rather unstable in time (see FIG. 18 for example) or if amplitude of the pressure varies in rather wide brackets $P_{max}/P_{min}$ up to 25. It may be appreciated by anyone skilled in the art that in the case of emergency so soft requirements may be easily satisfied if increased pressure in the reservoir is created by the patient manually. That is why it may be desirable that the device of the invention is also supplied with additional emergency means providing a patient with an ability of manual application of the pressure to the fluid in the reservoir in order to cause such changing of squeezing out force over time which is similar to the change while normal work of driving force system. Obviously, in order to provide acceptable precision of drug delivery the patient must act under supervision of the processor. It should be appreciated by anyone skilled in the art that in such emergency cases the processor receiving signals of the sensor system can automatically detect the moment $t_{st}$ when the patient manually initiates squeezing out force. After that the processor should use most appropriate algorithm among of few ones described above and define necessary duration of the cycle $T_c$ accordingly to actual pressure created by the patient manually. That is why the only real necessity is that the processor should be capable of initiating at least one either acoustic or visual signal at the moment $t_{end}$ corresponding to calculated $T_c$, said signal providing the patient with strict order to terminate the squeezing out force as soon as possible. For example, the device may display such ending signal at the moment $t_{end}$ on LCD screen, or use flashing lamp, or use any other suitable information means. However, for better precision of manual dosing it is more desirable that the processor is also capable of initiating a preceding signal at the moment $t_{st}$ (it may be also called "first emergency signal") destined to prompt the patient to start immediate manual application of squeezing out force in accordance with programmatically predetermined moment. Correspondingly, the ending signal produced at the moment $t_{end}$ and destined to prompt the patient to terminate said manual application of the squeezing out force may be also called "second emergency signal". Cyclic manual operation based on the use of these two signals should be repeated until substantial technical help can be provided to the patient in order to restore normal automatic work of the device. Thus, even partially broken device of the invention may be used temporarily in order to overcome certain very serious dangers irresolvable by any known drug delivery devices.

Figure 26:
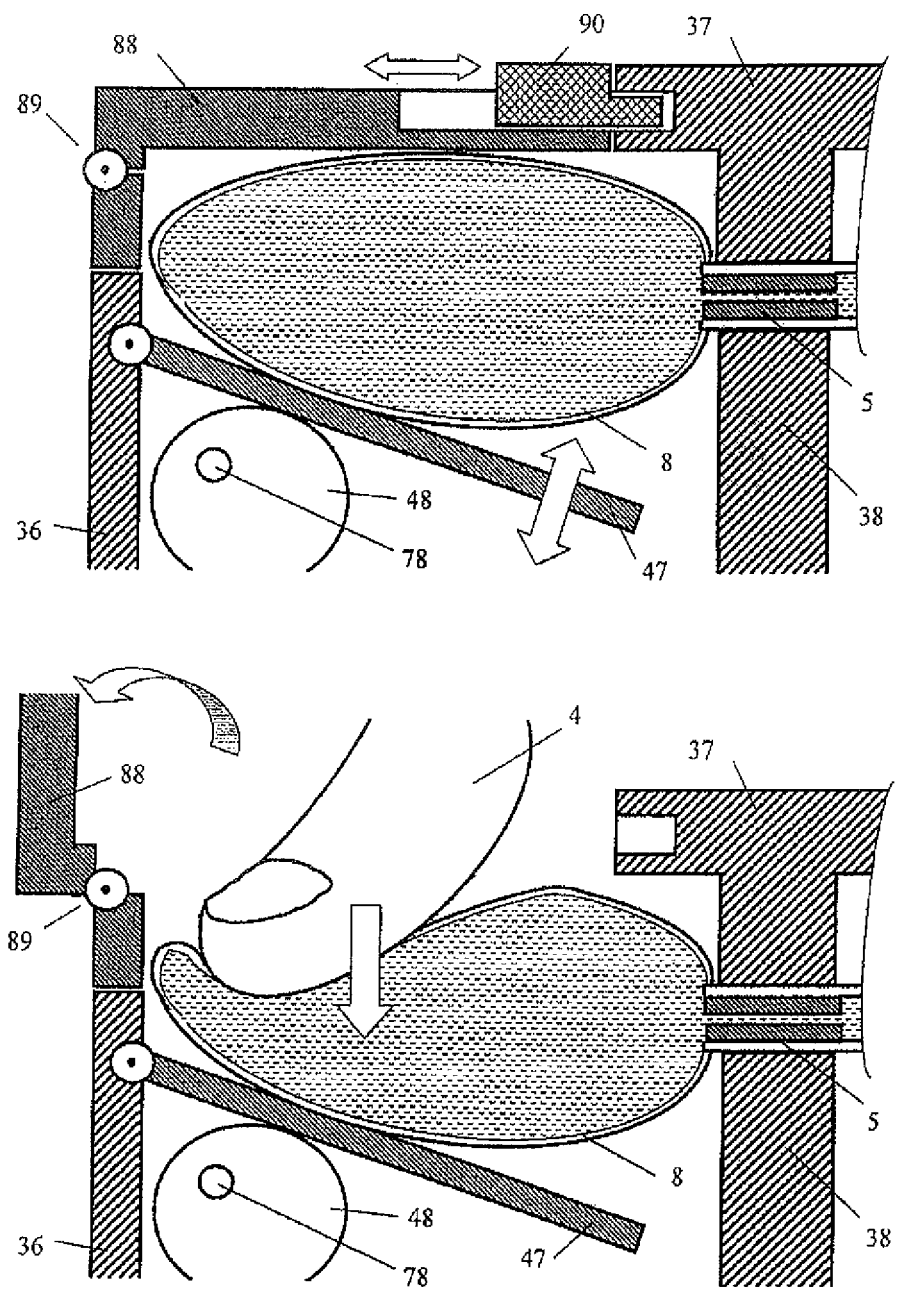
FIG. 26 depicts both an example of electromechanical means for automatic application of squeezing out force to an elastic reservoir filled with a fluid and locked in a cavity of device's housing (top view), and an example of another means of the same device (bottom view) allowing manual application of squeezing out force in rare emergency situation if automatic driving force system fails due to low battery or any other technical reason.

Simple example of additional means providing a patient with an ability of proper manual changing of squeezing out force over time in certain emergency cases is shown in FIG. 26 and FIG. 6. Technical design of this particular example assumes that the driving force system of the device corresponds to the scheme shown in FIG. 22. It has been already stated that before the beginning of normal work of the device the compression section 8 of replaceable cartridge must be placed into the cavity of the housing 36 so that after closing of the lid 37 (see FIG. 6) this section 8 becomes locked between internal surface of the lid 37 and compressing plate 47. Top view of FIG. 26 shows cross section of that part of the housing 36 where the section 8 and the plate 47 are located while normal work. Bottom view of FIG. 6 shows that in certain part of the lid 37 there is a window which is normally closed by small sub-lid 88 connected with main part of the lid 37 by an axis 89 and locked by a latch 90 shifted in right direction (see top view of FIG. 26). While normal work the compression and decompression of the section 8 is provided by rotation of the wheel 48 and corresponding movement of the plate 47 depicted in the top of FIG. 26 by thick white arrow. However, in given example the window in the lid 37, sub-lid 88, and the latch 90 constitute said additional means providing the patient with said ability of manual operation in certain emergency cases.

The processor analyzing signals of sensor system can define when normal work of the device becomes broken because of malfunctioning of the driving force system. Obviously, the plate 47 cannot move in this case and no pressure change may occur in the reservoir. In this case the processor initiates specific alarm signal, and also it may use LCD screen to provide necessary instructions to the patient. Accordingly to these instructions the patient must unlock the sub-lid 88 by shifting the latch 90 in left direction, and then elevate the sub-lid 88 as shown by rounded arrow in bottom view of FIG. 26 in order to open the window in the lid 37. Then the patient must apply his or her finger 4 to the elastic bag 8 and press it modestly in order to initiate increased pressure in the reservoir as shown by vertical arrow in bottom view of FIG. 26. It is desirable that the beginning of the pressure increase occurs after the preceding signal initiated by the processor. However, in certain embodiments the patient can start manual pressing even without preceding signal because such start must be automatically detected by the sensor system and recorded by the processor. Typically the finger of any usual size should create rather moderate force between about 0.1 Kgram and about 1 Kgram in order to cause correct squeezing out force within allowed brackets $P_{max}/P_{min}$. So low force can be easily applied by any adult person or even a child, and no high stability of manual pressure is required. In order to get right dosing of the drug the patient should just hold his or her finger pressing until ending signal is received which should be initiated by the processor at calculated moment $T_c$. After that the patient removes the finger 4 as soon as possible, and then closes and locks sub-lid 88. The processor will inform the patient to repeat the same simple sequence of operations when next dosing cycle will be required. It should be appreciated by anyone skilled in the art that specific constructive design of additional emergency means described above is provided as an example only, and many other constructive designs of similar additional means (including, for example, different systems of levers and/or buttons excluding direct contact of the finger 4 with the section 8) are possible in order to provide the patient with an ability of manual changing of squeezing out force over time accordingly to the teaching of the invention.

It may be appreciated that a wide dynamic range of programmatically determined doses combined with high precision of liquid drug dosing, create one more advantage over prior art devices. It is well known that medical condition of an outpatient may depend on multiple factors, including personal physiological peculiarities, environmental factors, quantity and quality of food, and so on. These factors can change a personal medical condition unpredictably at different times and different places. In such cases embodiments of this invention can provide this person one or more specific bio-medical devices or sensors capable of prompt analysis of important physiological parameters to find adjusted dosing to meet the needs of the patient at a particular moment in time. For example, a sensor can analyze the concentration of a specific molecule in patient's blood, or electric activity of the brain, or something else what is reasonable in each particular case. The state of the patient can be improved if signals produced by such a bio-medical device or sensor are periodically transmitted to the control system to make prompt corrections of doses of the liquid drug delivered. That is why it may be appreciated that in order to improve a quality of medical treatment, the improved methods and devices of the invention comprise transmitting signals of at least one bio-medical device capable of detecting a physiological feature of a patient to the control system of the device, and the method further comprises correcting the dose delivered accordingly to the transmitted signal from the bio-medical device.

The description of embodiments above demonstrates that the devices and methods of the invention are simple in their engineering design, inexpensive in mass fabrication, highly reliable in all respects, and posses the ability of "smart" behavior in practical use in unpredictably changing environments of the real life. It can be appreciated that the above descriptions and embodiments are illustrative of the invention, and numerous modifications of similar devices and methods may be developed and remain within the scope of the invention. All references cited herein are incorporated fully by reference.

I claim:

1. A fluid delivery device, comprising:
   a reservoir comprising:
   a first component containing a first portion of said fluid, said component operably linked to a device designed to provide a time-dependent squeezing out force;
   a second component containing a second portion of said fluid, comprising at least one expandable element made of a resilient material, said second component further operably linked to a sensor system capable of producing at least one output signal associated with at least one geometric parameter of said expandable element, and an outflow passage having a non-zero hydraulic resistance $R_2$;
   a hydraulic resistor connecting said first and second components;
   said hydraulic resistor providing predetermined non-zero hydraulic resistance $R_1$; and
   a programmable processor capable of:
   (i) acquiring output signals of said sensor system; and
   (ii) providing an output signal to said device capable of changing over time a force squeezing the fluid out of the first component of said reservoir.

2. The device of claim 1, said outflow passage further comprising:
   a pressure-dependent static hydraulic resistor capable of switching its resistance $R_{val}$, so that said resistance $R_2$ exceeds $R_{val}$, and more preferably $R_2$ exceeds $R_{val}$ at least one order of magnitude when a pressure drop applied to said pressure-dependent resistor is more than predetermined value $P_{val}$, whereas the resistance $R_{val}$, exceeds $R_2$, more desirably $R_{val}$ exceeds $R_2$ by at least one order of magnitude, and most desirable $R_{val}$, exceeds $R_2$ by more than two orders of magnitude when said pressure drop is less than said $P_{val}$.

3. The device of claim 1, said device designed to provide a time-dependent squeezing out force provides direct interaction of said force with a first limited surface area of said fluid in the first component of the reservoir, said first limited surface area of the fluid being spatially separated from a second limited surface area of the fluid brought into contact with at least part of said expandable element of the second component of the reservoir.

4. The device of claim 1, where a ratio $R_1/R_2$ exceeds about 0.05 and is less than about 200, more desirably said ratio is between about 0.25 and about 40, and most desirably said ratio is between about 1 and about 10.

5. The device of claim 1, said sensor system comprising a piezoelectric sensor producing an analog signal, said sensor being either directly or indirectly connected to an external surface of said second component of said reservoir.

6. The device of claim 1, said sensor system comprising a capacitor sensor.

7. The device of claim 1, said sensor system comprising a non-contact magnetic sensor.

8. The device of claim 1, said sensor system comprising a non-contact optical sensor.

9. The device of claim 1, said device capable of changing over time said force squeezing the fluid out of said first component of said reservoir comprising:
  a piston of a syringe; and
  an electromechanical system capable of moving said piston in any of two opposite directions according to said output signal produced by said processor.

10. The device of claim 1, said device capable of changing over time said force squeezing the fluid out of said first component of said reservoir time comprising:
  a peristaltic mechanism.

11. The device of claim 1, said device capable of changing over time said force squeezing the fluid out of said first component of reservoir comprising:
  an expandable bag containing a gas; and
  electric means capable of changing a temperature of said gas in response to a output signal produced by said processor, said bag located either inside said first component of said reservoir or in close proximity to at least a portion of said first component of said reservoir.

12. The device of claim 1, wherein the device further comprises an additional means providing a patient with an ability of manual changing of said squeezing out force over time in certain emergency cases of critically strong malfunctioning of said means capable of changing said squeezing out force over time accordingly to controlling signals of said processor, whereas in the case of said emergency said processor is further capable of initiating at least one either visual or acoustic signal providing the patient with an order to terminate said squeezing out force created by the patient manually.

13. A method for a delivery of a predetermined dose of a fluid, comprising following steps:
  (a) providing a device of claim 1;
  (b) initiating a non-zero force squeezing the fluid out of the reservoir;
  (c) acquiring at least one signal associated with at least one geometric parameter of said expandable element;
  (d) calculating a time $t_{end}$, comprising treating said acquired signal by a processor capable of executing commands based upon a predetermined mathematical algorithm; and
  (e) terminating said force at $t_{end}$.

14. The method of claim 13, wherein the method further comprises:
  (i) before the step (b) subjecting the fluid in the reservoir to a low pressure sufficient to prevent the fluid from flowing out of said exit opening, said low pressure in the reservoir close to an external pressure $P_{ext}$;
  (ii) the step (b) further comprising producing at least one starting electric signal at a predetermined moment $t_{st}$, said starting signal resulting in producing:
    said squeezing-out force; and
    subjecting said expandable element to a pressure $P_{ind}(t)$ within predetermined brackets $P_{max}+P_{ext} > P_{ind}(t) > P_{min}+P_{ext}$, wherein $25 > P_{max}/P_{min} > 1$;
  (iii) treating said acquired signal comprising determining a pressure difference $P_{ind}(t)-P_{ext}$ and further comprising determining a period $T_c$, satisfying the condition $T_c = t_{end} - t_{st}$, wherein $T_c$ is of such duration of said squeezing-out force to provide an equality of said predetermined dose and an actual dose delivered, said actual dose being a ratio having a numerator being an integral found by integrating of said pressure difference over time since the moment $t_{st}$, and a denominator is a parameter expressing hydraulic resistance $R_{exit}$ of said means connecting the reservoir with said exit opening;
  (iv) the step (e) comprises producing at least one ending electric signal at $t_{end} = T_c + t_{st}$, said ending signal results in decreasing the force so that the pressure of the fluid in the reservoir can relax up to about its initial value before step (b).

15. The method of claim 14, wherein said predetermined $R_2$ is substituted into said denominator in order to fulfill the role of said parameter expressing said $R_{exit}$, and said integral is proportional to a sum of all said signals acquired since the time $t_{st}$.

16. The method of claim 14, wherein hydraulic communication between two spatially separated sections of the reservoir has a resistance $R_1 \geq 0.05 R_2$; the step (c) comprises acquiring at least two signals; said treating while step (d) comprises:
  determining an actual hydraulic resistance $R_{exit}$ of said the hydraulic resistor connecting the reservoir with said exit opening;
  making said denominator equal said actual $R_{exit}$;
  substituting said actual $R_{exit}$ into an analytic expression of said integral constituting said numerator; and
  producing an alarm signal if said actual $R_{exit}$ exceeds a predetermined level.

17. The method of claim 16, wherein said hydraulic resistor connecting the reservoir with said exit opening is further supplied with an element switching hydraulic resistance at a predetermined pressure drop $P_{val}$;
  step (c) comprising acquiring at least five and most desirably significantly more than five signals;
  said treating while step (d) further comprising:
    calibrating said system delivering the fluid;
    checking current performance of major components of this system;
    checking an amount of the fluid remaining in the reservoir; and further comprising:
  producing one or more of a report and an alarm signal to inform a user if said amount of remaining fluid is below a predetermined amount or a malfunction is detected that cannot be self-compensated by said algorithm determining of the time $t_{end}$.

18. The method of claim 17, wherein the step (b) further comprises producing at least one preliminary electric signal at predetermined moment $t_{prel} < t_{st}$, said preliminary signal resulting in:
  (i) producing low level non-zero squeezing out force subjecting said expandable element to the pressure $P_{ext} < P_{ind}(t) < P_{val} + P_{ext}$ during a period between $t_{prel}$ and $t_{st}$, and
  (ii) acquiring at least two said signals for said period between $t_{prel}$ and $t_{st}$, and
  (iii) said calibrating further comprises determining of both said actual hydraulic resistances $R_1$ and $R_{exit}$ with improved precision.

* * * * *